United States Patent
Enwemeka et al.

(10) Patent No.: US 10,981,017 B2
(45) Date of Patent: *Apr. 20, 2021

(54) PHOTOERADICATION OF MICROORGANISMS WITH PULSED PURPLE OR BLUE LIGHT

(71) Applicants: SAN DIEGO STATE UNIVERSITY RESEARCH FOUNDATION, San Diego, CA (US); CAREWEAR CORP., Reno, NV (US)

(72) Inventors: Chukuka S. Enwemeka, San Diego, CA (US); John C. Castel, Reno, NV (US)

(73) Assignees: SAN DIEGO STATE UNIVERSITY RESEARCH FOUNDATION, San Diego, CA (US); CAREWEAR CORP., Reno, NV (US)

(*) Notice: Subject to any disclaimer, the term of this patent is extended or adjusted under 35 U.S.C. 154(b) by 96 days.

This patent is subject to a terminal disclaimer.

(21) Appl. No.: 16/205,182

(22) Filed: Nov. 29, 2018

(65) Prior Publication Data

US 2019/0143140 A1 May 16, 2019

Related U.S. Application Data

(63) Continuation-in-part of application No. 15/955,773, filed on Apr. 18, 2018, now Pat. No. 10,639,498, which is a continuation of application No. PCT/US2017/034396, filed on May 25, 2017.

(60) Provisional application No. 62/341,691, filed on May 26, 2016.

(51) Int. Cl.
| | | |
|---|---|---|
| *A61N 5/06* | (2006.01) | |
| *A61K 41/00* | (2020.01) | |
| *A23L 3/28* | (2006.01) | |
| *A61L 2/08* | (2006.01) | |
| *A61N 5/067* | (2006.01) | |

(52) U.S. Cl.
CPC .............. *A61N 5/0624* (2013.01); *A23L 3/28* (2013.01); *A61K 41/0057* (2013.01); *A61K 41/0071* (2013.01); *A61L 2/084* (2013.01); *A61L 2/088* (2013.01); *A23V 2002/00* (2013.01); *A61L 2202/25* (2013.01); *A61N 5/062* (2013.01); *A61N 5/0616* (2013.01); *A61N 2005/067* (2013.01); *A61N 2005/0629* (2013.01); *A61N 2005/0652* (2013.01); *A61N 2005/0653* (2013.01); *A61N 2005/0654* (2013.01); *A61N 2005/0655* (2013.01); *A61N 2005/0661* (2013.01); *A61N 2005/0663* (2013.01)

(58) Field of Classification Search
CPC ....... A61N 5/0624; A61N 5/0616; A23L 3/26; A61L 2/084; A61L 2/10
See application file for complete search history.

(56) References Cited

U.S. PATENT DOCUMENTS

| | | | |
|---|---|---|---|
| 10,639,498 B2* | 5/2020 | Enwemeka | A61L 2/16 |
| 2004/0193235 A1 | 9/2004 | Altshuler et al. | |
| 2007/0198004 A1* | 8/2007 | Altshuler | A46B 15/0036 606/9 |
| 2008/0172045 A1* | 7/2008 | Shanks | A61N 5/0616 606/3 |
| 2014/0046241 A1 | 2/2014 | Granger et al. | |

FOREIGN PATENT DOCUMENTS

| | | |
|---|---|---|
| WO | WO 2013/049491 | 4/2013 |
| WO | WO 2014/131115 | 9/2014 |

OTHER PUBLICATIONS

Dai et al., "Blue Light for Infectious Diseases: Propionibacterium Acnes, Helicobacter Pylori, and Beyond?", Drug Resist Updat. Aug. 2012; 15(4): 223-236. Doi:10.1016/j.drup.2012.07.001 (31 pgs).

* cited by examiner

*Primary Examiner* — Timothy C Cleveland
(74) *Attorney, Agent, or Firm* — Stinson LLP

(57) ABSTRACT

The present invention is directed to a system and method for photoeradication of microorganisms from a target. The target is irradiated with pulsed purple or blue light in which (a) the light pulses have a peak irradiance and a pulse duration sufficient to optically excite a photoactive molecule capable of photoeradication of the microorganisms and (b) the light pulses are separated by an off time sufficient to allow the photoactive molecule to return to a ground state creating an oxidation reaction that produces free radicals which destroy a cellular structure of the microorganisms and thereby photoeradicate all or a portion of the microorganisms. The photoactive molecule may comprise either an endogenous molecule present in the microorganisms or an exogenous molecule applied to the target.

47 Claims, 39 Drawing Sheets

*All treatment groups were statistically significant compared to the control (p<0.0001)

* Statistically significant compared to the control (p<0.0001)

* Statistically significant compared to the control (p<0.0001)

\* Statistically Significant Compared to the Control (p<0.0001)

\*\*(p<0.0001)

* Statistically Significant Compared to the Control (p<0.0001)

**(p<0.0001)

* Statistically Significant Compared to the Control ($p<0.0001$)

**($p<0.0001$)

* Statistically Significant Compared to the Control (p<0.0001)

**(p<0.0001)

PHOTOERADICATION OF MICROORGANISMS WITH PULSED PURPLE OR BLUE LIGHT

CROSS-REFERENCE TO RELATED APPLICATIONS

This application is a continuation-in-part of and claims priority to U.S. patent application Ser. No. 15/955,773, filed on Apr. 18, 2018, which is a continuation of and claims priority to PCT Patent Application Serial No. PCT/US2017/034396, filed on May 25, 2017, which is based on and claims priority to U.S. Provisional Application Ser. No. 62/341,691, filed on May 26, 2016, each of which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

Various devices for delivering light to a region of skin for therapeutic or cosmetic purposes are known in the art. The use of phototherapy, in particular blue light, as an armamentarium for antimicrobial activity has been of great interest, particularly since Enwemeka et al., first reported in 2007 that 405 nm and 470 nm light inactivate the methicillin-resistant Staphylococcus aureus (MRSA) bacteria. Current research indicates that bacteria kill rate is tied to the intensity and total amount of irradiation energy; that is, the higher the intensity used and the higher the total energy of irradiation, the better the bacteria kill rate. For example, conventional light emitting diodes (LEDs) operating in a continuous wave (CW) mode of irradiation have been used to deliver light at high irradiances and radiant exposures to increase bacteria kill rates. However, there is a risk that these high irradiances and radiant exposures may damage other tissues in the region under treatment through thermal or photochemical effects or may provide a significant optical hazard to the subject undergoing treatment.

BRIEF SUMMARY OF THE INVENTION

The present invention is directed to a system and method for photoeradication of microorganisms from a target. A light source controlled by an electronic circuit is configured to irradiate the target with pulsed purple or blue light in which (a) the light pulses have a peak irradiance and a pulse duration sufficient to optically excite a photoactive molecule capable of photoeradication of the microorganisms and (b) the light pulses are separated by an off time sufficient to allow the photoactive molecule to return to a ground state creating an oxidation reaction that produces free radicals which destroy a cellular structure of the microorganisms and thereby photoeradicate all or a portion of the microorganisms.

In a first embodiment, the target comprises a region of skin, tissue or a wound infected by various types of bacteria. In some cases, the bacteria itself synthesizes a photoactive molecule that functions as a photoreceptor for the pulsed purple or blue light—i.e., the photoactive molecule is endogenous. An example of this type of bacteria is *Propionibacterium acnes* (*P. acnes*), which synthesizes the photoactive molecule porphyrin. In other cases, the bacteria does not synthesize a sufficient amount of porphyrin or other photoactive molecules, such as Group B *Streptococcus* (GBS). In this case, a photosensitizer (such as protoporphyrin IX (PPIX), coproporphyrin III (CP III), flavin mononucleotide (FMN), or nicotinamide adenine dinucleotide (NAD)) is applied topically to the skin, tissue or wound to function as a photoreceptor for the pulsed purple or blue light—i.e., the photoactive molecule is exogenous rather than endogenous. The bacteria infected skin, tissue, or wound is treated by irradiating the region with pulsed purple or blue light. Preferably, the pulsed purple or blue light is provided at specified pulse parameters, dosages and time intervals so as to inactivate all or a portion of the bacteria at low irradiances and radiant exposures compared to those of a continuous wave (CW) mode of irradiation. As a result, it is believed that the bacteria can be inactivated without damage to other tissues in the region under treatment.

In a second embodiment, the target comprises an environment contaminated with various types of bacteria, such as methicillin-resistant *Staphylococcus aureus* (MRSA). The contaminated environment may comprise, for example, a locker room, a public or private restroom, an airplane, a school, a beach, a playground, a playing field, a hospital or a clinical environment. The contaminated environment is irradiated with pulsed purple or blue light as discussed above so as to photoeradicate the bacteria and thereby sanitize the area.

In a third embodiment, the target comprises food under storage or transport conditions that is contaminated with bacteria, such as *Salmonella* spp., *E. coli*, and *Listeria* spp. The food may be contained within, for example, a refrigeration system, a food display system, a food storage area, or a food processing system. The food is irradiated with pulsed purple or blue light as discussed above so as to photoeradicate the bacteria and thereby enhance shelf-life and reduce the potential for significant bacterial infection transmission to human and animal populations.

BRIEF DESCRIPTION OF THE DRAWINGS

Various exemplary embodiments of the present invention are described in detail below with reference to the attached drawing figures, as described below.

DETAILED DESCRIPTION OF EXEMPLARY EMBODIMENTS

Figure 1:
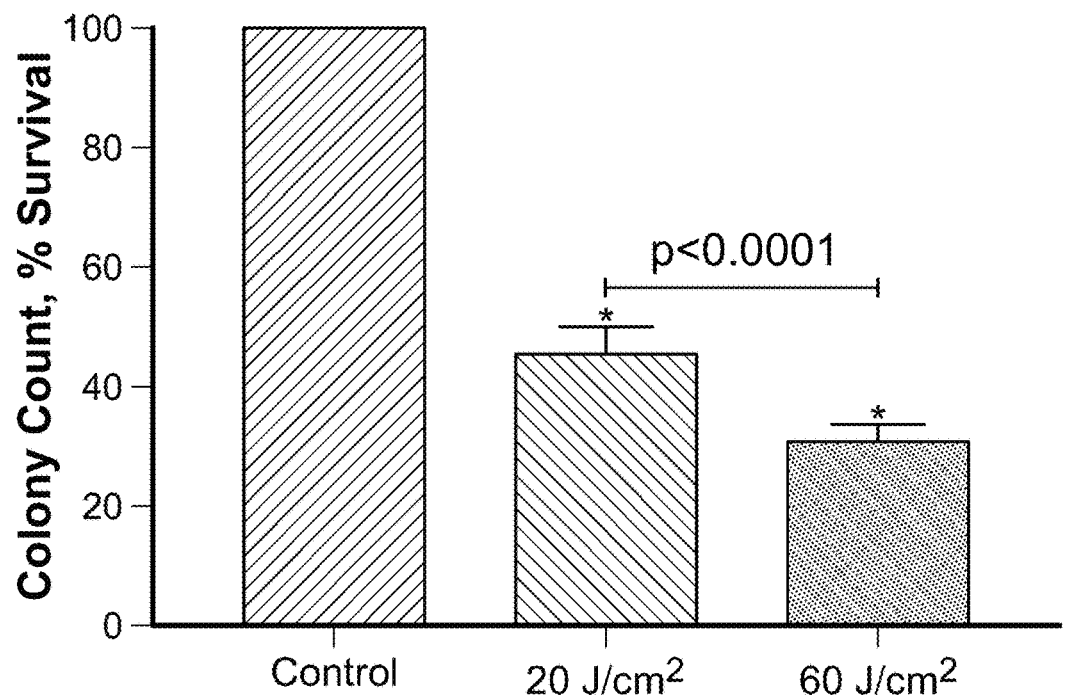
FIG. 1 is a graph depicting *P. acnes* survival when irradiated with 450 nm light at radiant exposures of 20 and 60 $J/cm^2$; irradiance of 4.5 $mW/cm^2$; continuous wave (CW) mode of irradiation; and single irradiation at 0 hours.

The present invention is directed to methods and systems for the photoeradication of microorganisms from a target using pulsed purple or blue light. While the invention will be described in detail below with reference to various exemplary embodiments, it should be understood that the invention is not limited to the specific methodologies or device configurations of these embodiments. In addition, although the exemplary embodiments are described as embodying several different inventive features, one skilled in the art will appreciate that any one of these features could be implemented without the others in accordance with the present invention.

I. General Overview

The methods and systems of the present invention may be used to photoeradicate many different types of microorganisms with pulsed purple or blue light provided at specified pulse parameters, dosages and time intervals. The pulsed light consists of a sequence of light pulses each of which has a peak irradiance and a pulse duration sufficient to optically excite photoactive molecules capable of photoeradication of the microorganisms and move them to an excited singlet state. The light pulses are separated by an off time sufficient to allow the photoactive molecules to return to their ground state, which transition creates a reaction with triplet oxygen that reduces the oxygen molecule to a highly reactive singlet state which includes singlet oxygen ($^1O_2$), hydroxyl radicals (.OH) and superoxide ($O_2^-$) ions. These are capable of destroying cellular structure of the microorganisms and thereby photoeradicate all or a portion of the microorganisms. In contrast, when light is applied in a continuous wave mode, the photoactive molecules are maintained in an excited state and fewer return to a ground state (they do so randomly as opposed to a cascade that follows the pulsing) and, thus, the effect of the light is reduced.

In a first embodiment, the invention is used to provide treatment for many different types of diseases, disorders or conditions. For example, a region of skin, tissue, or a wound infected by bacteria may be irradiated with pulsed purple or blue light for the treatment of a bacterial infection. The treatment can be provided to subjects having or who are susceptible to or at elevated risk for experiencing a bacterial skin, tissue or wound infection. Subjects may be susceptible to or at elevated risk for experiencing a bacterial infection due to family history, age, environment, and/or lifestyle. As used herein, "susceptible" and "at risk" refer to having little resistance to a certain disease, disorder or condition, including being genetically predisposed, having a family history of, and/or having symptoms of the disease, disorder or condition.

The bacterial infection may comprise any infection caused by aerobic and anaerobic bacteria (Gram positive and Gram negative). Exemplary bacterial infections include acne, psoriasis, cellulitis, erysipelas, erythrasma, folliculitis and skin abscesses, hidradenitis suppurativa, impetigo and ecthyma, lymphadenitis, lymphangitis, necrotizing skin infections, staphylococcal scalded skin syndrome, as well as wound and tissue infections such as osteomyelitis.

In a second embodiment, the invention is used to enable photoeradication of bacteria from contaminated environments. The bacteria may comprise any aerobic and anaerobic bacteria (Gram positive and Gram negative). For example, community associated methicillin-resistant *Staphylococcus aureus* (MRSA) strains are often acquired from places that people congregate, such as locker rooms, public or private restrooms, airplanes, schools, beaches, playgrounds, playing fields, etc., while hospital associated MRSA is contacted in hospitals and clinical environments. These contaminated environments may be irradiated with pulsed purple or blue light to provide a more effective way to sanitize such places. The pulsed purple or blue light may be placed together with a white light to act as a dual light source, one for lighting and one for bactericidal effects. The pulse treatment sequences could be applied daily to the environment or on any other periodic or scheduled basis (e.g., the pulse treatment sequence could be applied to the interior surfaces of an airplane between the various successive flights).

In a third embodiment, the invention is used to enable photoeradication of bacteria from food. The bacteria may comprise any aerobic and anaerobic bacteria (Gram positive and Gram negative). For example, foods may be contaminated with *Salmonella* spp., *E. Coli*, or *Listeria* spp. *Salmonella* spp. contains CspH, a cold shock protein that protects the bacteria at 50° C. As such, refrigeration at this temperature may not be adequate to kill the bacteria. Refrigeration in retail may be a higher temperature further exacerbating the problem of bacterial growth. Globally, there are more than 80.3 million cases annually of *Salmonella* spp. with more than 115,000 deaths. Contaminated foods may be irradiated with pulsed purple or blue light to provide a more effective way to extend shelf life and prevent bacterial transmission to humans and animals exposed to such foods. The pulsed light may be built into commercial, residential or portable refrigeration systems, food display systems, food storage areas and systems for food processing. For example, the pulsed purple or blue light may be activated whenever a door of a refrigeration system is opened and closed. When the door is opened, the light would be white and when closed the pulsed purple or blue light would be applied at the correct dose and treatment sequence. The treatment sequence would be applied daily and/or as new food items are added to the food storage or processing system.

For all three embodiments discussed above, exemplary bacteria include *Propionibacterium acnes*, Group B *Streptococcus, Propionibacterium* spp., *Staphylococcus* spp. (including methicillin resistant strains), *Clostridium* spp., *Echerichia* spp., *Pseudomonas* spp., *Campylocbacter* spp., *Listeria* spp., *Leuconostoc* spp., *Bacillus* spp., *Acinetobacter* spp., *Streptococcus* spp., *Brucella* spp., *Proteus* spp., *Klebsiella* spp., *Shigella* spp., *Helicobacter* spp., *Mycobacterium* spp., *Enterococcus* spp., *Salmonella* spp., *Chlamydia* spp., *Porphynomonas* spp., *Stenotrophomonas* spp., and *Elizabethkingia* spp. Of course, other types of bacteria may also be targeted in accordance with the present invention.

In some cases, the bacteria itself synthesizes a photoactive molecule that functions as a photoreceptor for the pulsed purple or blue light—i.e., the photoactive molecule is endogenous. An example of this type of bacteria is *Propionibacterium acnes* (*P. acnes*), which synthesizes the photoactive molecule porphyrin. In other cases, the bacteria does not synthesize a sufficient amount of porphyrin or other photoactive molecules, such as Group B *Streptococcus* (GBS). While GBS contains chromophores such as characteristic brick-red pigment ornithine rhamnopolyenic (rhamnolipid), a β-haemolysin/cytolysin, and granadaene, it is believed that these chromophores are not implicated in the suppression of bacteria growth upon irradiation with pulsed blue or purple light. In this case, the bacteria is supplemented with a photosensitizer that functions as a photoreceptor for the pulsed purple or blue light—i.e., the photoactive molecule is exogenous rather than endogenous.

Examples of suitable photosensitizers include protoporphyrin IX (PPIX), coproporphyrin III (CP III), flavin mononucleotide (FMN), and nicotinamide adenine dinucleotide (NAD). Of course, other types of photosensitizers may also be used in accordance with the present invention.

In accordance with the invention, bacteria or other microorganisms are inactivated via the application of purple or blue light in a pulsed mode of irradiation. As used herein, "purple or blue light" refers to light having a wavelength ranging from about 380 nm to about 500 nm (e.g., 380, 390, 400, 410, 420, 430, 440, 450, 460, 470, 480, 490, 500 nm or some value therebetween). A particularly suitable wavelength is about 450 nm. The pulses provided can be a square wave, rectified sinusoidal waveform or any combination thereof, although other pulse shapes may also be used in accordance with the present invention. A square wave with a rise time of less than 1 microsecond is preferred.

The pulsed purple or blue light is provided at radiant exposures that can range from about 0.5 $J/cm^2$ to about 60 $J/cm^2$, with a preferred range of about 3.6 $J/cm^2$ to about 20 $J/cm^2$, and a more preferred range of about 3.6 $J/cm^2$ to about 5 $J/cm^2$. The average irradiance can range from about 0.1 $mW/cm^2$ to about 20 $mW/cm^2$, with an average irradiance of about 2 $mW/cm^2$ to about 3 $mW/cm^2$ being preferred at the tissue surface, contaminated environment or food surface.

It should be understood that the low levels of light used in connection with the present invention (e.g., average irradiances of about 2 $mW/cm^2$ to about 3 $mW/cm^2$ and radiant exposures of about 3.6 $J/cm^2$ to about 5 $J/cm^2$) are very safe to the eye and meet international blue light safety requirements, including IEC TR 62778:2014 (Application of IEC 62471 for the assessment of blue light hazard to light sources and luminaries), IEC 62471:2006 (Photobiological safety of lamps and lamp systems), IEC 60601-2-57:2011 (Medical Electrical equipment—Part 2-57: Particular requirements for the basic safety and essential performance of non-laser light source equipment intended for therapeutic, diagnostic, monitoring and cosmetic/aesthetic use). This provides a significant advantage over continuous wave (CW) light sources that deliver light at high irradiances and radiant exposures. These higher output light sources also require significant cooling and heat sinking and, thus, are not ideal for refrigeration applications.

The pulse parameters of the pulsed purple or blue light are preferably selected to optimize the photochemical reaction of the photoactive molecule used to photoeradicate the microorganisms, as described above. In most embodiments, the peak irradiance of the light pulses ranges from 0.3 $mW/cm^2$ to 60 $mW/cm^2$ with a preferred range of about 6 $mW/cm^2$ to about 15 $mW/cm^2$ at a duty factor of 33%. At other duty factors, the peak irradiance may be higher or lower so that the average irradiance stays within the preferred ranges of irradiance described herein. The duty factor is typically in the range of about 20% to about 33%.

In most embodiments, the pulse duration of the light pulses ranges from 5 microseconds to 1,000 microseconds, and the off time between the light pulses ranges from 10 microseconds to 1 second. A suitable combination may range from about 5 microseconds to about 30 microseconds for the pulse duration with off times ranging from about 10 microseconds to about 100 microseconds. A particularly suitable combination provides a pulse duration of about 10 microseconds and an off time of about 20 microseconds. The light pulses are typically provided at a pulse repetition rate that ranges from 33 kHz to 40 kHz.

It should be understood that the optimal pulse parameters for destruction of bacteria—i.e., the pulse intensity and on/off states that result in the depletion and restoration/recovery of porphyrins or other photoactive molecules involved in bacterial photoeradication—will vary between different types of bacteria.

The pulsed purple or blue light may be applied one time (i.e., single irradiation session) and is preferably provided multiple times (i.e., multiple irradiation sessions) at the desired radiant exposures (fluence) and power density (irradiance). One skilled in the art will appreciate that the irradiation time for each irradiation session is dependent on the dose, and is typically in the range of about 20 minutes to about 45 minutes for the irradiances and radiant exposures used in connection with the present invention.

In some embodiments, the duration of exposure may be controlled by the decay and recharge in fluorescence of the bacteria. In that configuration, the exposure would stop when the fluorescence has depleted to a preset level indicating that there is insufficient photo-activity to maintain bacterial kill and then restart when the fluorescence has returned to another preset level. Also, the irradiation sessions may be timed to a replication cycle of the microorganisms so that the irradiation sessions restart prior to replication of the microorganisms.

Preferably, the pulsed purple or blue light is applied during a plurality of irradiation sessions at pre-defined time intervals in accordance with an irradiation schedule, as described below. The time interval between irradiation sessions may range from about one hour to about four hours (e.g., 1, 2, 3, 4 hours or some value therebetween) with two or three (or more) irradiation sessions per day. These timed irradiation sessions may also be repeated on two, three, four or more days in certain embodiments, or in the case of environmental or food irradiation on a daily basis. In some embodiments, the pulsing has been found to be optimized when the irradiation schedule includes the application of pulses three times per day with a three hour time interval between applications, which may be repeated on two or more days (e.g., when the pulses are applied at 0, 3, 6, 24, 27, 30, 48, 51 and 54 hours). Of course, other irradiation schedules that are suitable for a particular application may also be used within the scope of the present invention. The irradiation schedule is preferably chosen to provide a survival rate for the microorganisms of less than 50% and preferably 0% (i.e., a survival rate of 50%, 40%, 30%, 20%, 10%, 5%, 0% or some value therebetween).

In addition to the basic pulsing of the purple or blue light as described above, the pulsed mode may be further modulated when used for irradiation of human or animal tissue, i.e., gated on and off with a low frequency signal timed to coincide with the heart rate or at a rate similar to the heart rate (i.e., 0.5 to 2 Hz or a multiple or harmonic thereof). This signal allows for recharge of the free oxygen, porphyrins or other molecules responsible for photochemical activation of cellular killing mechanisms during the resting period of the photostimulation. Duty factors in the range of 5% to 95% may be used for this modulation.

Any suitable light source may be used to generate the pulsed purple or blue light in accordance with the present invention. Exemplary light sources include various types of lasers, light emitting diodes (LEDs), organic light emitting diodes (OLEDs), printed light emitting diodes (printed LEDs), polymer light emitting diodes (PLEDs) also known as light emitting polymers (LEPs), quantum dot light emitting diodes (QDLEDs), and fluorescent tubes emitting light in the purple or blue spectral region. Exemplary light sources are described in greater detail below.

For the first embodiment directed to the treatment of various diseases, disorders or conditions, devices comprised of printed LEDs or OLEDs on flexible substrates are preferred due to their ability to produce light with an intensity that is substantially constant across the surface of the light source so as to provide substantially uniform light emission when the light source is in contact with or illuminates skin or tissue of a subject. The devices are also able to conform to the skin or tissue surface to maximize optical coupling. In addition, a layer of hydrogel may be used as an adhesive to contact the flexible substrate to the skin or tissue surface and thereby provide optical light piping and coupling. The hydrogel layer may also contain therapeutic substances used to enhanced bacterial inhibition or kill.

For the second and third embodiments directed to photoeradication of bacteria from contaminated environments and food, respectively, it is possible to use strips or sheets of printed LEDs or OLEDs, high power LEDs or even tube lamps emitting modulated light in the UVA through blue spectral range. Certain of these strips or sheets may have rows of blue lamps in parallel or interspersed with white lamps or phosphor coated or Stokes conversion quantum dots or the like to produce white light. As used herein, "white light" means light having a color temperature in the range of about 1700 kelvins (K) to about 9500 kelvins (K).

In some embodiments, the light source is controlled by an electronic circuit with a drive circuit and microcontroller that provides a preprogrammed sequence of light pulses at a fixed dose during each irradiation session. In other embodiments, the light source is controlled by an electronic circuit with one or more sensors that operate in a closed loop to provide feedback to a microcontroller so as to dynamically control the dose during a treatment session. Exemplary electronic circuits for both preprogrammed control and dynamic control of a light source are described in greater detail below. In some embodiments, the controller will receive input from a lighting system or the opening or closing of a door in a refrigeration or storage unit to activate the pulsed purple or blue lights and provide the appropriate daily irradiation sequence.

II. In Vitro Testing of *P. acnes* Cultures to Determine Feasibility and Reproducibility of Inactivation with Light Irradiation Testing was performed to determine the feasibility and reproducibility of 450 nm light to inactivate *P. acnes* using printed LED flexible lamps operated in a continuous wave (CW) irradiation mode, a pulsed irradiation mode with a 33% duty factor, and a pulsed irradiation mode with a 20% duty factor (referred to hereinafter as CW mode, 33% DF pulsed mode, and 20% DF pulsed mode).

Culturing *P. acnes*

A vial of *P. acnes* (ATCC 6919) was obtained from the American Type Culture Collection (ATCC) and cultures started according to ATCC recommendations. Briefly, under anaerobic conditions, the lyophilized pellet was rehydrated in 500 µL modified reinforced clostridial broth (pre-reduced) and transferred into another tube containing 5 mL clostridial broth. Test tubes were labelled as "Start Cultures" (SC) and 200 µL transferred onto a reinforced clostridial agar plate. The bacteria were streaked on the plates for isolation of single colonies by the "clock plate technique" to check colony morphology and purity. These plates were called "start plates." Both tube/plate were placed in an anaerobic chamber with BD Gas-Pak EZ anaerobic container system sachets. The anaerobic chamber was then placed inside a 37°

C. incubator for 72 hours. After 72 hours of growth period, culture tubes were removed from the 37° C. incubator and tested for their susceptibility to irradiation with 450 nm blue light.

Illumination of Bacteria

A 5 mL liquid culture was grown for 3 days and 1 mL pipetted into a sterile microcentrifuge tube and centrifuged at 13,300 rpm for five minutes. The supernatant was removed and discarded. The pellet was re-suspended in 1 mL saline and optical density adjusted using McFarland standard to 0.8 to 1.0 at 625 nm for a concentration of $10^8$ CFU/mL. The bacteria were diluted to a concentration of $1 \times 10^6$ CFU/mL and 2 µL streaked onto reduced clostridial agar plates (12 well plates were used, which enabled triplicate irradiations with 3 patches simultaneously) and irradiated in an anaerobic chamber with various protocols. A set of non-irradiated plates served as controls. After irradiation, plates were placed upside down in the anaerobic chamber, along with a Gas-pak sachet and incubated at 37° C. for 72 hours. The colonies were then counted, percentage survival computed and morphology checked. Illumination times and intervals were optimized based on experimentation as to which dose and sequence provided the most effective kill rates.

Quantification of Bacterial Colonies

Standardized digital images of P. acnes colonies were taken 72 hours after incubation, with the camera positioned 10 cm perpendicularly above each plate to ensure consistency of colony magnification. Colonies were counted, and percent survival calculated, comparing irradiated groups and non-irradiated controls.

Description of Test Protocols and Test Results

Example 1

Figure 22:
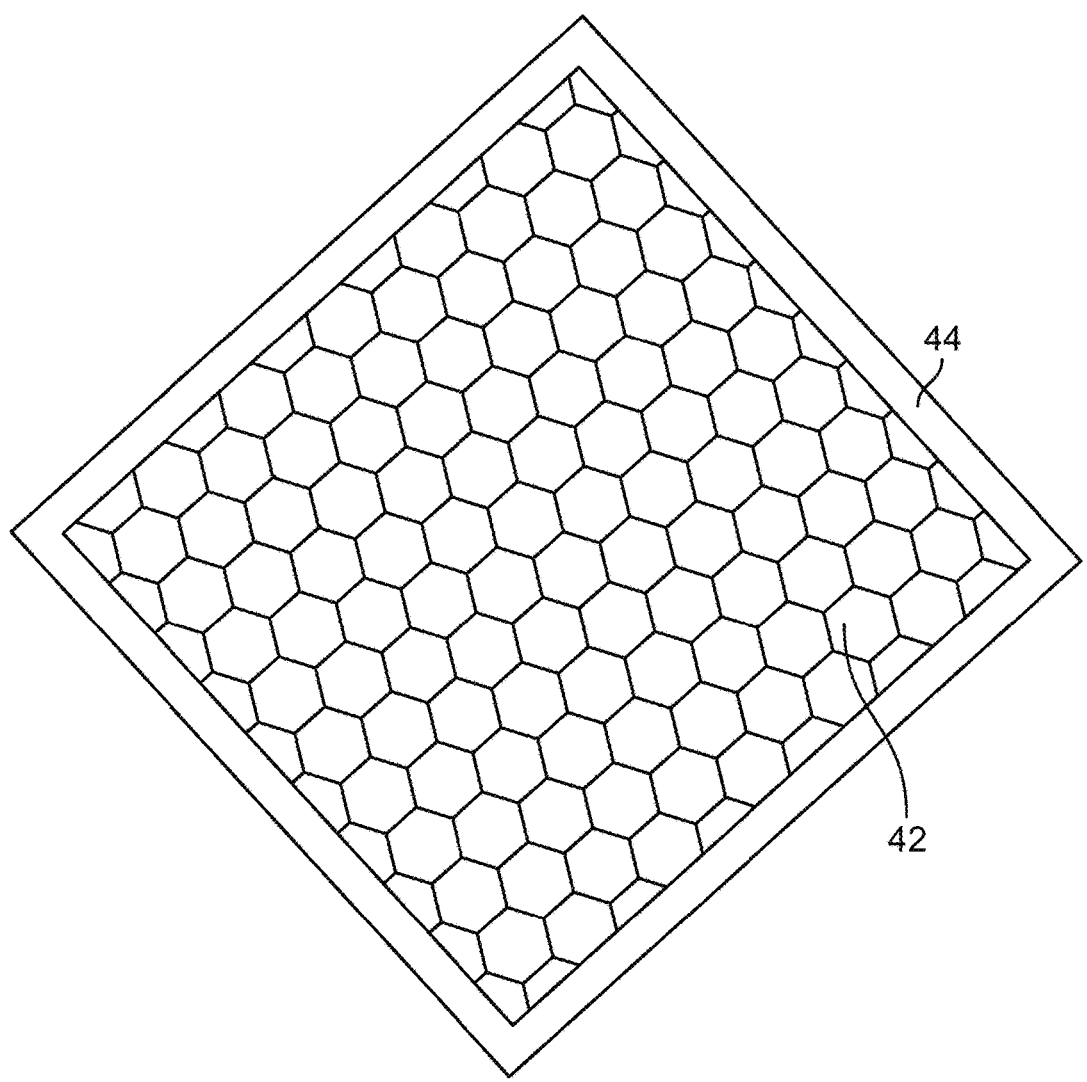
FIG. 22 illustrates a plurality of light emitting diodes printed on a flexible film (referred to herein as a printed LED flexible lamp or a lighted substrate) that is suitable for use in accordance with the present invention.

A first series of experiments involved culturing P. acnes and illuminating the bacteria with a 450 nm lighted substrate, an example of which is shown in FIG. 22 (described below). The lighted substrate was set to operate in CW mode and driven with a constant current source. The peak and average irradiances were the same, i.e., 4.5 mW/cm$^2$, due to the continuous output. The bacteria were irradiated one, three or four times with different radiant exposures, as described below. Three substrates were provided for the experiments and all were tested and calibrated.

Figure 2:
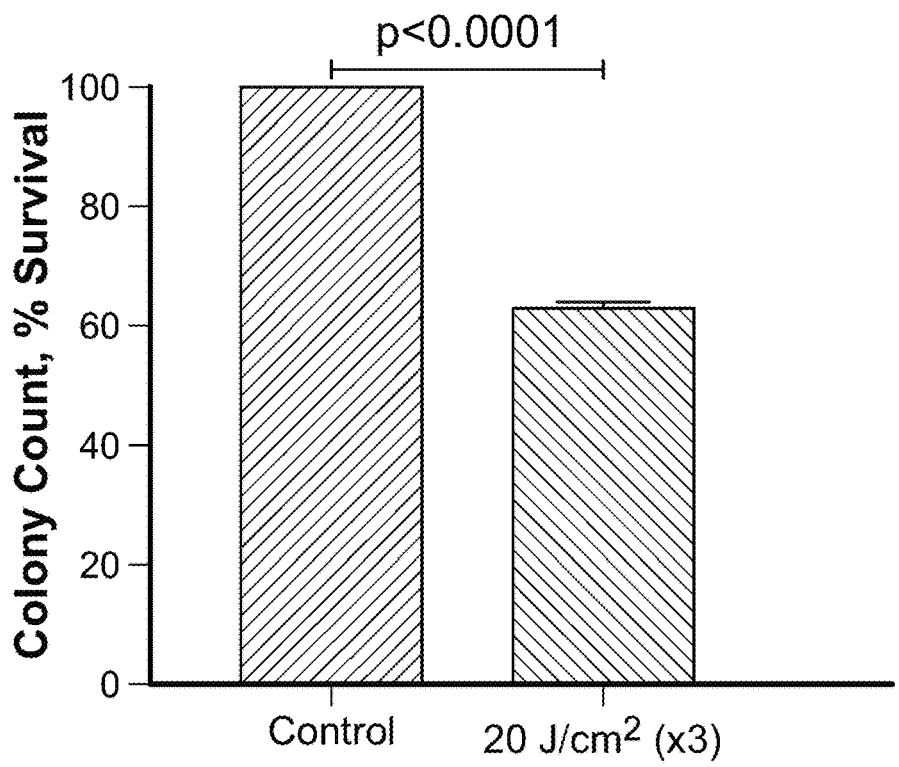
FIG. 2 is a graph depicting *P. acnes* survival when irradiated with 450 nm light at a radiant exposure of 20 $J/cm^2$; irradiance of 4.5 $mW/cm^2$; continuous wave (CW) mode of irradiation; and multiple irradiation at 0, 24 and 48 hours.
Figure 3:
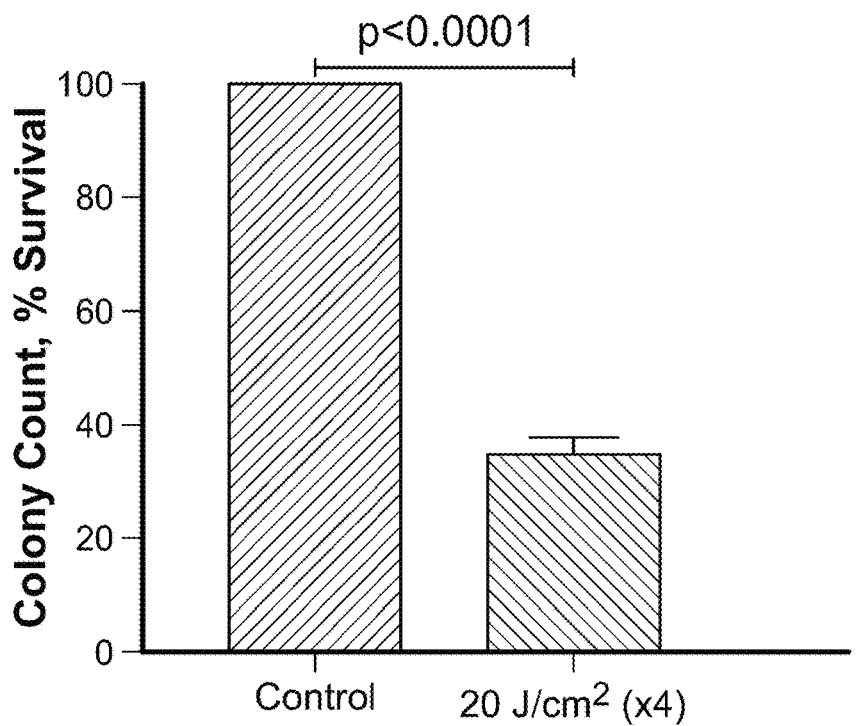
FIG. 3 is a graph depicting *P. acnes* survival when irradiated with 450 nm light at a radiant exposure of 20 $J/cm^2$; irradiance of 4.5 $mW/cm^2$; continuous wave (CW) mode of irradiation; and multiple irradiation at 0, 4, 24 and 48 hours.

The data is presented in FIGS. 1-4. As illustrated in FIG. 1, single irradiation of bacteria with radiant exposures of 20 J/cm$^2$ and 60 J/cm$^2$ produced statistically significant decreases in percent survival when compared to the control, with maximum reduction of 31% observed at 60 J/cm$^2$. As illustrated in FIG. 2, triple irradiation of bacteria with a radiant exposure of 20 J/cm$^2$ at 0, 24 and 48 hours reduced the percent survival to 62%, which was significantly different from the control. As illustrated in FIG. 3, when bacteria were irradiated four times with a radiant exposure of 20 J/cm$^2$ at 0, 4, 24 and 48 hours, a significant decrease in percent survival of 31% was observed when compared to the control. This percent survival was much lower than the percent survival of 62% observed with triple irradiation at 0, 24 and 48 hours (FIG. 2). It was found that four exposures at 20 J/cm$^2$ applied at 0, 4, 24 and 48 hours provided the highest kill rates as compared to a single, double or triple exposure.

Figure 4:
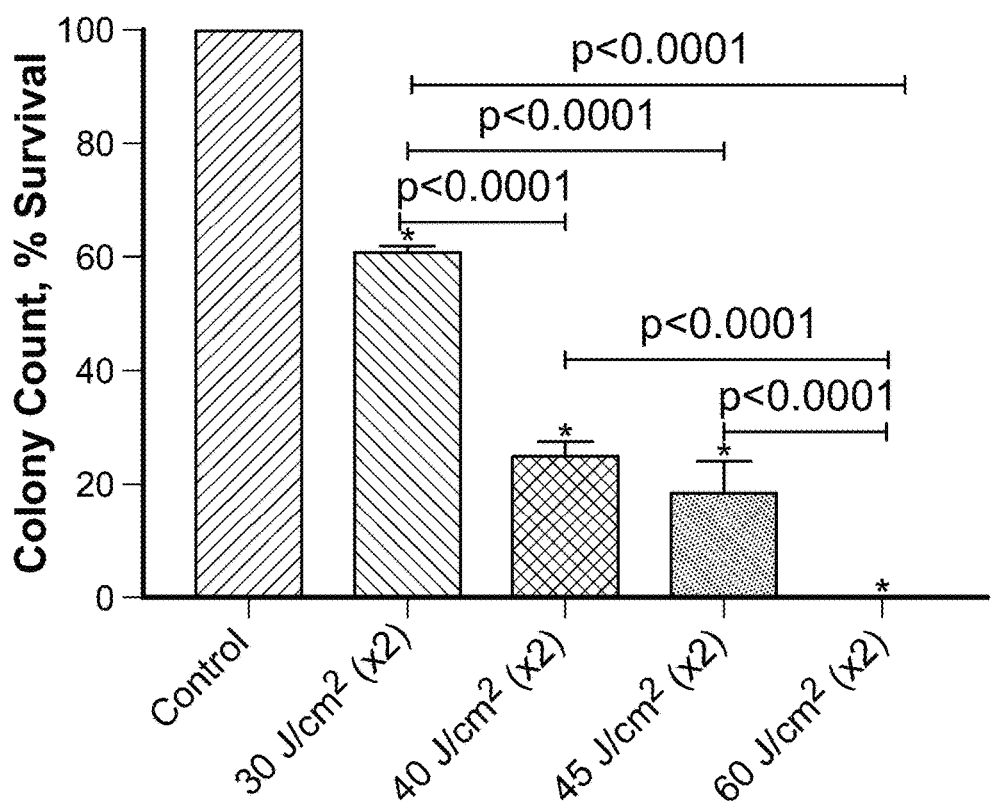
FIG. 4 is a graph depicting *P. acnes* survival when irradiated with 450 nm light at radiant exposures of 30, 40, 45 and 60 $J/cm^2$; irradiance of 4.5 $mW/cm^2$; continuous wave (CW) mode of irradiation; and multiple irradiation at 0 and 4 hours.

FIG. 4 illustrates the relationship between different radiant exposures for a double exposure occurring at 0 and 4 hours. Double irradiation of bacteria with radiant exposures of 30, 40, 45 and 60 J/cm$^2$ at 0 and 4 hours produced a significant dose dependent decrease in percent survival as the dose increased, with complete inactivation observed at 60 J/cm$^2$.

Example 2

A second series of experiments involved culturing P. acnes and illuminating the bacteria with the 450 nm lighted substrate shown in FIG. 22. The lighted substrate was set to operate in CW mode, 33% DF pulsed mode, or 20% DF pulsed mode, as described below, and driven with a constant current source. The average irradiance was the same for all modes, i.e., 5 mW/cm$^2$. The peak irradiance was 15 mW/cm$^2$ in the 33% DF pulsed mode (i.e., three times higher than CW mode) and 25 mW/cm$^2$ in the 20% DF pulsed mode (i.e., five times higher than CW mode). In the 33% DF pulsed mode, the pulse duration was 10 microseconds with an off time of 20 microseconds, and the pulse repetition rate was 33 kHz. In the 20% DF pulsed mode, the pulse duration was 5 microseconds with an off time of 20 microseconds, and the pulse repetition rate was 40 kHz. The bacteria were irradiated twice at 0 and 4 hours with different radiant exposures, as described below. Three substrates were provided for the experiments and all were tested and calibrated.

Figure 5:
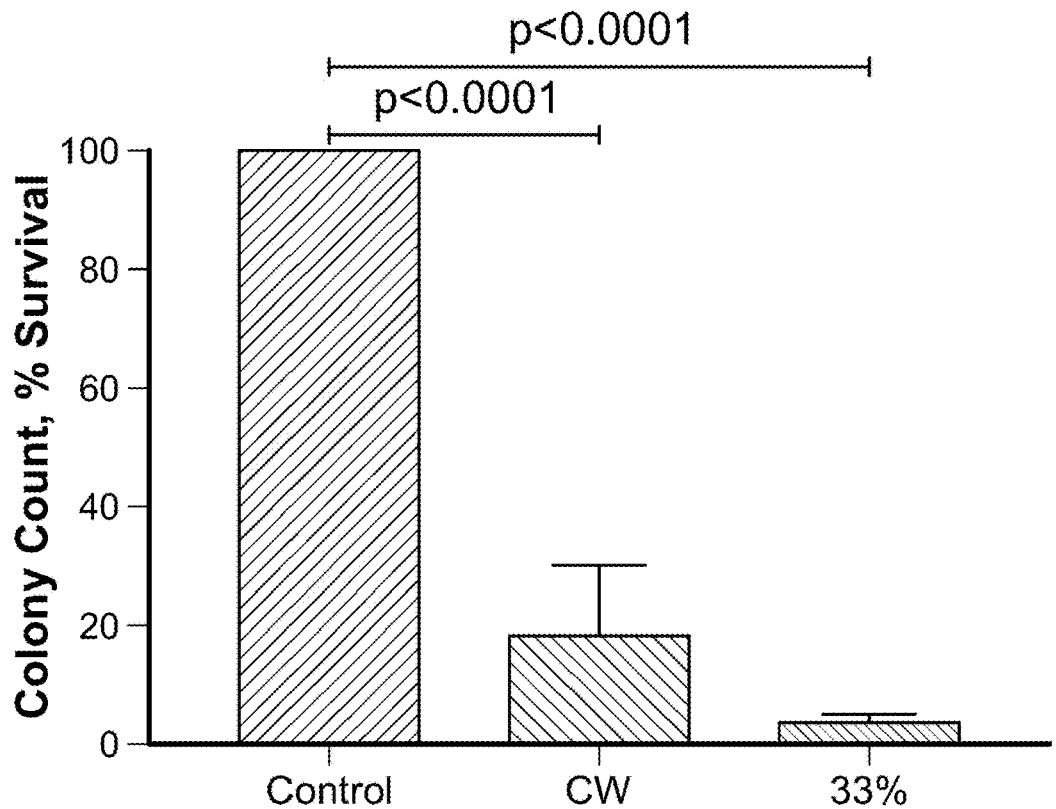
FIG. 5 is a graph depicting *P. acnes* survival when irradiated with 450 nm light at a radiant exposure of 60 J/cm$^2$; average irradiance of 5 mW/cm$^2$; continuous wave (CW) mode of irradiation and pulsed mode of irradiation (33% duty factor); and multiple irradiation at 0 and 4 hours.
Figure 6:
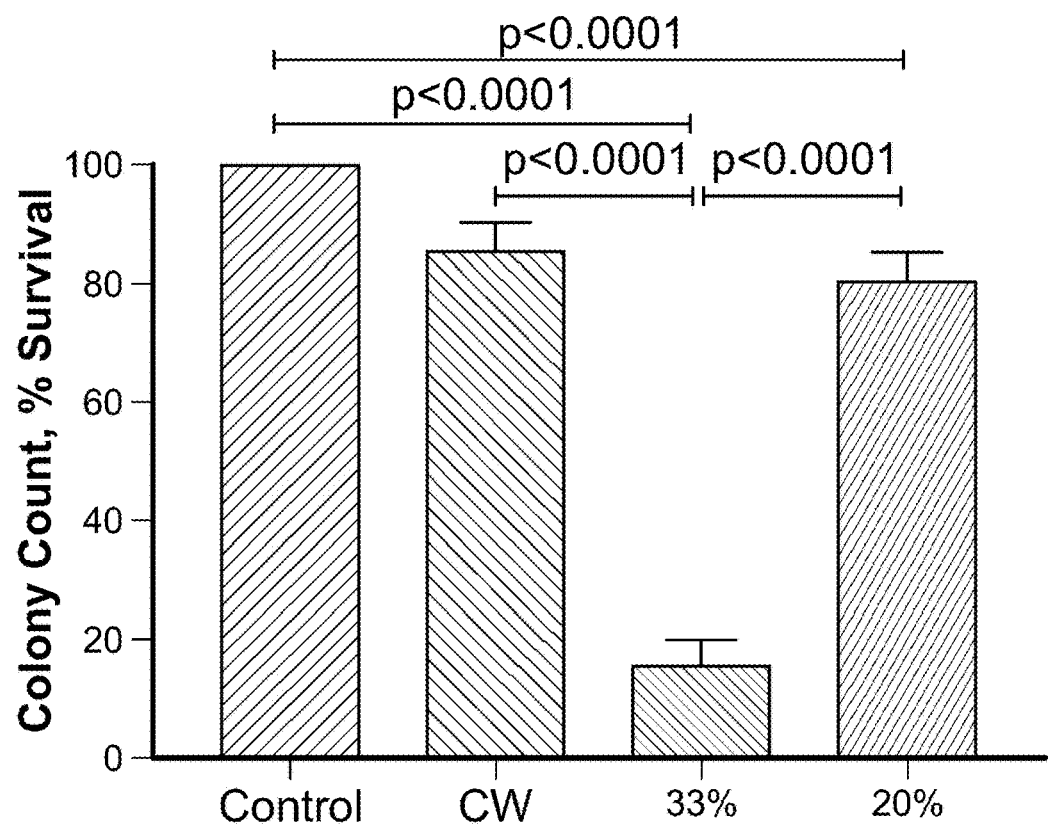
FIG. 6 is a graph depicting *P. acnes* survival when irradiated with 450 nm light at a radiant exposure of 20 J/cm$^2$; average irradiance of 5 mW/cm$^2$; continuous wave (CW) mode of irradiation and pulsed mode of irradiation (33% and 20% duty factors); and multiple irradiation at 0 and 4 hours.

The data is presented in FIGS. 5 and 6. As illustrated in FIG. 5, double irradiation of bacteria at 0 and 4 hours with a radiant exposure of 60 J/cm$^2$ in CW mode and 33% DF pulsed mode revealed marked decreases in percent survival when compared to the control, with maximum reduction to a percent survival of 2.2% observed in the 33% DF pulsed mode. As illustrated in FIG. 6, double irradiation of bacteria at 0 and 4 hours with a radiant exposure of 20 J/cm$^2$ in CW mode, 33% DF pulsed mode and 20% DF pulsed mode again revealed that the 33% DF pulsed mode was more efficacious in suppressing bacteria growth than the CW mode and the 20% DF pulsed mode, with a percent survival of 16% for the 33% DF pulsed mode compared to percent survivals of 87% and 80% for the CW mode and 20% DF pulsed mode, respectively.

Example 3

A third series of experiments involved further testing with a change to the exposure schedule based on the findings described in FIG. 3, i.e., that four irradiation exposures (0, 4, 24 and 48 hours) provided the best kill rate at a radiant exposure of 20 J/cm$^2$. These experiments involved culturing P. acnes and illuminating the bacteria with the 450 nm lighted substrate shown in FIG. 22. The lighted substrate was set to operate in CW mode or 33% DF pulsed mode, as described below, and driven with a constant current source. The average irradiance was selectable at 2 and 3.5 mW/cm$^2$ in the 33% DF pulsed mode compared to an average irradiance of 5 mW/cm$^2$ in the CW mode. In the 33% DF pulsed mode, the pulse duration was 10 microseconds with an off time of 20 microseconds, and a pulse repetition rate of 33 kHz. The bacteria were irradiated four times at 0, 4, 24 and 48 hours with different radiant exposures of 5, 10 and 20 J/cm$^2$. Three substrates were provided for the experiments and all were tested and calibrated.

Figure 7:
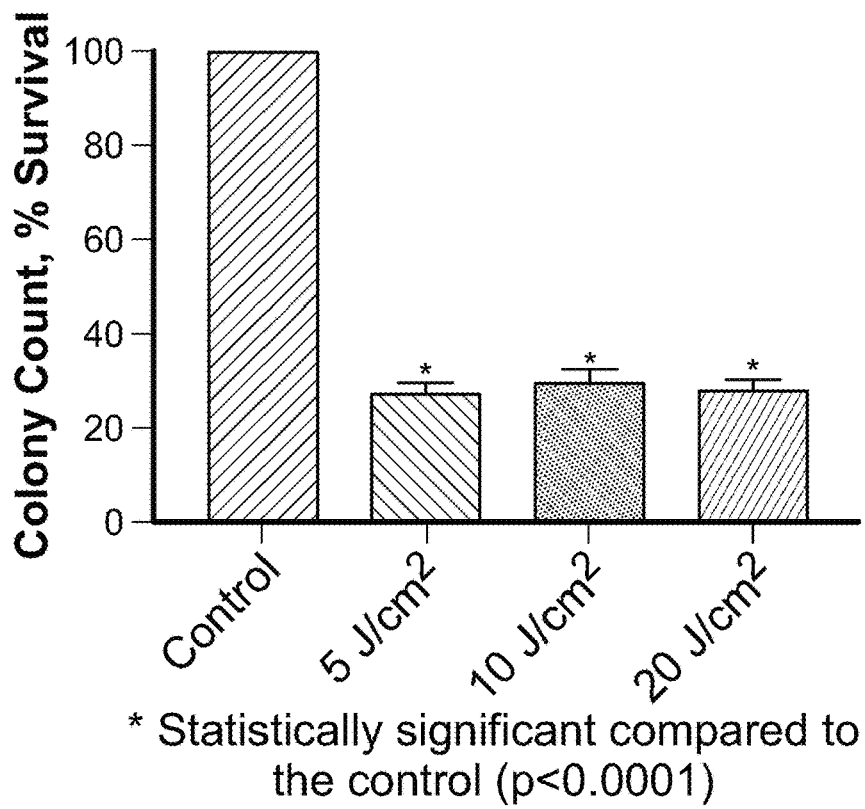
FIG. 7 is a graph depicting *P. acnes* survival when irradiated with 450 nm light at radiant exposures of 5, 10 and 20 J/cm$^2$; average irradiance of 2 mW/cm$^2$; pulsed mode of irradiation (33% duty factor); and multiple irradiation at 0, 4, 24 and 48 hours.
Figure 8:
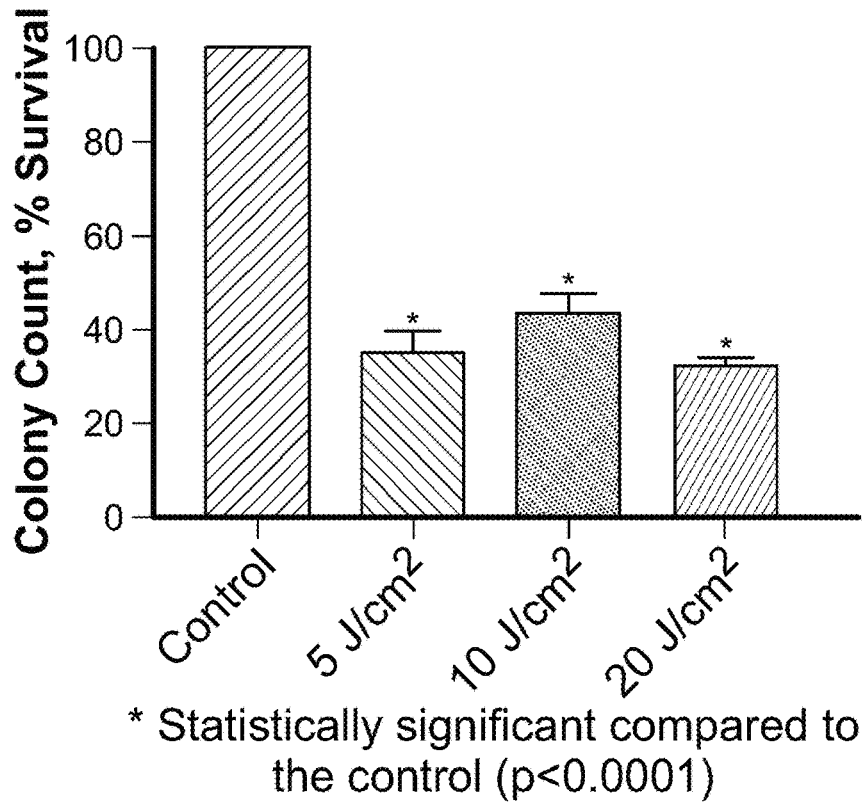
FIG. 8 is a graph depicting *P. acnes* survival when irradiated with 450 nm light at radiant exposures of 5, 10 and 20 J/cm$^2$; average irradiance of 3.5 mW/cm$^2$; pulsed mode of irradiation (33% duty factor); and multiple irradiation at 0, 4, 24 and 48 hours.
Figure 9:
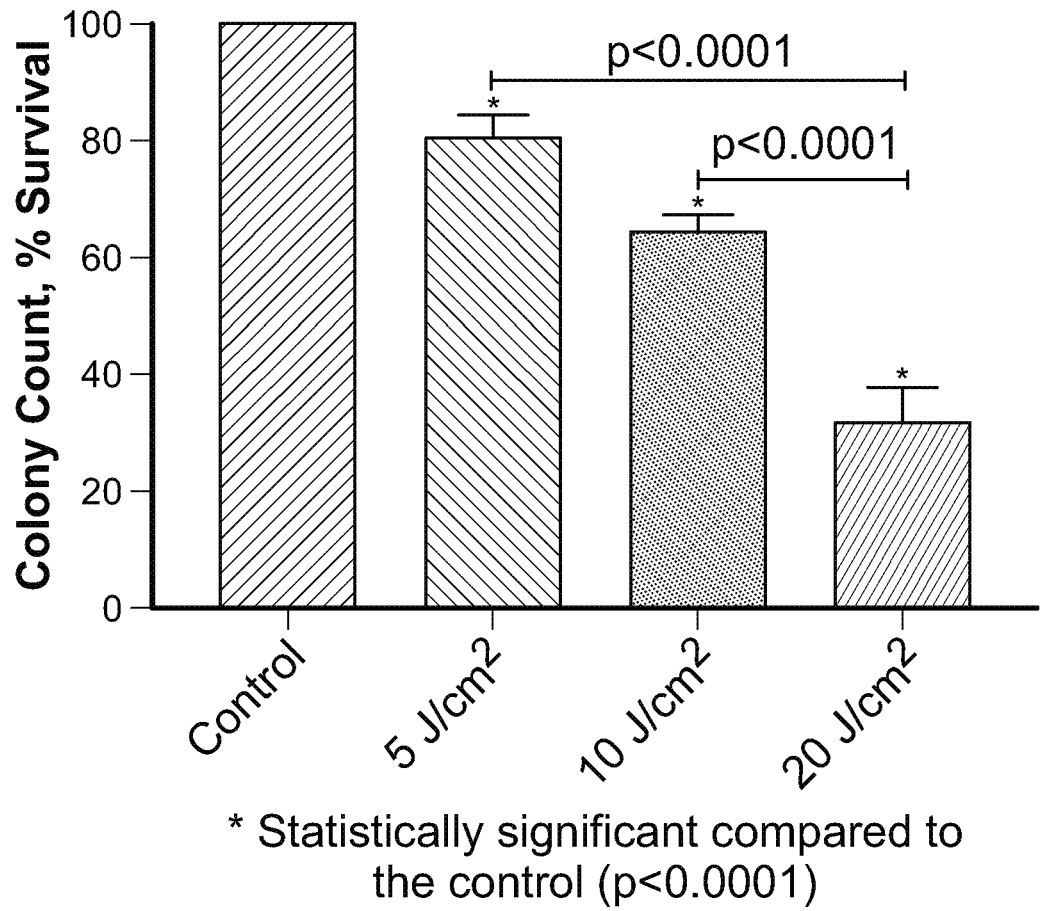
FIG. 9 is a graph depicting *P. acnes* survival when irradiated with 450 nm light at radiant exposures of 5, 10 and 20 J/cm$^2$; irradiance of 5 mW/cm$^2$; continuous wave (CW) mode of irradiation; and multiple irradiation at 0, 4, 24 and 48 hours.

The data is presented in FIGS. 7-9. As illustrated in FIG. 7, irradiation of cultures four times (0, 4, 24 and 48 hours) with radiant exposures of 5, 10 and 20 J/cm$^2$ and an average irradiance of 2 mW/cm$^2$ in the 33% DF pulsed mode showed significant decreases in percent survival when compared to the control, however, no significant differences were observed between the doses. These results indicated that no significant differences in the percent survival existed with increases in radiant exposure from 5 J/cm$^2$ to 20 J/cm$^2$ at an average irradiance of 2 mW/cm$^2$.

As illustrated in FIG. 8, irradiation of cultures four times (0, 4, 24 and 48 hours) with radiant exposures of 5, 10 and 20 J/cm$^2$ and an average irradiance of 3.5 mW/cm$^2$ in the 33% DF pulsed mode showed significant decreases in percent survival when compared to the control, however, no significant differences were observed between the doses. These results indicate that no significant differences in the percent survival existed with increases in radiant exposure from 5 J/cm$^2$ to 20 J/cm$^2$ at an average irradiance of 3.5 mW/cm$^2$.

As illustrated in FIG. 9, irradiation of cultures four times (0, 4, 24 and 48 hours) with radiant exposures 5, 10 and 20 J/cm$^2$ and an irradiance of 5 mW/cm$^2$ in the CW mode showed significant decreases in percent survival when compared to the control. However, unlike the results shown in FIGS. 7 and 8, the decrease in percent bacterial survival was dose dependent with significant decreases observed between the radiant exposures of 5 J/cm$^2$ and 10 J/cm$^2$ and between 10 J/cm$^2$ and 20 J/cm$^2$ at an irradiance of 5 mW/cm$^2$.

Thus, it can be seen that the CW mode behaved in a linear dose dependent fashion. However, a significant and unexpected result was obtained with respect to the 33° % DF pulsed mode, i.e., there was no significant radiant exposure dependency on kill rates for different average irradiances of 2 and 3.5 mW/cm$^2$. As a result, a novel treatment was discovered using two to four doses in sequence in the 33% DF pulsed mode at a radiant exposure of 5 J/cm$^2$.

III. In Vitro Testing of *P. acnes* Cultures to Determine Optimal Parameters of Inactivation with Light Irradiation The preliminary results described above revealed that pulsed blue light was more effective in suppressing bacteria growth than continuous wave. Thus, further testing was performed to determine the optimal parameters of 450 nm light to inactivate *P. acnes* using printed LED flexible lamps operated in a pulsed irradiation mode with a 33% duty factor.

A suspension of *P. acnes* bacteria diluted to a concentration of 1×10$^6$ CFU/mL, as discussed in Section II above, was streaked onto reduced clostridial agar plates that were irradiated or not (controls) in an anaerobic chamber. The tests were conducted using three different irradiation substrates (with the same power output) with each placed at the top of two wells on a 12 well plate. This enabled results to be obtained in triplicates (six sets of data for each experiment). After irradiation protocols were completed, plates were placed upside down in the anaerobic chamber, along with a Gas-pak sachet and incubated at 37° C. for 72 hours. The colonies were then counted, percentage survival computed and morphology checked.

Description of Test Protocols and Test Results

Example 1

A first experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 3 mW/cm$^2$. The pulse duration was 10 microseconds with an off time of 20 microseconds, and a pulse repetition rate of 33 kHz. The bacteria were irradiated four times at 0, 4, 24 and 48 hours with different radiant exposures of 5, 10 and 20 J/cm$^2$.

Figure 10:
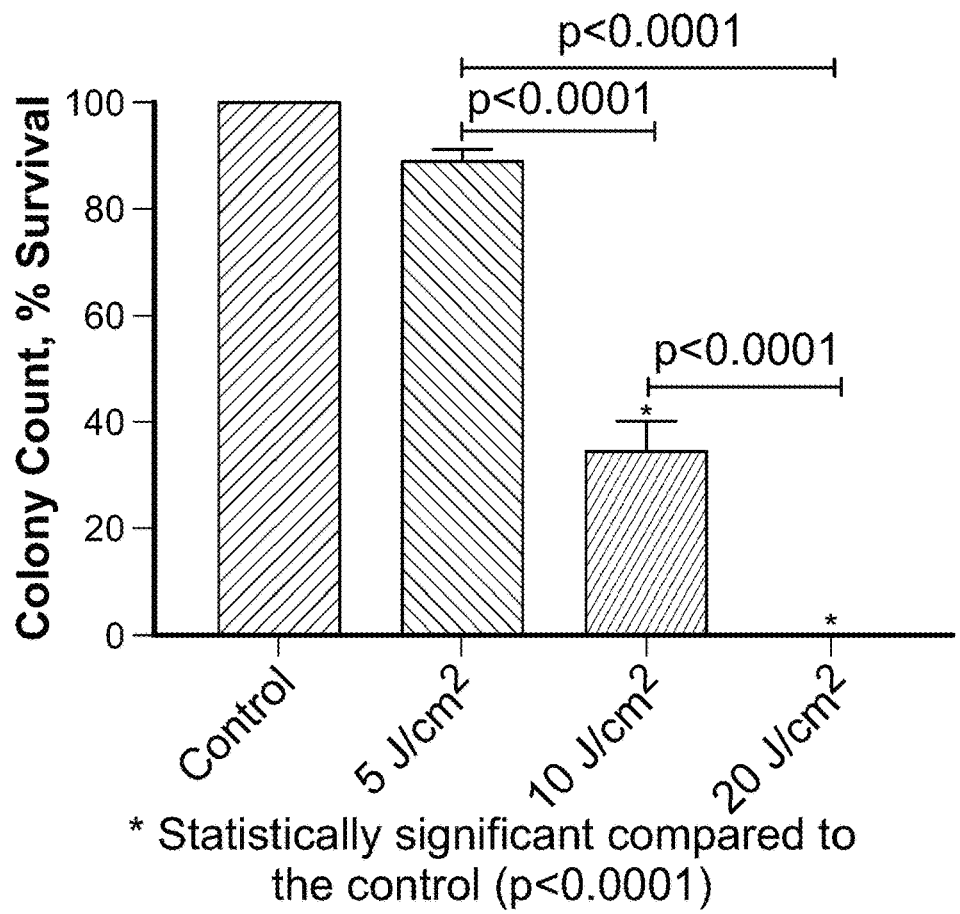
FIG. 10 is a graph depicting *P. acnes* survival when irradiated with 450 nm light at radiant exposures of 5, 10 and 20 J/cm$^2$; average irradiance of 3 mW/cm$^2$; pulsed mode of irradiation (33% duty factor); and multiple irradiation at 0, 4, 24 and 48 hours.

As illustrated in FIG. 10, irradiation of cultures four times (0, 4, 24 and 48 hours) with radiant exposures of 5, 10 and 20 J/cm$^2$ and an average irradiance of 3 mW/cm$^2$ in the 33% DF pulsed mode showed decreases in percent survival when compared to the control, i.e., 89.1%, 34.3% and 0.5%, respectively. The decrease in percent bacterial survival was dose dependent with significant decreases observed between the radiant exposure of 5 and 10 J/cm$^2$, between 5 and 20 J/cm$^2$, and between 10 and 20 J/cm$^2$.

Example 2

A second experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 3 mW/cm$^2$. The pulse duration was 10 microseconds with an off time of 20 microseconds, and a pulse repetition rate of 33 kHz. The bacteria were irradiated four times at 0, 3, 6 and 24 hours with different radiant exposures of 5, 10 and 20 J/cm$^2$.

Figure 11:
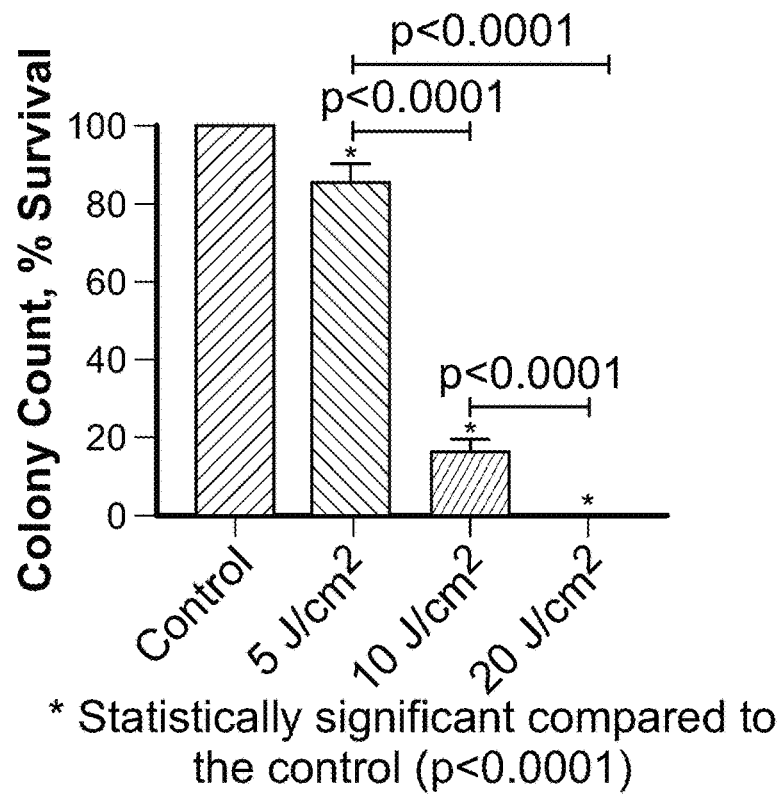
FIG. 11 is a graph depicting *P. acnes* survival when irradiated with 450 nm light at radiant exposures of 5, 10 and 20 J/cm$^2$; average irradiance of 3 mW/cm$^2$; pulsed mode of irradiation (33% duty factor); and multiple irradiation at 0, 3, 6 and 24 hours.

As illustrated in FIG. 11, irradiation of cultures four times (0, 3, 6 and 24 hours) with radiant exposures of 5, 10 and 20 J/cm$^2$ and an average irradiance of 3 mW/cm$^2$ in the 33% DF pulsed mode showed decreases in percent survival when compared to the control, i.e., 85.7%, 16.3% and 0.0%, respectively. The overall decrease in percent survival was higher than that seen in the first example. Again, the decrease in percent bacterial survival was dose dependent with significant decreases observed between the radiant exposure of 5 and 10 J/cm$^2$, between 5 and 20 J/cm$^2$, and between 10 and 20 J/cm$^2$.

Example 3

A third experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 3 mW/cm$^2$. The pulse duration was 10 microseconds with an off time of 20 microseconds, and a pulse repetition rate of 33 kHz. The bacteria were irradiated three times at 0, 3 and 6 hours with different radiant exposures of 5, 10 and 20 J/cm$^2$.

Figure 12:
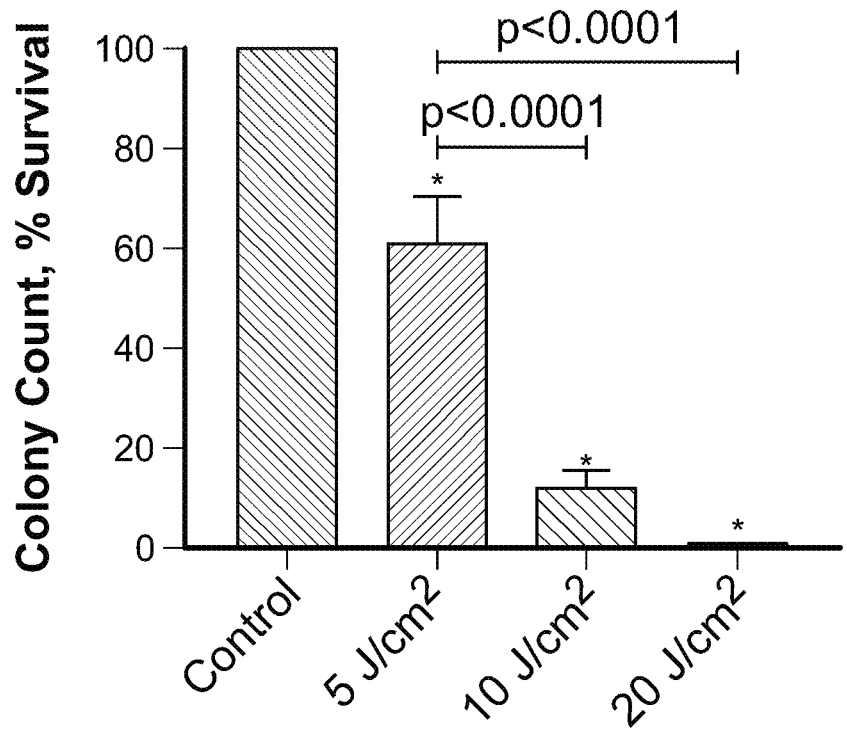
FIG. 12 is a graph depicting *P. acnes* survival when irradiated with 450 nm light at radiant exposures of 5, 10 and 20 J/cm$^2$; average irradiance of 3 mW/cm$^2$; pulsed mode of irradiation (33% duty factor); and multiple irradiation at 0, 3 and 6 hours.

As illustrated in FIG. 12, irradiation of cultures three times using a shorter time interval (0, 3 and 6 hours) with radiant exposures of 5, 10 and 20 J/cm$^2$ and an average irradiance of 3 mW/cm$^2$ in the 33% DF pulsed mode showed decreases in percent survival when compared to the control, i.e., 60.9%, 11.7% and 0.2%, respectively. The decrease in percent bacterial survival was dose dependent with significant decreases observed between the radiant exposure of 5 and 10 J/cm$^2$, between 5 and 20 J/cm$^2$, and between 10 and 20 J/cm$^2$.

Example 4

A fourth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 3 mW/cm$^2$. The pulse duration was 10 microseconds with an off time of 20 microseconds, and a pulse repetition rate of 33 kHz. The bacteria were irradiated nine times at 0, 3, 6, 24, 27, 30, 48, 51 and 54 hours with a radiant exposure of 5 J/cm$^2$.

Figure 13:
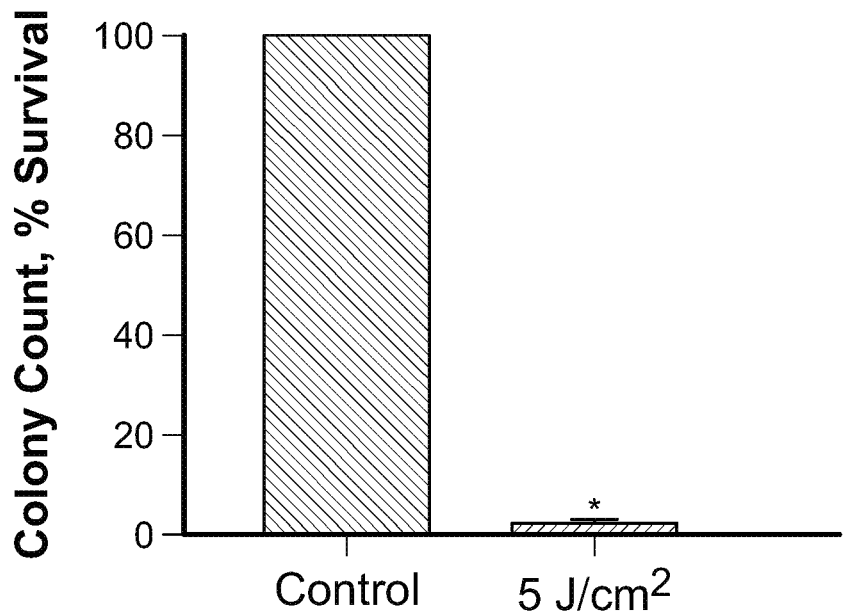
FIG. 13 is a graph depicting *P. acnes* survival when irradiated with 450 nm light at a radiant exposure of 5 J/cm$^2$; average irradiance of 3 mW/cm$^2$; pulsed mode of irradiation (33% duty factor); and multiple irradiation at 0, 3, 6, 24, 27, 30, 48, 51 and 54 hours.

As illustrated in FIG. 13, a change in the irradiation schedule to three times per day, every three hours over the course of three days for a total of nine times (0, 3, 6, 24, 27, 30, 48, 51 and 54 hours) with a radiant exposure of 5 J/cm$^2$ and an average irradiance of 3 mW/cm$^2$ in the 33% DF pulsed mode showed a significant decrease in percent survival when compared to the control, i.e., 2.57%.

Example 5

A fifth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 3 mW/cm$^2$. The pulse duration was 10 microseconds with an off time of 20 microseconds, and a pulse repetition rate of 33 kHz. The bacteria were irradiated twelve times at 0, 3, 6, 24, 27, 30, 48, 51, 54, 72, 75 and 78 hours with a radiant exposure of 5 J/cm$^2$.

Figure 14:
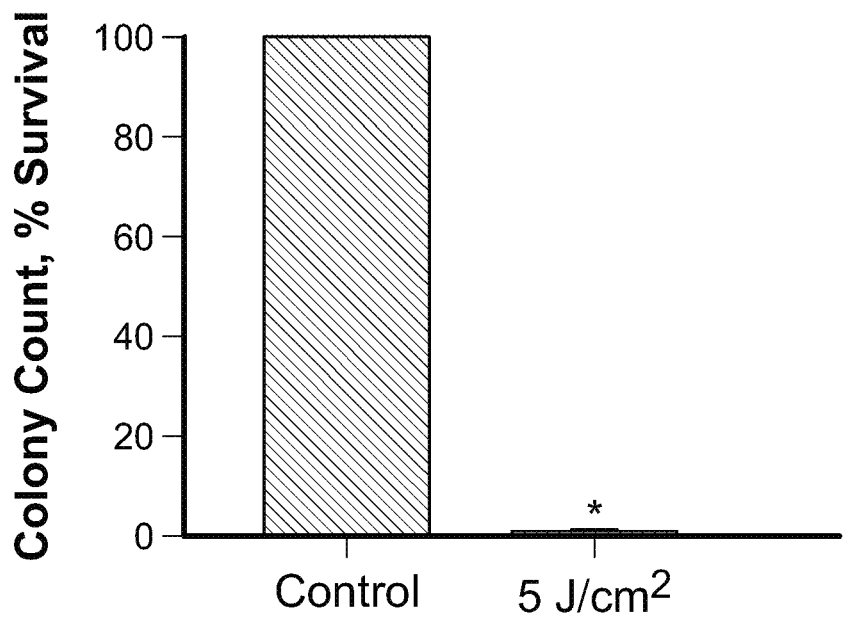
FIG. 14 is a graph depicting *P. acnes* survival when irradiated with 450 nm light at a radiant exposure of 5 J/cm$^2$; average irradiance of 3 mW/cm$^2$; pulsed mode of irradiation (33% duty factor); and multiple irradiation at 0, 3, 6, 24, 27, 30, 48, 51, 54, 72, 75 and 78 hours.

As illustrated in FIG. 14, a change in the irradiation schedule to three times per day, every three hours over the course of four days for a total of twelve times (0, 3, 6, 24, 27, 30, 48, 51, 54, 72, 75 and 78 hours) with a radiant exposure of 5 J/cm$^2$ and an average irradiance of 3 mW/cm$^2$ in the 33% DF pulsed mode showed a significant decrease in percent survival when compared to the control, i.e., 1.13%. The overall decrease in percent survival was higher than that seen in the fourth example when bacteria were irradiated over the course of three days (with all other parameters being the same).

Example 6

A sixth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm$^2$. The pulse duration was 10 microseconds with an off time of 20 microseconds, and a pulse repetition rate of 33 kHz. The bacteria were irradiated twelve times at 0, 3, 6, 24, 27, 30, 48, 51, 54, 72, 75 and 78 hours with a radiant exposure of 5 J/cm$^2$.

Figure 15:
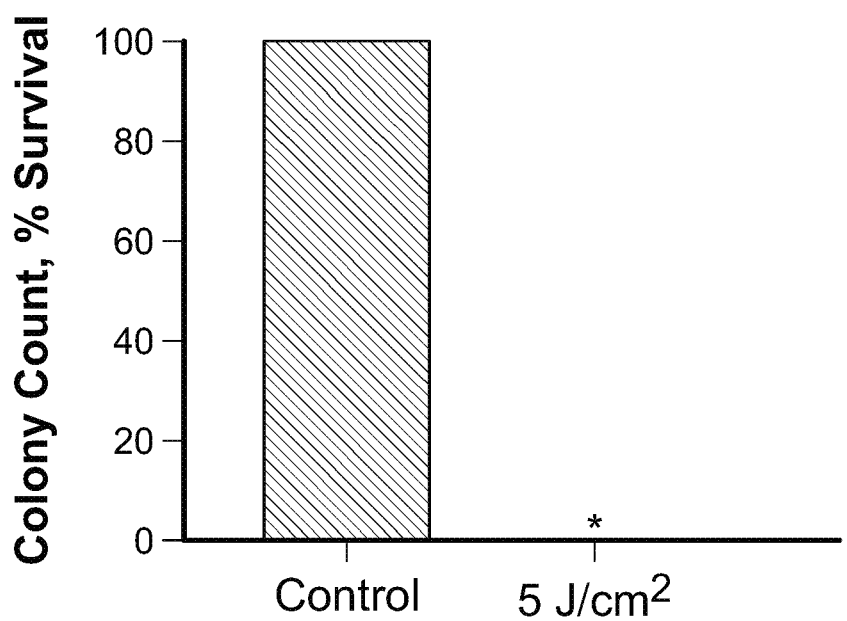
FIG. 15 is a graph depicting *P. acnes* survival when irradiated with 450 nm light at a radiant exposure of 5 J/cm$^2$; average irradiance of 2 mW/cm$^2$; pulsed mode of irradiation (33% duty factor); and multiple irradiation at 0, 3, 6, 24, 27, 30, 48, 51, 54, 72, 75 and 78 hours.

As illustrated in FIG. 15, the irradiation of bacteria three times per day, every three hours over the course of four days for a total of twelve times (0, 3, 6, 24, 27, 30, 48, 51, 54, 72, 75 and 78 hours) with a radiant exposure of 5 J/cm$^2$ and a change in the average irradiance to 2 mW/cm$^2$ in the 33% DF pulsed mode showed a complete bacterial eradication when compared to the control, i.e., 0.0%. The overall decrease in percent survival was slightly higher than that seen in the fifth example when the average irradiance was 3 mW/cm$^2$ (with all other parameters being the same).

Example 7

A seventh experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm$^2$. The pulse duration was 10 microseconds with an off time of 20 microseconds, and a pulse repetition rate of 33 kHz. The bacteria were irradiated nine times at 0, 3, 6, 24, 27, 30, 48, 51 and 54 hours with a radiant exposure of 5 J/cm$^2$.

Figure 16:
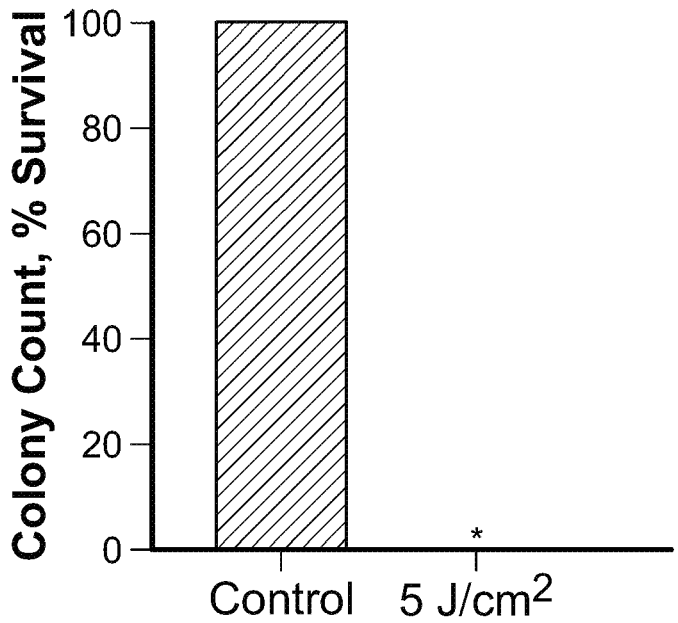
FIG. 16 is a graph depicting *P. acnes* survival when irradiated with 450 nm light at a radiant exposure of 5 J/cm$^2$; average irradiance of 2 mW/cm$^2$; pulsed mode of irradiation (33% duty factor); and multiple irradiation at 0, 3, 6, 24, 27, 30, 48, 51 and 54 hours.

As illustrated in FIG. 16, the irradiation of bacteria three times per day, every three hours over the course of three days for a total of nine times (0, 3, 6, 24, 27, 30, 48, 51 and 54 hours) with a radiant exposure of 5 J/cm$^2$ and an average irradiance of 2 mW/cm$^2$ in the 33% DF pulsed mode showed a complete bacterial eradication when compared to the control, i.e., 0.0%. The overall decrease in percent survival was the same as that seen in the sixth example when the irradiation was applied over the course of four days for a total of twelve times (with all other parameters being the same).

Example 8

An eighth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm$^2$. The pulse duration was 10 microseconds with an off time of 20 microseconds, and a pulse repetition rate of 33 kHz. The bacteria were irradiated eight times at 0, 3, 24, 27, 48, 51, 72 and 75 hours with a radiant exposure of 3.6 J/cm$^2$.

Figure 17:
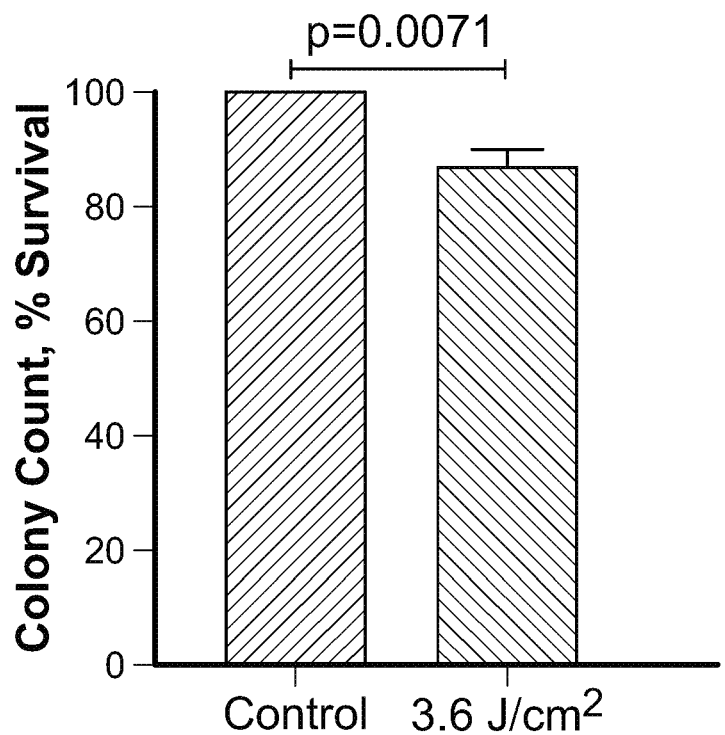
FIG. 17 is a graph depicting *P. acnes* survival when irradiated with 450 nm light at a radiant exposure of 3.6 J/cm$^2$; average irradiance of 2 mW/cm$^2$; pulsed mode of irradiation (33% duty factor); and multiple irradiation at 0, 3, 24, 27, 48, 51, 72 and 75 hours.

As illustrated in FIG. 17, the irradiation of bacteria two times per day, every three hours over the course of four days for a total of eight times (0, 3, 24, 27, 48, 51, 72 and 75 hours) with a lower radiant exposure of 3.6 J/cm$^2$ and an average irradiance of 2 mW/cm$^2$ in the 33% DF pulsed mode showed a slight decrease in percent survival when compared to the control, i.e., 86.9%, which is significantly higher than that seen in the seventh example when the radiant exposure was 5 J/cm$^2$ and the irradiation was applied three times per day (with all other parameters being the same).

Example 9

A ninth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm$^2$. The pulse duration was 10 microseconds with an off time of 20 microseconds, and a pulse repetition rate of 33 kHz. The bacteria were irradiated ten times at 0, 3, 24, 27, 48, 51, 72, 75, 96, and 99 hours with a radiant exposure of 3.6 J/cm$^2$.

Figure 18:
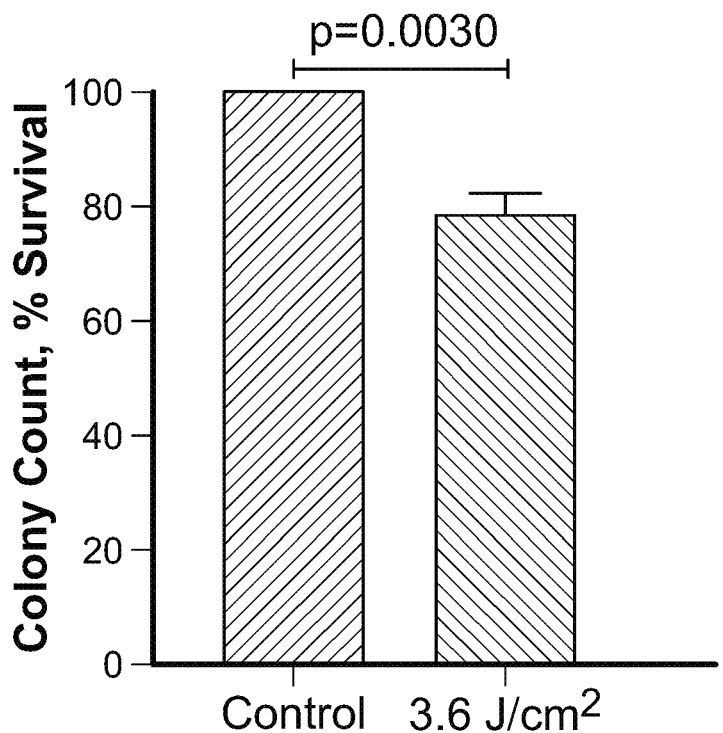
FIG. 18 is a graph depicting *P. acnes* survival when irradiated with 450 nm light at a radiant exposure of 3.6 J/cm$^2$; average irradiance of 2 mW/cm$^2$; pulsed mode of irradiation (33% duty factor); and multiple irradiation at 0, 3, 24, 27, 48, 51, 72, 75, 96 and 99 hours.

As illustrated in FIG. 18, the irradiation of bacteria two times per day, every three hours over the course of five days for a total of ten times (0, 3, 24, 27, 48, 51, 72, 75, 96, and 99 hours) with a radiant exposure of 3.6 J/cm$^2$ and an average irradiance of 2 mW/cm$^2$ in the 33% DF pulsed mode showed a decrease in percent survival when compared to the control, i.e., 78.9%, which is just slightly lower than that seen in the eighth example when the irradiation was applied over the course of four days (with all other parameters being the same).

Example 10

A tenth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm². The pulse duration was 10 microseconds with an off time of 20 microseconds, and a pulse repetition rate of 33 kHz. The bacteria were irradiated twelve times at 0, 3, 6, 24, 27, 30, 48, 51, 54, 72, 75 and 78 hours with a radiant exposure of 3.6 J/cm².

Figure 19:
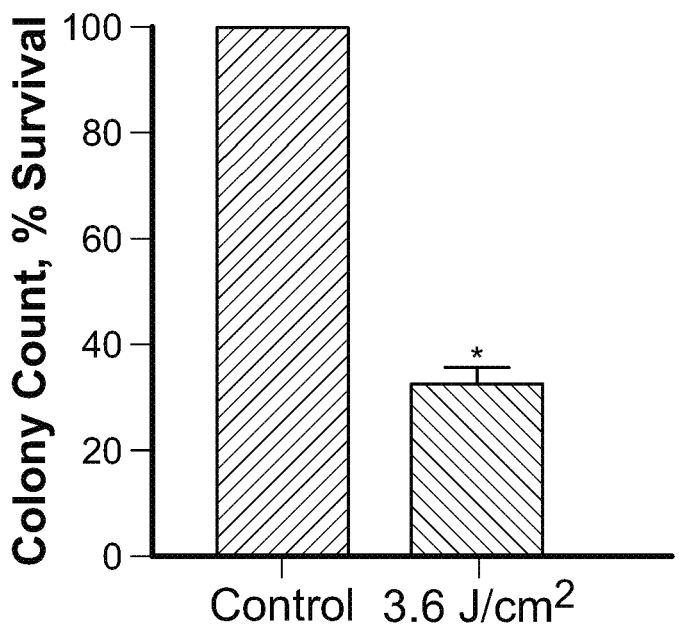
FIG. 19 is a graph depicting *P. acnes* survival when irradiated with 450 nm light at a radiant exposure of 3.6 J/cm$^2$; average irradiance of 2 mW/cm$^2$; pulsed mode of irradiation (33% duty factor); and multiple irradiation at 0, 3, 6, 24, 27, 30, 48, 51, 54, 72, 75 and 78 hours.

As illustrated in FIG. 19, the irradiation of bacteria three times per day, every three hours over the course of four days for a total of twelve times (0, 3, 6, 24, 27, 30, 48, 51, 54, 72, 75 and 78 hours) with a radiant exposure of 3.6 J/cm² and an average irradiance of 2 mW/cm² in the 33% DF pulsed mode showed a decrease in percent survival when compared to the control, i.e., 32.6%, which is lower than that seen in the eighth and ninth examples.

Example 11

An eleventh experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm². The pulse duration was 10 microseconds with an off time of 20 microseconds, and a pulse repetition rate of 33 kHz. The bacteria were irradiated nine times at 0, 3, 6, 24, 27, 30, 48, 51 and 54 hours with a radiant exposure of 5 J/cm².

Figure 20:
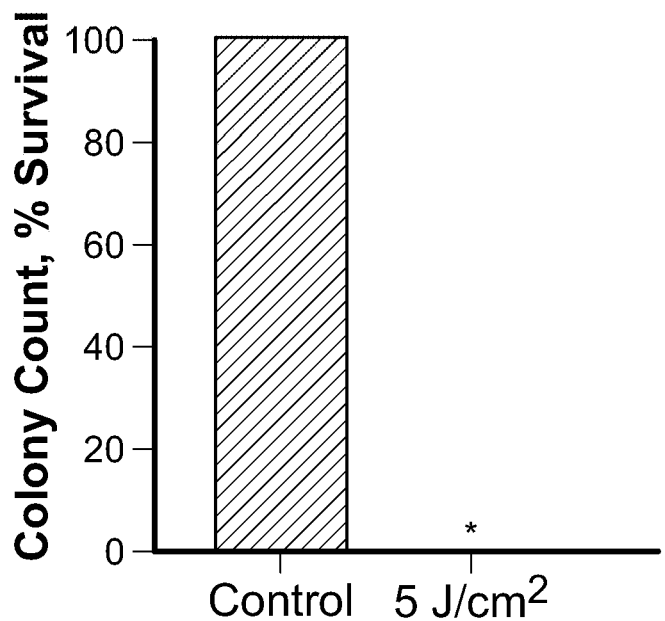
FIG. 20 is a graph depicting *P. acnes* survival when irradiated with 450 nm light at a radiant exposure of 5 J/cm$^2$; average irradiance of 2 mW/cm$^2$; pulsed mode of irradiation (33% duty factor); and multiple irradiation at 0, 3, 6, 24, 27, 30, 48, 51 and 54 hours.

As illustrated in FIG. 20, the irradiation of bacteria three times per day, every three hours over the course of three days for a total of nine times (0, 3, 6, 24, 27, 30, 48, 51 and 54 hours) with a radiant exposure of 5 J/cm² and an average irradiance of 2 mW/cm² in the 33% DF pulsed mode showed a complete bacterial eradication when compared to the control, i.e., 0.0%. This experiment confirmed the data from the seventh experiment (see Example 7).

Example 12

A twelfth experiment involved culturing *P. acnes* and illuminating the bacteria with the 450 nm lighted substrate shown in FIG. 22. The lighted substrate was set to operate in 33% DF pulsed mode, as described below, and driven with a constant current source. The average irradiance was 2 mW/cm². The pulse duration was 10 microseconds with an off time of 20 microseconds, and a pulse repetition rate of 33 kHz. The bacteria were irradiated nine times at 0, 3, 6, 24, 27, 30, 48, 51 and 54 hours with a radiant exposure of 3.6 J/cm².

Figure 21:
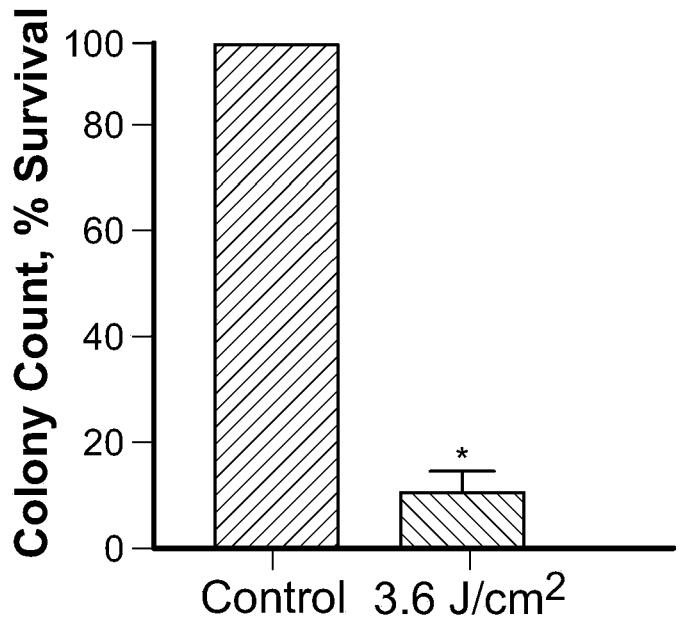
FIG. 21 is a graph depicting *P. acnes* survival when irradiated with 450 nm light at a radiant exposure of 3.6 J/cm$^2$; average irradiance of 2 mW/cm$^2$; pulsed mode of irradiation (33% duty factor); and multiple irradiation at 0, 3, 6, 24, 27, 30, 48, 51 and 54 hours.

As illustrated in FIG. 21, the irradiation of bacteria three times per day, every three hours over the course of three days for a total of nine times (0, 3, 6, 24, 27, 30, 48, 51 and 54 hours) with a radiant exposure of 3.6 J/cm² and an average irradiance of 2 mW/cm² in the 33% DF pulsed mode showed a significant decrease in percent survival when compared to the control, i.e., 11.7%. Although the percentage survival was low, it was still higher than that seen in the eleventh example when the radiant exposure was 5 J/cm² (with all other parameters being the same).

Summary

Further testing was performed using light patches that emit pulsed blue light at a 33% duty cycle. The various protocols tested showed effective reduction in bacteria growth. Testing using irradiation intervals of 3 hours proved to be more efficient than irradiation intervals of 4 hours. It is believed that such observed efficiency may be due in part to targeting the bacteria at the appropriate time during the replication cycle or due to porphyrin depletion/replenishing mechanisms in the bacteria.

Irradiation protocols were optimized to yield 100% bacterial suppression of 1×10⁶ CFU/mL *P. acnes* cultures. Optimal bacterial suppression of 100% was attained (i) when cultures were irradiated at 0, 3, 6 and 24 hours with a radiant exposure of 20 J/cm² and an average irradiance of 3 mW/cm² (see Example 2), (ii) when cultures were irradiated three times per day, every three hours over the course of four days for a total of twelve times (0, 3, 6, 24, 27, 30, 48, 51, 54, 72, 75 and 78 hours) with a radiant exposure of 5 J/cm² and an average irradiance to 2 mW/cm² (see Example 6), and (iii) when cultures were irradiated three times per day, every three hours over the course of three days for a total of nine times (0, 3, 6, 24, 27, 30, 48, 51 and 54 hours) with a radiant exposure of 5 J/cm² and an average irradiance of 2 mW/cm² (see Example 11).

One skilled in the art will appreciate that the present invention allows for improved device performance with reduced battery requirements, a substantial reduction in treatment time, and improved patient safety due to a significant reduction in heat and optical hazard.

IV. In Vitro Testing of GBS Cultures Supplemented with Porphyrins to Obtain Bacterial Suppression with Light Irradiation The results described above revealed that pulsed blue light was effective in suppressing bacteria growth for *P. acnes*, which synthesizes the photoactive molecule porphyrin. However, some bacteria such as Group B *Streptococcus* (GBS) do not synthesize a sufficient amount of porphyrin or other photoactive molecules, in which case a photosensitizer is needed to function as a photoreceptor for the pulsed blue light. Thus, further testing was performed to assess GBS bacterial suppression when supplemented with exogenous porphyrins (either protoporphyrin IX (PPIX) or coproporphyrin III (CP III)) and irradiated with pulsed blue light using printed LED flexible lamps.

Study 1: GBS Supplemented with Different Concentrations of Porphyrins

GBS wild type strain COH1 was added to 3 mL of Todd Hewitt broth and grown aerobically overnight at 37° C. From the overnight cultures, 500 uL of GBS was added to fresh Todd Hewitt broth and grown logarithmically at 37° C. until reaching a concentration of 10⁸ CFU/mL. The culture was then centrifuged at 1300 rpm for three minutes, the supernatant was removed and discarded, and 1 mL of fresh Todd Hewitt broth was added. Serial dilutions of NaCl were made to obtain a suspension of GBS diluted to a concentration of 1×10⁴ CFU/mL. The GBS were streaked onto Todd Hewitt agar plates both with and without the addition of diluted porphyrins (different concentrations of PPIX or CP III).

Some of the plates were irradiated in a chamber using the 450 nm lighted substrate shown in FIG. 22. The lighted substrate was set to operate in 33% DF pulsed mode and driven with a constant current source. The average irradiance was 3 mW/cm². The pulse duration was 10 microseconds with an off time of 20 microseconds, and a pulse repetition rate of 33 kHz. The plates subject to light treatment were irradiated three times at 0, 72 and 144 hours with a radiant exposure of 7.56 J/cm² during each irradiation session (i.e., each irradiation session was 42 minutes with an incubation period there between of 30 minutes).

After irradiation protocols were completed, the plates were placed upside down in the anaerobic chamber and incubated at 37° C. for 24 hours. The plates were photographed, colonies counted and statistics of percent survival recorded.

Example 1

In a first experiment, the GBS were assigned to six experimental groups: (1) GBS only (control); (2) GBS and light; (3) GBS supplemented with 0.05 mg/mL PPIX; (4) GBS supplemented with 0.002 mg/mL PPIX and light; (5) GBS supplemented with 0.02 mg/mL PPIX and light; and (6) GBS supplemented with 0.05 mg/mL PPIX and light. The results are shown in FIG. 33.

Figure 33:
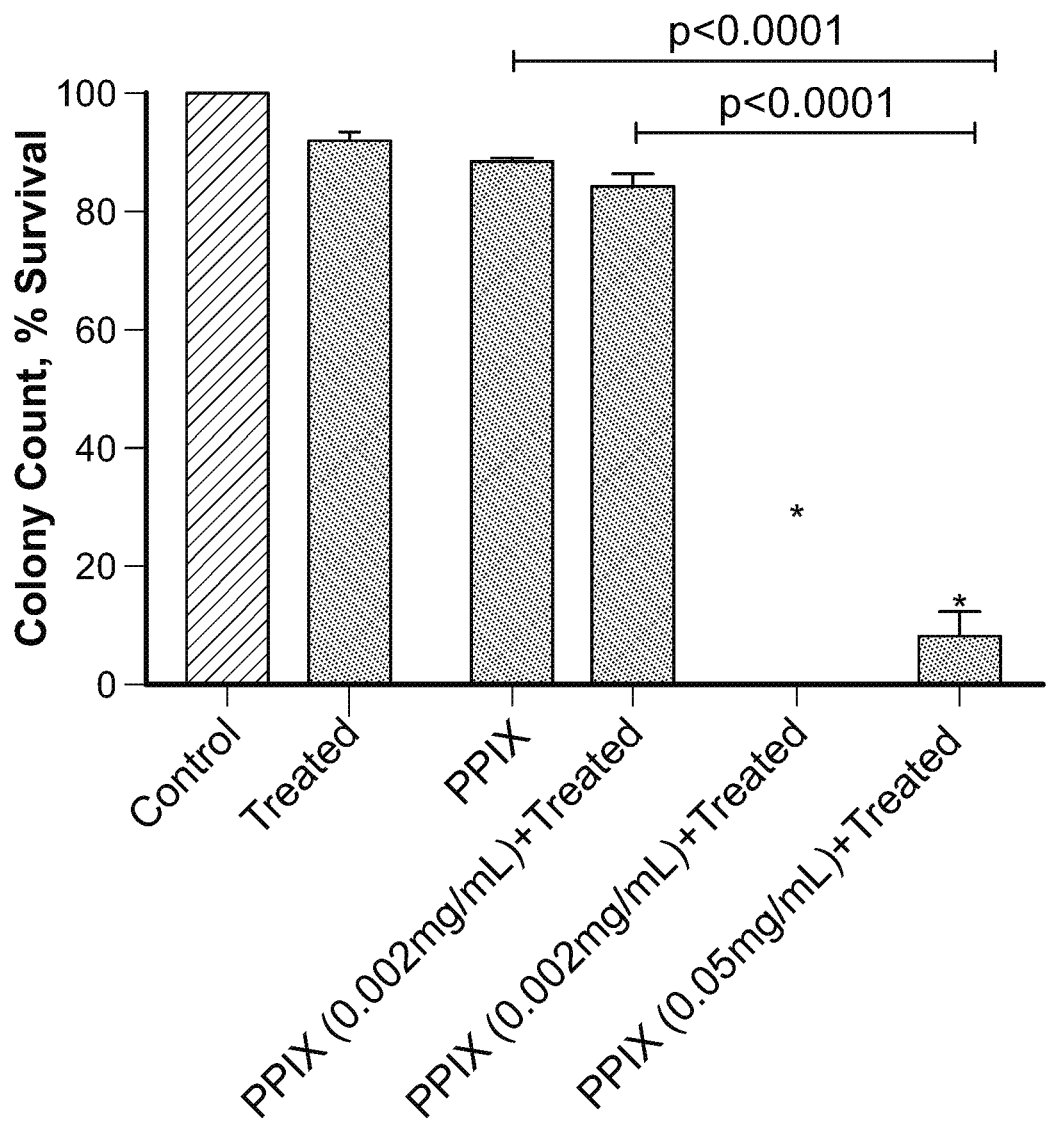
FIGS. 33 and 34 are graphs depicting GBS survival for different combinations of 0.002, 0.02 or 0.05 mg/mL PPIX supplementation and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 33, irradiation of GBS without the addition of any PPIX showed a minimal decrease in percent GBS survival when compared to the control, i.e., approximately 87%, which demonstrates that GBS does not synthesize a sufficient amount of porphyrin. Also, GBS supplemented with 0.05 mg/mL PPIX, but without any irradiation, did not show much decrease in percent GBS survival when compared to the control, i.e., approximately 85%. In addition, irradiation of GBS supplemented with 0.002 mg/mL PPIX did not show much decrease in percent GBS survival when compared to the control, i.e., approximately 83%, which demonstrates that the concentration of PPIX was too low. However, irradiation of GBS supplemented with 0.02 mg/mL PPIX and 0.05 mg/mL PPIX showed significant decreases in percent GBS survival when compared to the control, i.e., 0% and 3%, respectively. Thus, the decrease in percent GBS survival was dependent on the concentration of PPIX added to the GBS prior to irradiation.

Example 2

In a second experiment conducted separately, and with observed slight decrease in CFU/mL, the GBS were assigned to six experimental groups: (1) GBS only (control); (2) GBS and light; (3) GBS supplemented with 0.05 mg/mL PPIX; (4) GBS supplemented with 0.002 mg/mL PPIX and light; (5) GBS supplemented with 0.02 mg/mL PPIX and light; and (6) GBS supplemented with 0.05 mg/mL PPIX and light. The results are shown in FIG. 34.

Figure 34:
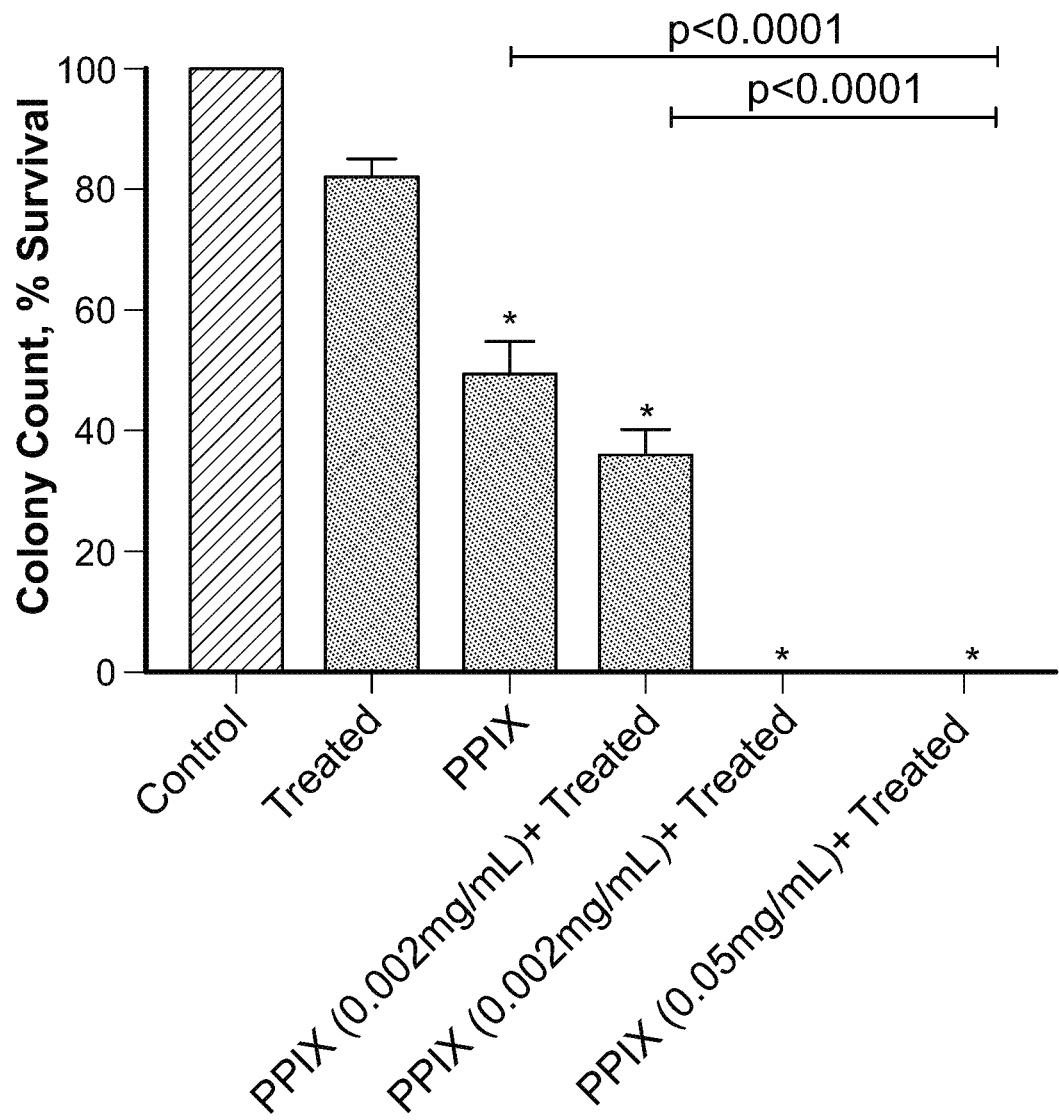

As can be seen in FIG. 34, irradiation of GBS without the addition of any PPIX showed a small decrease in percent GBS survival when compared to the control, i.e., approximately 81%, which again demonstrates that GBS does not synthesize a sufficient amount of porphyrin. GBS supplemented with 0.05 mg/mL PPIX, but without any irradiation, showed some decrease in percent GBS survival when compared to the control, i.e., approximately 50%. In addition, irradiation of GBS supplemented with 0.002 mg/mL PPIX showed even more decrease in percent GBS survival when compared to the control, i.e., approximately 37%. Further, irradiation of GBS supplemented with 0.02 mg/mL PPIX and 0.05 mg/mL PPIX showed complete bacterial kill, i.e., 0% GBS survival. Thus, the decrease in percent GBS survival was dependent on the concentration of PPIX added to the GBS prior to irradiation, and also on the number of CFU/mL.

Example 3

In a third experiment, the GBS were assigned to five experimental groups: (1) GBS only (control); (2) GBS and light; (3) GBS supplemented with 0.05 mg/mL CP III; (4) GBS supplemented with 0.002 mg/mL CP III and light, and (5) GBS supplemented with 0.05 mg/mL CP III and light. Because the CP III was solubilized in ethanol, two additional experimental groups were included to test whether the quantity of ethanol used as a solvent had any significant effect on bacterial growth suppression: (6) ethanol only and (7) ethanol and light. The results are shown in FIG. 35.

Figure 35:
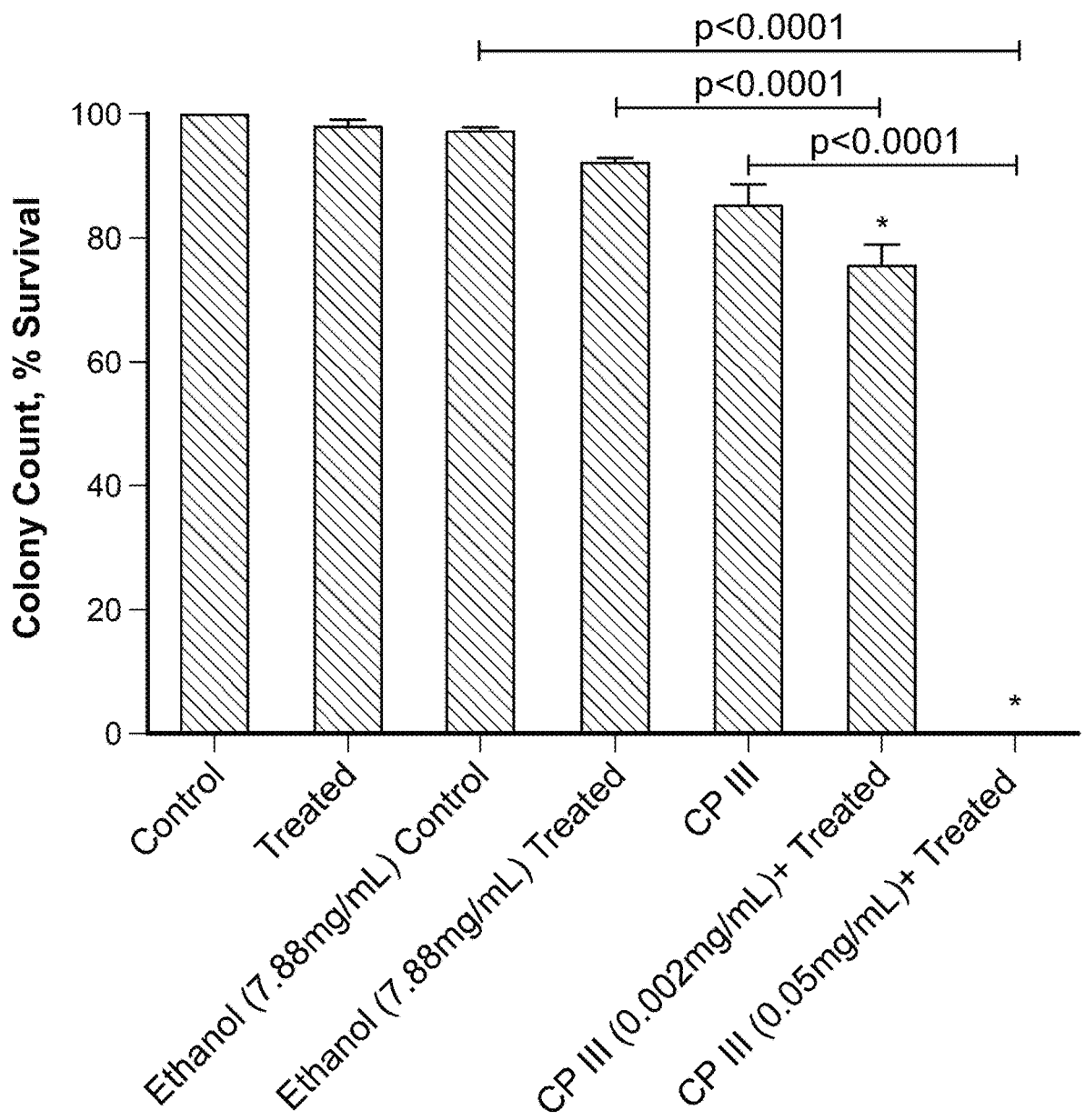
FIG. 35 is a graph depicting GBS survival for different combinations of 0.002 or 0.05 mg/mL CP III supplementation and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 35, irradiation of GBS without the addition of any CP III showed a minimal decrease in percent GBS survival when compared to the control, i.e., approximately 98%, which demonstrates that GBS does not synthesize a sufficient amount of porphyrin. Also, GBS supplemented with 0.05 mg/mL CP III, but without any irradiation, did not show much decrease in percent GBS survival when compared to the control, i.e., approximately 84%. In addition, irradiation of GBS supplemented with 0.002 mg/mL CP III did not show much decrease in percent GBS survival when compared to the control, i.e., approximately 78%, which demonstrates that the concentration of CP III was too low. However, irradiation of GBS supplemented with 0.05 mg/mL CP III showed complete bacterial kill, i.e., 0% GBS survival. Thus, the decrease in percent GBS survival was dependent on the concentration of CP III added to the GBS prior to irradiation. It should also be noted that ethanol did not have any significant contribution to the observed suppressive effect.

Example 4

In a fourth experiment, the GBS were assigned to five experimental groups: (1) GBS only (control); (2) GBS and light; (3) GBS supplemented with 0.02 mg/mL CP III; (4) GBS supplemented with 0.002 mg/mL CP III and light; and (5) GBS supplemented with 0.05 mg/mL CP III and light. Because the CP III was solubilized in ethanol, two additional experimental groups were included to test whether the quantity of ethanol used as a solvent had any significant effect on bacterial growth suppression: (6) ethanol only and (7) ethanol and light. The results are shown in FIG. 36.

Figure 36:
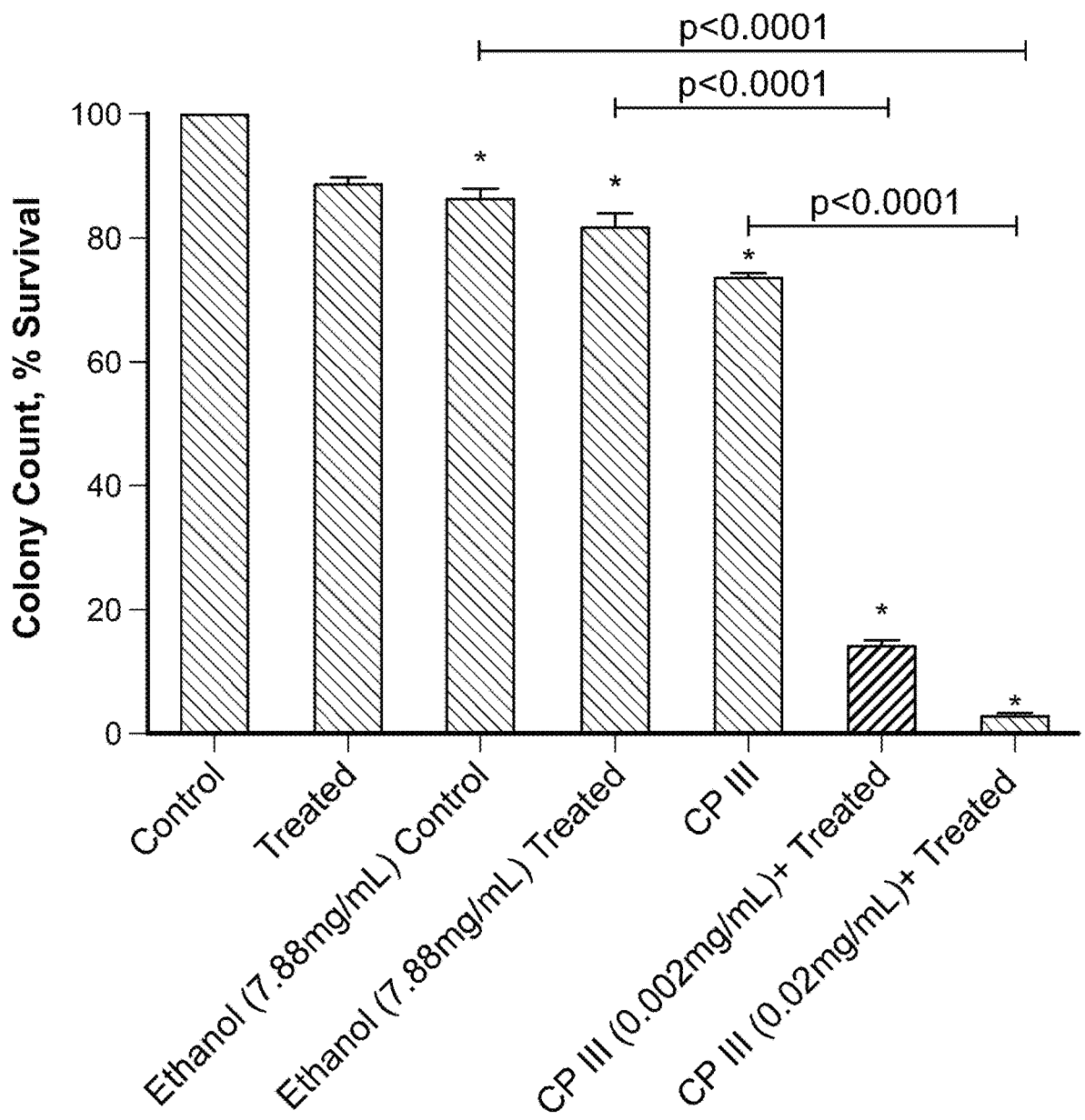
FIG. 36 is a graph depicting GBS survival for different combinations of 0.002 or 0.02 mg/mL CP II supplementation and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 36, irradiation of GBS without the addition of any CP III showed a minimal decrease in percent GBS survival when compared to the control, i.e., approximately 90%, which again demonstrates that GBS does not synthesize a sufficient amount of porphyrin. Also, GBS supplemented with 0.02 mg/mL CP III, but without any irradiation, showed a small decrease in percent GBS survival when compared to the control, i.e., approximately 74%. In addition, irradiation of GBS supplemented with 0.002 mg/mL CP III showed a significant decrease in percent GBS survival when compared to the control, i.e., approximately 17%. Further, irradiation of GBS supplemented with 0.05 mg/mL CP III showed complete bacterial kill, i.e., 0% GBS survival. Thus, the decrease in percent GBS survival was dependent on the concentration of CP III added to the GBS prior to irradiation, and also on the number of CFU/mL. It should also be noted that ethanol did not have any significant contribution to the observed suppressive effect.

Study 2: GBS Supplemented with Porphyrins with Incubation after Supplementation

GBS wild type strain COH1 was added to 3 mL of Todd Hewitt broth and grown aerobically overnight at 37° C. From the overnight cultures, 500 uL of GBS was added to fresh Todd Hewitt broth and grown logarithmically at 37° C. until reaching a concentration of 108 CFU/mL. The culture was then centrifuged at 1300 rpm for three minutes, the supernatant was removed and discarded, and 1 mL of fresh Todd Hewitt broth was added.

The culture was then split into three Eppendorf tubes—a first tube for GBS and second and third tubes for GBS with diluted porphyrins used for incubation. Diluted porphyrins (PPIX or CP III) were added into the second and third tubes and incubated for 30 minutes at 37° C. The third tube was then washed three times with phosphate-buffered saline (PBS) and centrifuged at 1300 rpm for three minutes, and the supernatant was removed and discarded. Serial dilutions of NaCl were made to obtain a suspension of GBS diluted to a concentration of $1\times10^1$ CFU/mL. The GBS were streaked onto Todd Hewitt agar plates.

Some of the plates were irradiated in a chamber using the 450 nm lighted substrate shown in FIG. 22. The lighted substrate was set to operate in 33% DF pulsed mode and driven with a constant current source. The average irradiance was 3 mW/cm$^2$. The pulse duration was 10 microseconds with an off time of 20 microseconds, and a pulse repetition rate of 33 kHz. The plates subject to light treatment were irradiated three times at 0, 72 and 144 hours with a radiant exposure of 7.56 J/cm$^2$ during each irradiation session (i.e., each irradiation session was 42 minutes with an incubation period therebetween of 30 minutes).

After irradiation protocols were completed, the plates were placed upside down in the anaerobic chamber and incubated at 37° C. for 24 hours. The plates were photographed, colonies counted and statistics of percent survival recorded.

Example 5

In a fifth experiment, the GBS were assigned to six experimental groups: (1) GBS only (control); (2) GBS and light; (3) GBS supplemented with 0.02 mg/mL PPIX (incubated); (4) GBS supplemented with 0.02 mg/mL PPIX (incubated) and light; (5) GBS supplemented with 0.02 mg/mL PPIX (incubated and washed); and (6) GBS supplemented with 0.02 mg/mL PPIX (incubated and washed) and light. The results are shown in FIG. 37.

Figure 37:
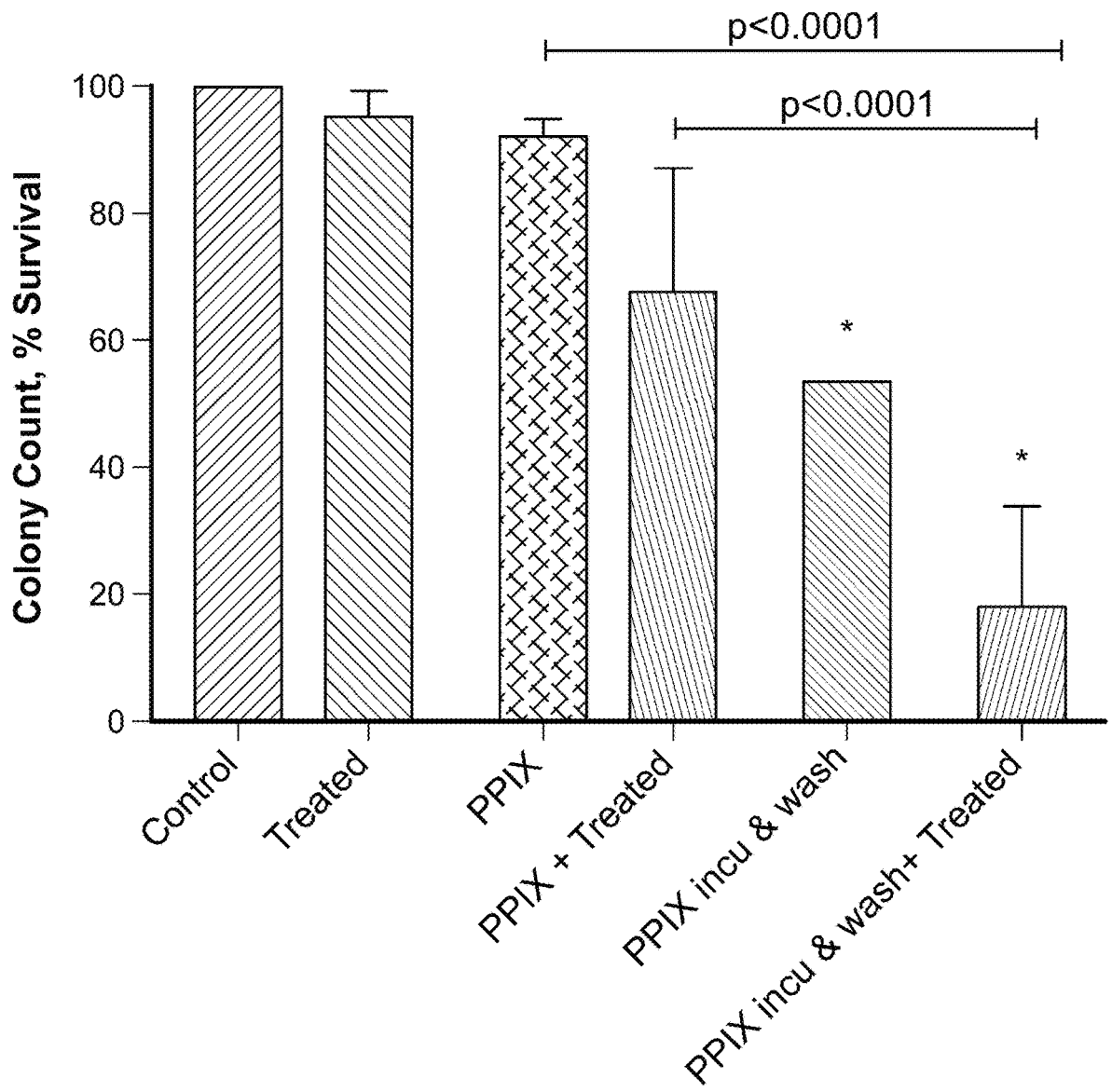
FIGS. 37 and 38 are graphs depicting GBS survival for different combinations of 0.02 mg/mL PPIX supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 37, irradiation of GBS without the addition of any PPIX showed a minimal decrease in percent GBS survival when compared to the control, i.e., approximately 97%, which demonstrates that GBS does not synthesize a sufficient amount of porphyrin. Also, GBS supplemented with 0.02 mg/mL PPIX (incubated), but without any irradiation, did not show much decrease in percent GBS survival when compared to the control, i.e., approximately 92%. In addition, irradiation of GBS supplemented with 0.02 mg/mL PPIX (incubated) showed a small decrease in percent GBS survival when compared to the control, i.e., approximately 68%. This result is different than those seen in FIGS. 33 and 34 because the bacteria was incubated at 37° C. for approximately thirty minutes before irradiation, which gives them more time to grow, hence starting with an overall increased CFU/mL compared to Examples 1 and 2 where irradiation was commenced immediately after dilutions were made. This is reflected in the higher percent of remnant colonies obtained in this experiment. GBS supplemented with 0.02 mg/mL PPIX (incubated and washed) showed some decrease in percent GBS survival when compared to the control, i.e., approximately 92%. It is believed that there is a slight decrease in percent GBS survival because PPIX may have some minimal suppressive effects that may be concentration dependent. Further, irradiation of GBS supplemented with 0.02 mg/mL PPIX (incubated and washed) showed a significant decrease in percent GBS survival when compared to the control, i.e., approximately 18%.

Overall, the decrease in percent GBS survival was greatest for GBS supplemented with PPIX that was incubated and washed prior to irradiation, which suggests that a sufficient quantity of PPIX was internalized into the GBS during the incubation period. It should be noted that the percent GBS survival for GBS supplemented with PPIX that was incubated prior to irradiation was greater than the percent GBS survival for GBS supplemented with PPIX that was incubated and washed prior to irradiation. This difference is believed to be caused by the fact that incubation with porphyrin has some minimal effect on bacterial survival and, thus, it is likely that more dead bacteria will be washed during the washing step of the incubated sample resulting in a reduced starting CFU/mL.

Example 6

Figure 38:
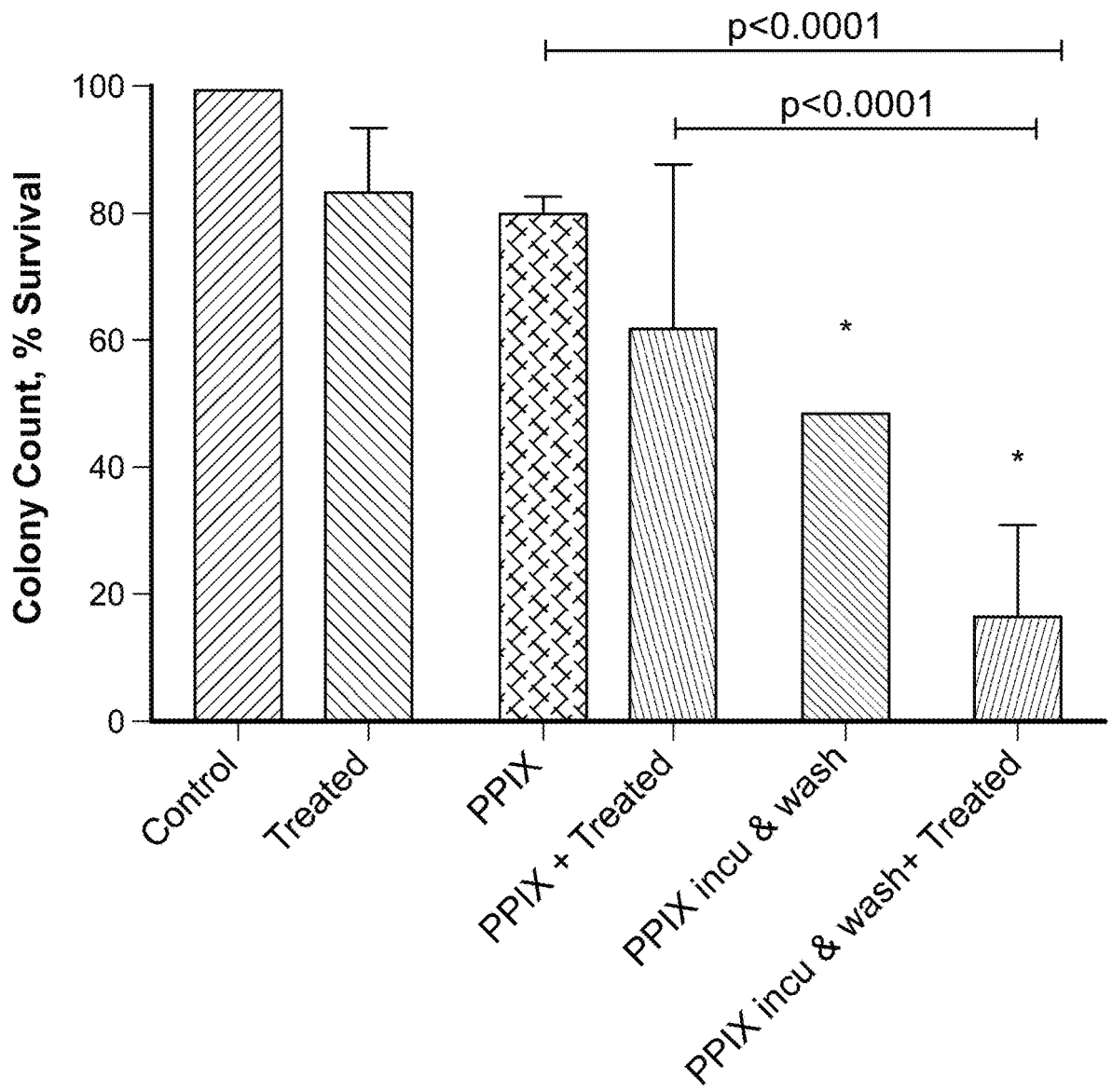

In a sixth experiment, the GBS were assigned to six experimental groups: (1) GBS only (control); (2) GBS and light; (3) GBS supplemented with 0.02 mg/mL PPIX (incubated); (4) GBS supplemented with 0.02 mg/mL PPIX (incubated) and light; (5) GBS supplemented with 0.02 mg/mL PPIX (incubated and washed); and (6) GBS supplemented with 0.02 mg/mL PPIX (incubated and washed) and light. The results are shown in FIG. 38. It should be noted that the results for Example 6 are similar to those of Example 5, which is indicative of the reproducibility of the data.

Example 7

In a seventh experiment, the GBS were assigned to six experimental groups: (1) GBS only (control); (2) GBS and light; (3) GBS supplemented with 0.05 mg/mL PPIX (incubated); (4) GBS supplemented with 0.05 mg/mL PPIX (incubated) and light; (5) GBS supplemented with 0.05 mg/mL PPIX (incubated and washed); and (6) GBS supplemented with 0.05 mg/mL PPIX (incubated and washed)) and light. The results are shown in FIG. 39.

Figure 39:
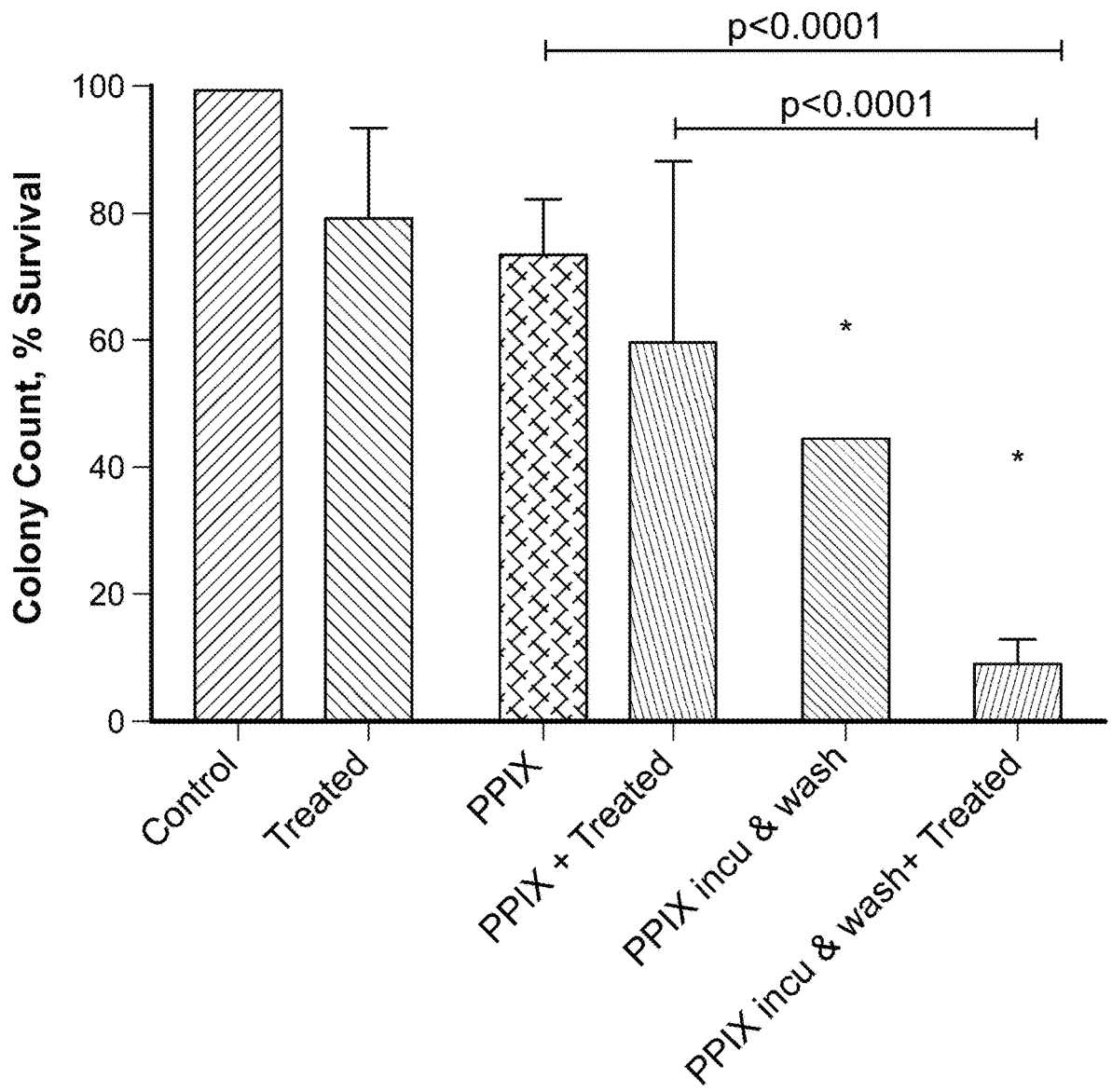
FIGS. 39, 40 and 41 are graphs depicting GBS survival for different combinations of 0.05 mg/mL PPIX supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 39, irradiation of GBS without the addition of any PPIX showed a minimal decrease in percent GBS survival when compared to the control, i.e., approximately 80%, which demonstrates that GBS does not synthesize a sufficient amount of porphyrin. Also, GBS supplemented with 0.05 mg/mL PPIX (incubated), but without any irradiation, did not show much decrease in percent GBS survival when compared to the control, i.e., approximately 72%. In addition, irradiation of GBS supplemented with 0.05 mg/mL PPIX (incubated) showed a small decrease in percent GBS survival when compared to the control, i.e., approximately 60%. As explained above, this result is different than those seen in FIGS. 33 and 34 because the bacteria was incubated at 37° C. for approximately thirty minutes before irradiation, which gives them more time to grow, hence starting with an overall increased CFU/mL compared to Examples 1 and 2 where irradiation was commenced immediately after dilutions were made. This is reflected in the higher percent of remnant colonies obtained in this experiment. GBS supplemented with 0.05 mg/mL PPIX (incubated and washed) showed some decrease in percent GBS survival when compared to the control, i.e., approximately 92%. Again, it is believed that there is a slight decrease in percent GBS survival because PPIX may have some minimal suppressive effects that may be concentration dependent. Further, irradiation of GBS supplemented with 0.05 mg/mL PPIX (incubated and washed) showed a significant decrease in percent GBS survival when compared to the control, i.e., approximately 18%.

Overall, the decrease in percent GBS survival was greatest for GBS supplemented with PPIX that was incubated and washed prior to irradiation, which suggests that the PPIX was internalized into the GBS during the incubation period.

It should be noted that the percent GBS survival for GBS supplemented with PPIX that was incubated prior to irradiation was greater than the percent GBS survival for GBS supplemented with PPIX that was incubated and washed prior to irradiation. This difference is believed to be caused by the fact that incubation with porphyrin has some minimal effect on bacterial survival and, thus, it is likely that more dead bacteria will be washed during the washing step of the incubated sample resulting in a reduced starting CFU/mL.

Example 8

Figure 40:
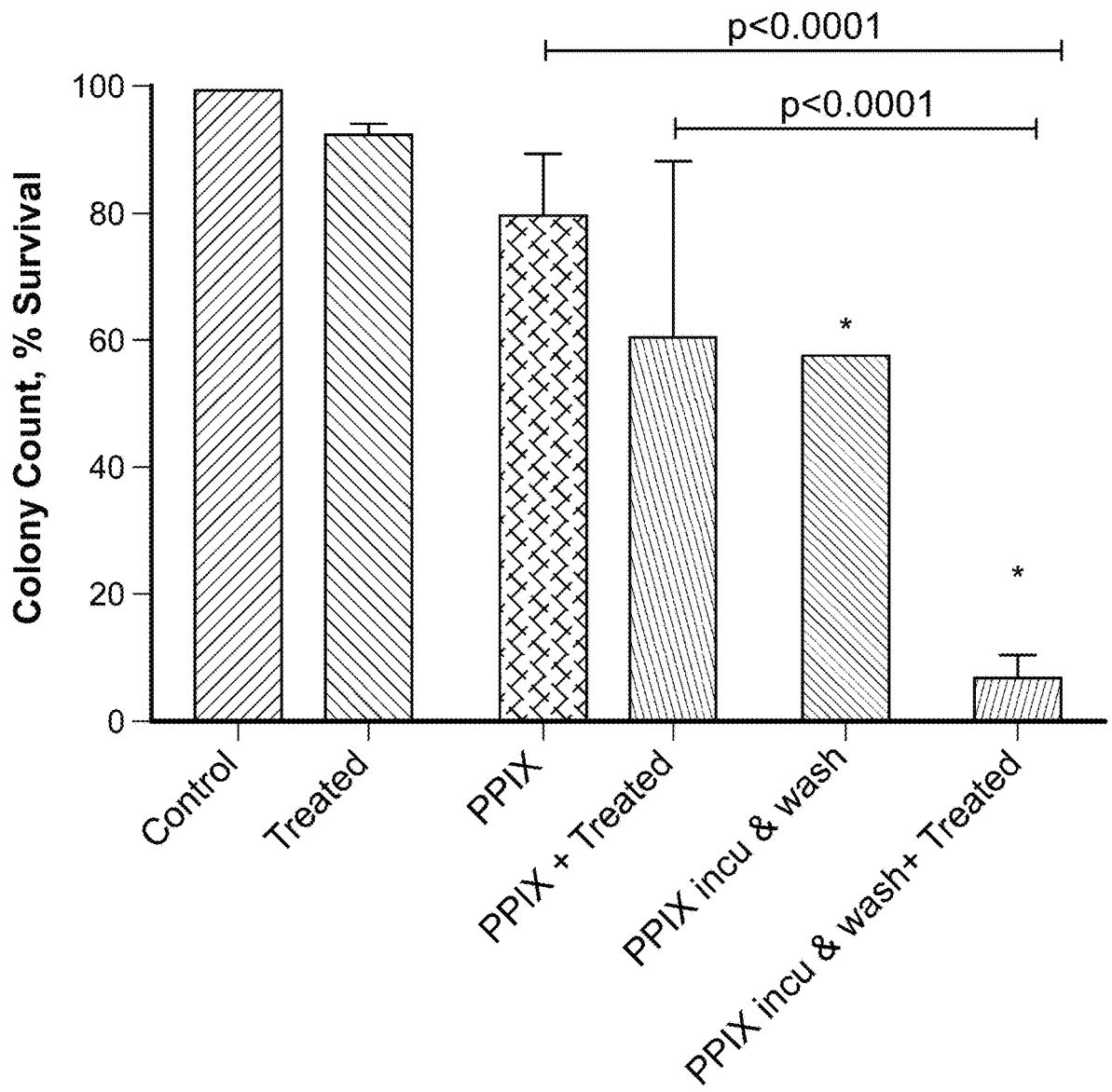

In an eighth experiment, the GBS were assigned to six experimental groups: (1) GBS only (control); (2) GBS and light; (3) GBS supplemented with 0.05 mg/mL PPIX (incubated); (4) GBS supplemented with 0.05 mg/mL PPIX (incubated) and light; (5) GBS supplemented with 0.05 mg/mL PPIX (incubated and washed); and (6) GBS supplemented with 0.05 mg/mL PPIX (incubated and washed) and light. The results are shown in FIG. 40. It should be noted that the results for Example 8 are similar to those of Example 7, which is indicative of the reproducibility of the data.

Example 9

In a ninth experiment, the GBS were assigned to six experimental groups: (1) GBS only (control); (2) GBS and light; (3) GBS supplemented with 0.05 mg/mL PPIX (incubated); (4) GBS supplemented with 0.05 mg/mL PPIX (incubated) and light; (5) GBS supplemented with 0.05 mg/mL PPIX (incubated and washed); and (6) GBS supplemented with 0.05 mg/mL PPIX (incubated and washed) and light. The results are shown in FIG. 41.

Figure 41:
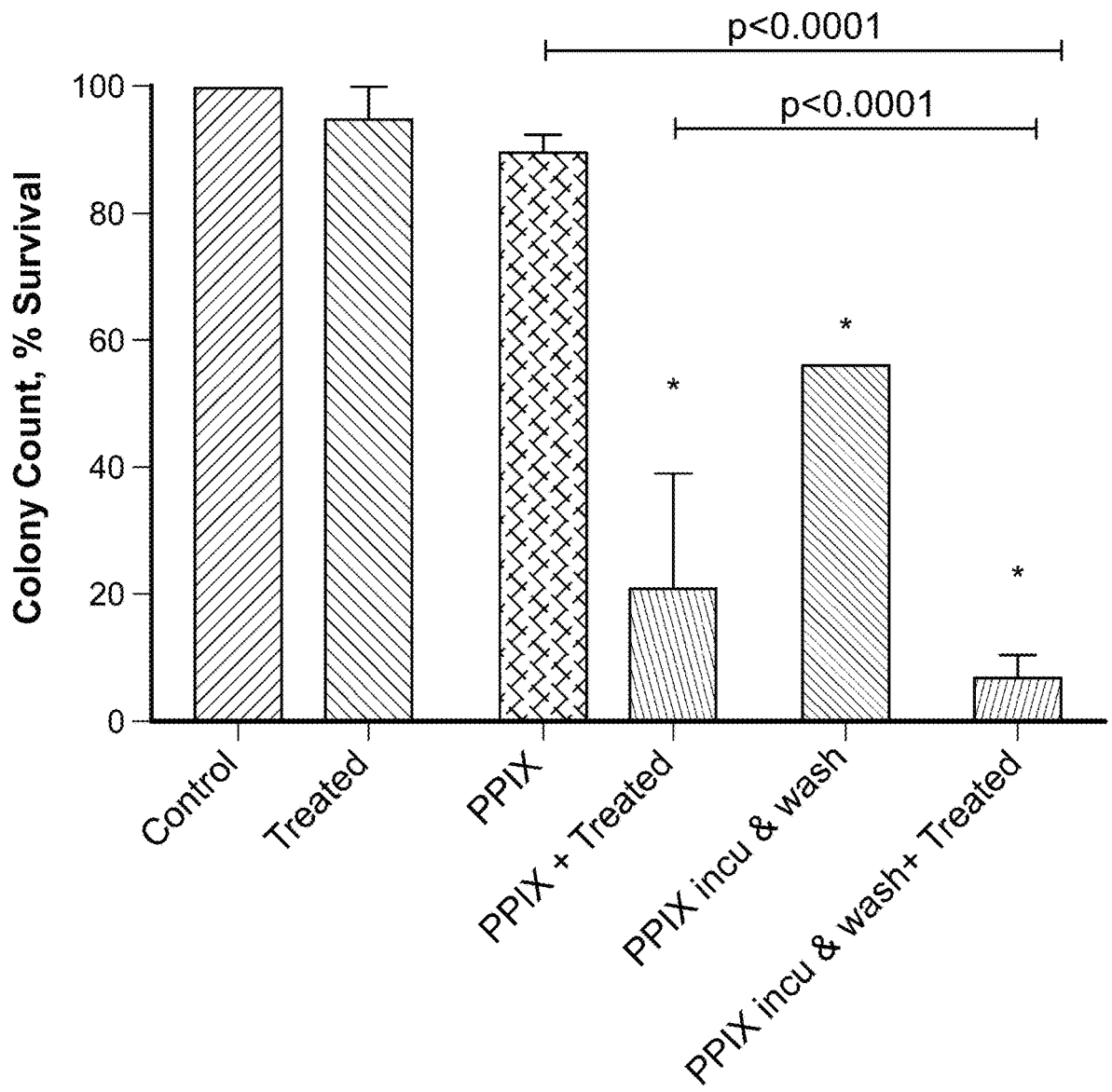

As can be seen in FIG. 41, irradiation of GBS without the addition of any PPIX showed a minimal decrease in percent GBS survival when compared to the control, i.e., approximately 94%, which demonstrates that GBS does not synthesize a sufficient amount of porphyrin. Also, GBS supplemented with 0.05 mg/mL PPIX (incubated), but without any irradiation, did not show much decrease in percent GBS survival when compared to the control, i.e., approximately 90%. In addition, irradiation of GBS supplemented with 0.05 mg/mL PPIX (incubated) showed a large decrease in percent GBS survival when compared to the control, i.e., approximately 20%. GBS supplemented with 0.05 mg/mL PPIX (incubated and washed) also showed some decrease in percent GBS survival when compared to the control, i.e., approximately 54%. Again, it is believed that there is a slight decrease in percent GBS survival because PPIX may have some minimal suppressive effects that may be concentration dependent. Further, irradiation of GBS supplemented with 0.05 mg/mL PPIX (incubated and washed) showed a significant decrease in percent GBS survival when compared to the control, i.e., approximately 6%, which suggests that the PPIX was internalized into the GBS during the incubation period.

Example 10

In a tenth experiment, the GBS were assigned to six experimental groups: (1) GBS only (control); (2) GBS and light; (3) GBS supplemented with 0.05 mg/mL CP III (incubated); (4) GBS supplemented with 0.05 mg/mL CP III (incubated) and light; (5) GBS supplemented with 0.05 mg/mL CP III (incubated and washed); and (6) GBS supplemented with 0.05 mg/mL CP III (incubated and washed) and light. Because the CP III was solubilized in ethanol, two additional experimental groups were included to test whether the quantity of ethanol used as a solvent had any significant effect on bacterial growth suppression: (7) ethanol only and (8) ethanol and light. The results are shown in FIG. 42.

Figure 42:
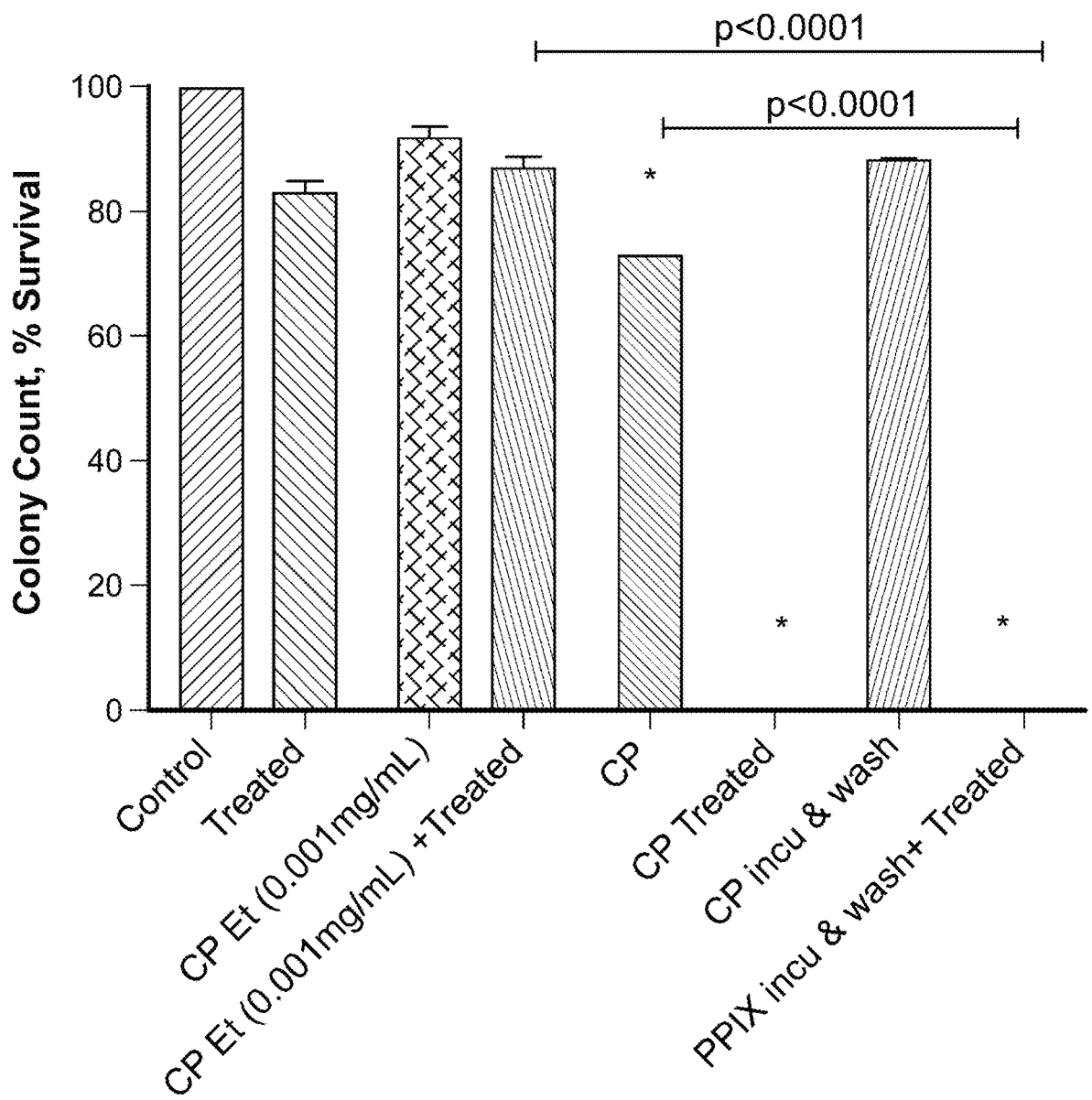
FIG. 42 is a graph depicting GBS survival for different combinations of 0.05 mg/mL CP III supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 42, irradiation of GBS without the addition of any CP III showed a small decrease in percent GBS survival when compared to the control, i.e., approximately 82%, which again demonstrates that GBS does not synthesize a sufficient amount of porphyrin. Also, GBS supplemented with 0.05 mg/mL CP III (incubated), but without any irradiation, showed a small decrease in percent GBS survival when compared to the control, i.e., approximately 90%. In addition, irradiation of GBS supplemented with 0.05 mg/mL CP III (incubated) showed complete bacterial kill, i.e., 0% GBS survival. GBS supplemented with 0.05 mg/mL CP III (incubated and washed) showed minimal decrease in percent GBS survival when compared to the control, i.e., approximately 72%. Further, irradiation of GBS supplemented with 0.05 mg/mL CP III (incubated and washed) showed complete bacterial kill, i.e., 0% GBS survival, which suggests that the CP III was internalized into the GBS during the incubation period. It should also be noted that ethanol did not have any significant contribution to the observed suppressive effect.

Example 11

In an eleventh experiment, the GBS were assigned to six experimental groups: (1) GBS only (control); (2) GBS and light; (3) GBS supplemented with 0.08 mg/mL PPIX (incubated); (4) GBS supplemented with 0.08 mg/mL PPIX (incubated) and light; (5) GBS supplemented with 0.08 mg/mL PPIX (incubated and washed); and (6) GBS supplemented with 0.08 mg/mL PPIX (incubated and washed) and light. The results are shown in FIG. 43.

Figure 43:
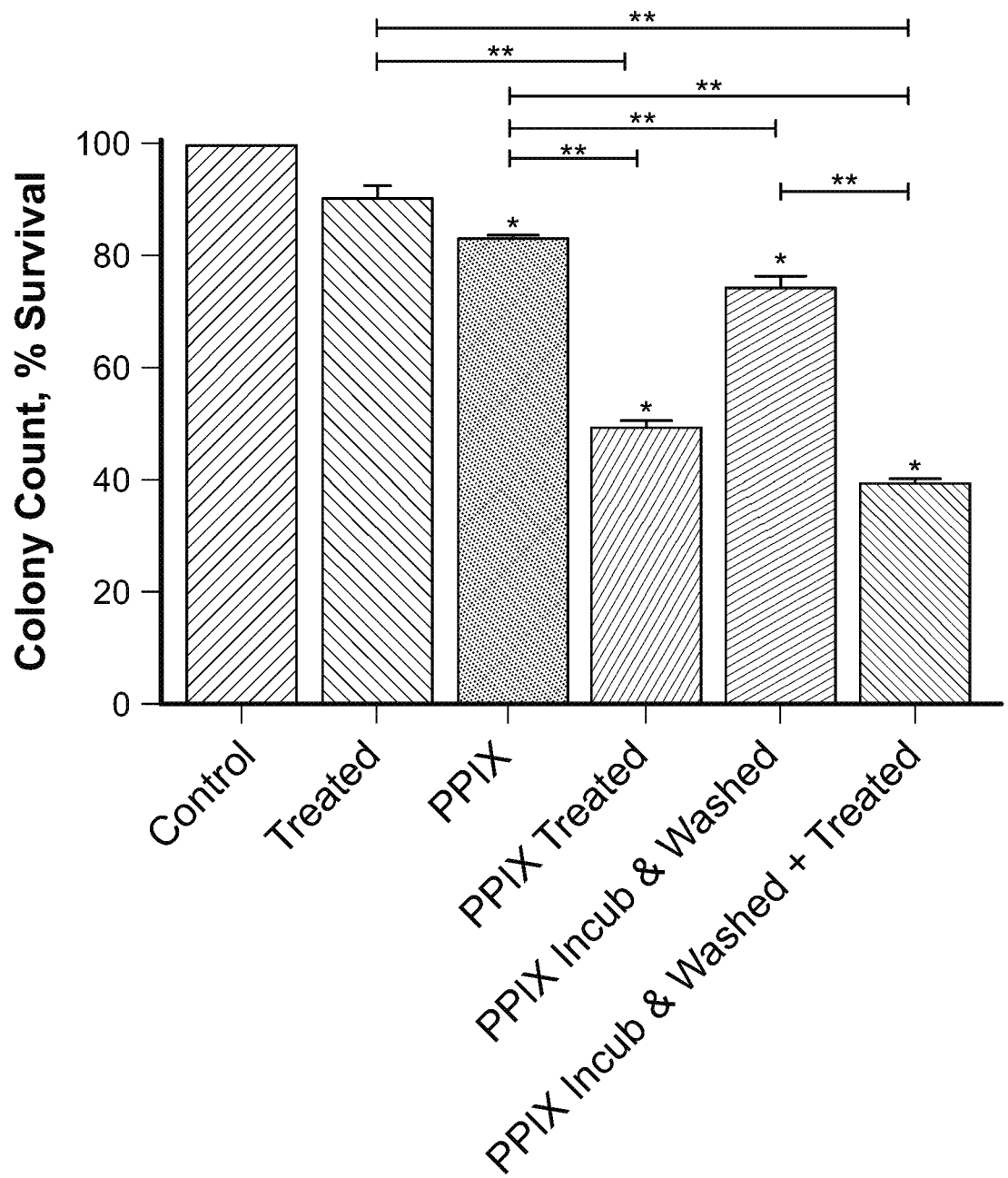
FIGS. 43 and 44 are graphs depicting GBS survival for different combinations of 0.08 mg/mL PPIX supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 43, irradiation of GBS without the addition of any PPIX showed a minimal decrease in percent GBS survival when compared to the control, i.e., approximately 98%, which demonstrates that GBS does not synthesize a sufficient amount of porphyrin. Also, GBS supplemented with 0.08 mg/mL PPIX (incubated), but without any irradiation, did not show much decrease in percent GBS survival when compared to the control, i.e., approximately 84%. In addition, irradiation of GBS supplemented with 0.08 mg/mL PPIX (incubated) showed some decrease in percent GBS survival when compared to the control, i.e., approximately 52%. GBS supplemented with 0.08 mg/mL PPIX (incubated and washed) showed a small decrease in percent GBS survival when compared to the control, i.e., approximately 76%. Again, it is believed that there is a slight decrease in percent GBS survival because PPIX may have some minimal suppressive effects that may be concentration dependent. Further, irradiation of GBS supplemented with 0.08 mg/mL PPIX (incubated and washed) showed some decrease in percent GBS survival when compared to the control, i.e., approximately 40%, which suggests that at least some of the PPIX was internalized into the GBS during the incubation period.

Example 12

Figure 44:
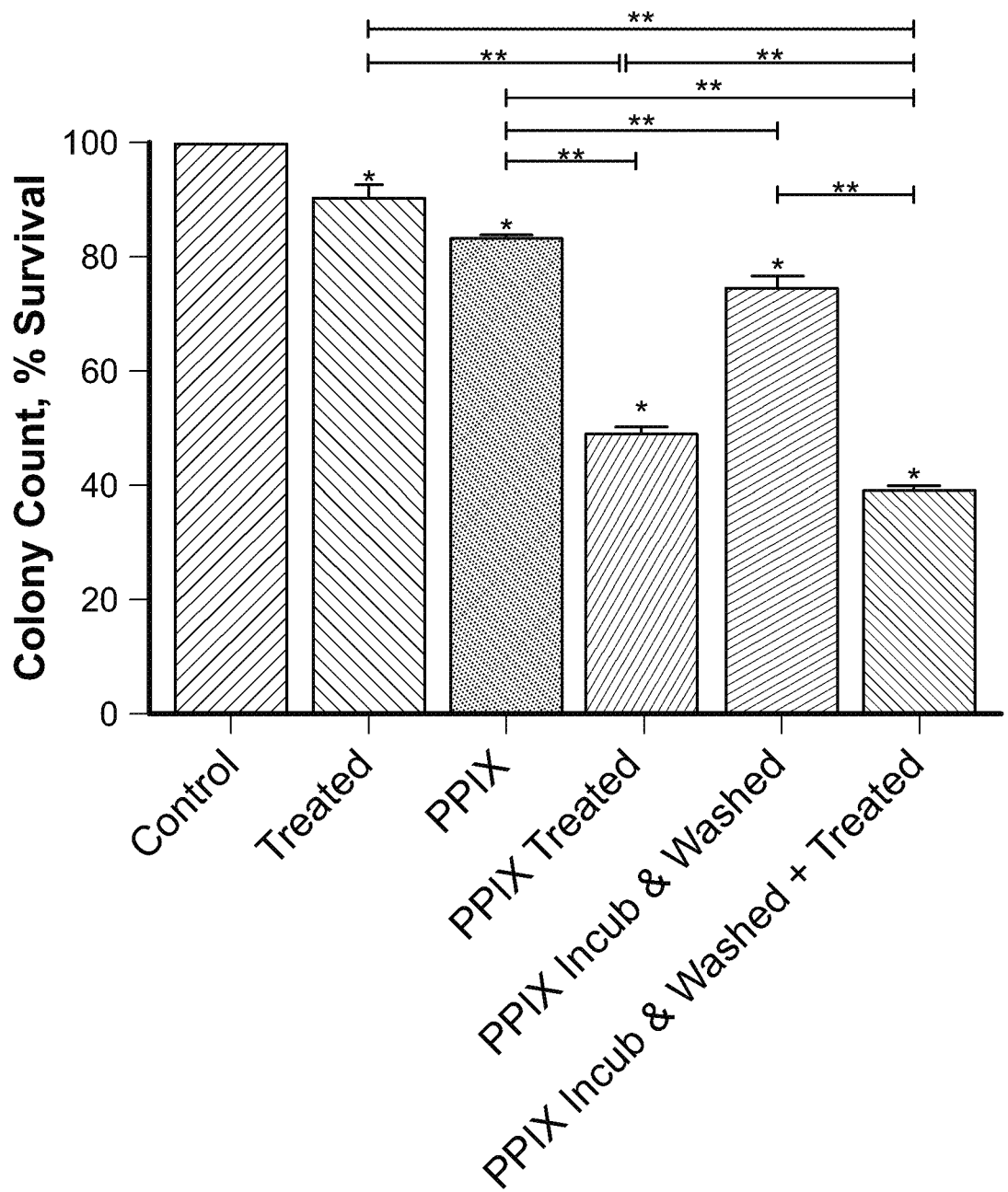

In a twelfth experiment, the GBS were assigned to six experimental groups: (1) GBS only (control); (2) GBS and light; (3) GBS supplemented with 0.08 mg/mL PPIX (incubated); (4) GBS supplemented with 0.08 mg/mL PPIX (incubated) and light; (5) GBS supplemented with 0.08 mg/mL PPIX (incubated and washed); and (6) GBS supplemented with 0.08 mg/mL PPIX (incubated and washed) and light. The results are shown in FIG. 44. It should be noted that the results for Example 12 are similar to those of Example 11, which is indicative of the reproducibility of the data.

Example 13

In a thirteenth experiment, the GBS were assigned to six experimental groups: (1) GBS only (control); (2) GBS and light; (3) GBS supplemented with 0.2 mg/mL PPIX (incubated); (4) GBS supplemented with 0.2 mg/mL PPIX (incubated) and light; (5) GBS supplemented with 0.2 mg/mL PPIX (incubated and washed); and (6) GBS supplemented with 0.2 mg/mL PPIX (incubated and washed) and light. The results are shown in FIG. 45.

Figure 45:
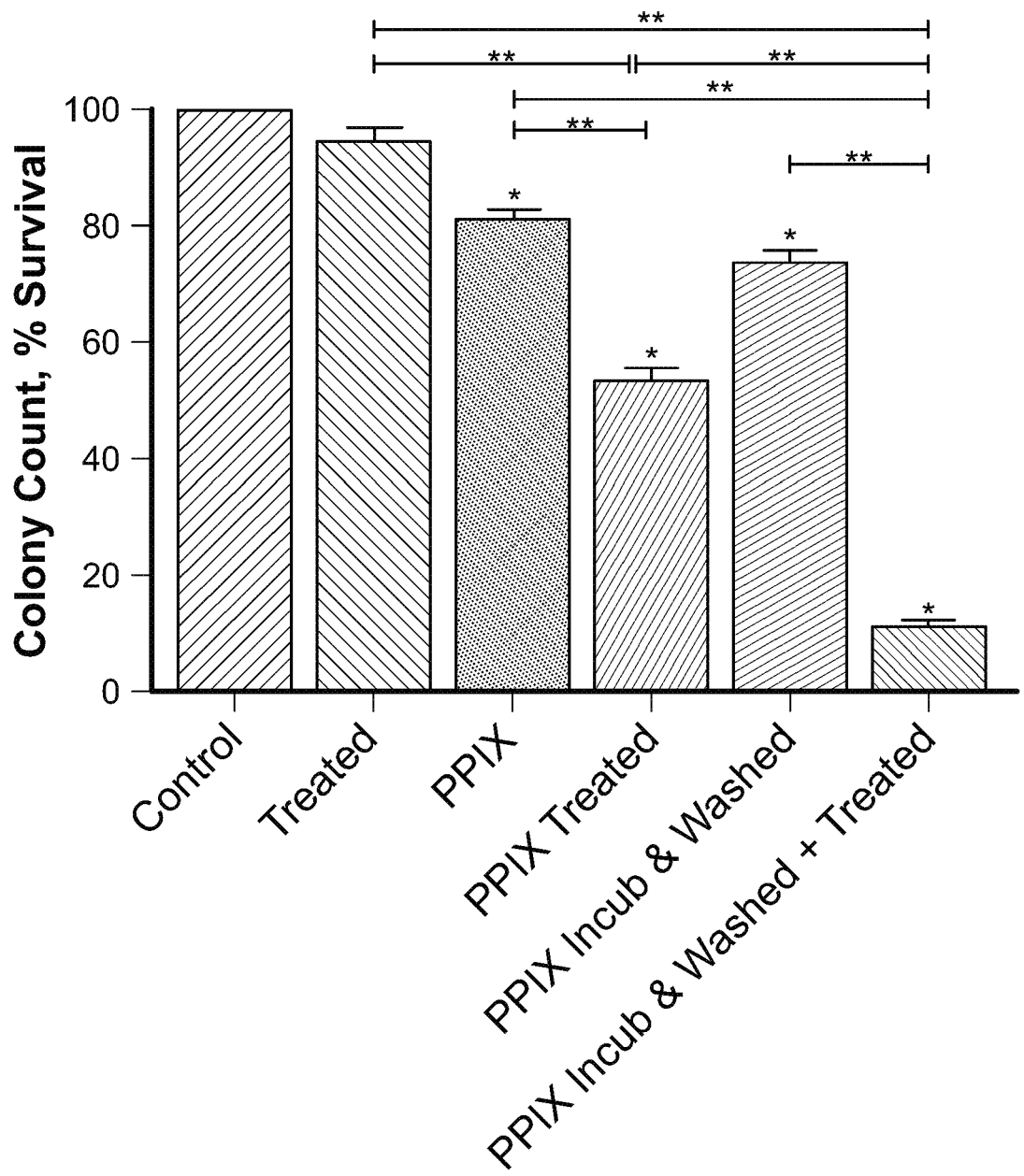
FIGS. 45, 46 and 47 are graphs depicting GBS survival for different combinations of 0.2 mg/mL PPIX supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 45, irradiation of GBS without the addition of any PPIX showed a minimal decrease in percent GBS survival when compared to the control, i.e., approximately 95%, which demonstrates that GBS does not synthesize a sufficient amount of porphyrin. Also, GBS supplemented with 0.2 mg/mL PPIX (incubated), but without any irradiation, did not show much decrease in percent GBS survival when compared to the control, i.e., approximately 80%. In addition, irradiation of GBS supplemented with 0.2 mg/mL PPIX (incubated) showed some decrease in percent GBS survival when compared to the control, i.e., approximately 50%. GBS supplemented with 0.2 mg/mL PPIX (incubated and washed) showed a small decrease in percent GBS survival when compared to the control, i.e., approximately 78%. Again, it is believed that there is a slight decrease in percent GBS survival because PPIX may have some minimal suppressive effects that may be concentration dependent. Further, irradiation of GBS supplemented with 0.2 mg/mL PPIX (incubated and washed) showed a significant decrease in percent GBS survival when compared to the control, i.e., approximately 10%, which suggests that the PPIX was internalized into the GBS during the incubation period.

Example 14

Figure 46:
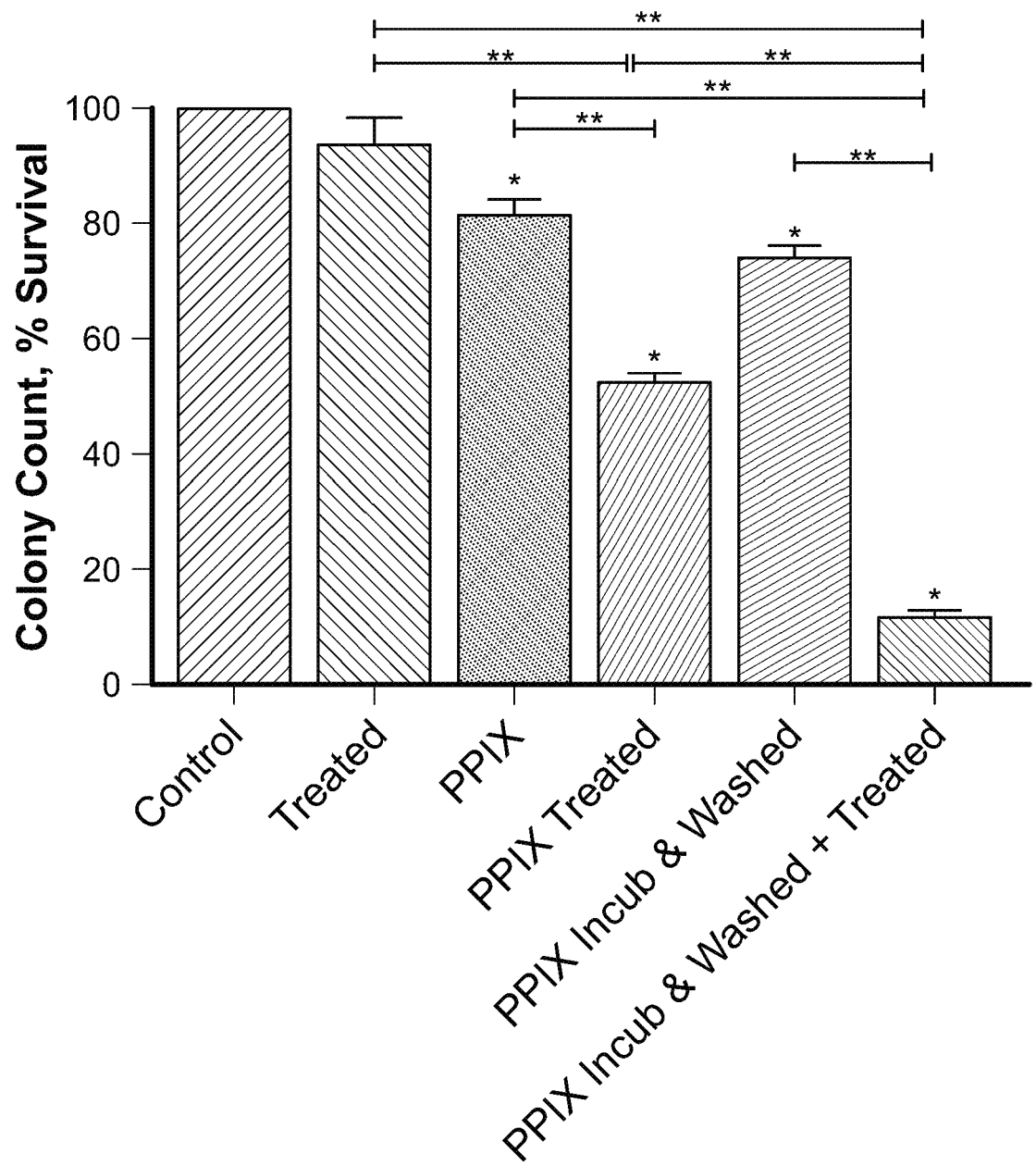

In a fourteenth experiment, the GBS were assigned to six experimental groups: (1) GBS only (control); (2) GBS and light; (3) GBS supplemented with 0.2 mg/mL PPIX (incubated), (4) GBS supplemented with 0.2 mg/mL PPIX (incubated) and light; (5) GBS supplemented with 0.2 mg/mL PPIX (incubated and washed); and (6) GBS supplemented with 0.2 mg/mL PPIX (incubated and washed) and light. The results are shown in FIG. 46. It should be noted that the results for Example 14 are similar to those of Example 13, which is indicative of the reproducibility of the data.

Example 15

Figure 47:
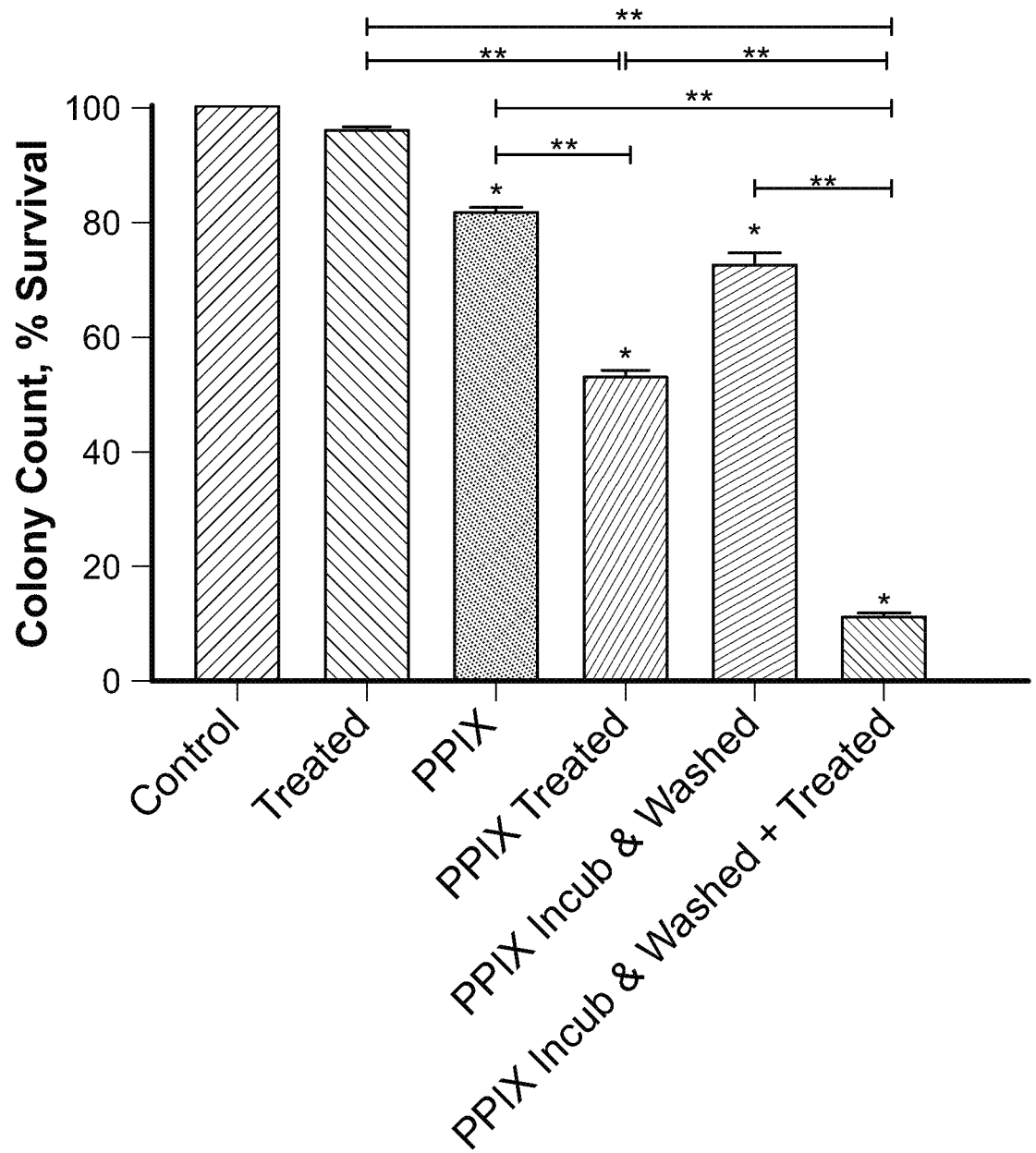

In a fifteenth experiment, the GBS were assigned to six experimental groups: (1) GBS only (control); (2) GBS and light; (3) GBS supplemented with 0.2 mg/mL PPIX (incubated); (4) GBS supplemented with 0.2 mg/mL PPIX (incubated) and light; (5) GBS supplemented with 0.2 mg/mL PPIX (incubated and washed); and (6) GBS supplemented with 0.2 mg/mL PPIX (incubated and washed) and light. The results are shown in FIG. 47. It should be noted that the results for Example 15 are similar to those of Examples 13 and 14, which is again indicative of the reproducibility of the data.

Example 16

In a sixteenth experiment, the GBS were assigned to six experimental groups: (1) GBS only (control); (2) GBS and light; (3) GBS supplemented with 0.2 mg/mL CP III (incubated); (4) GBS supplemented with 0.2 mg/mL CP III (incubated) and light; (5) GBS supplemented with 0.2 mg/mL CP III (incubated and washed); and (6) GBS supplemented with 0.2 mg/mL CP III (incubated and washed) and light. Because the CP III was solubilized in ethanol, two additional experimental groups were included to test whether the quantity of ethanol used as a solvent had any significant effect on bacterial growth suppression: (7) ethanol only and (8) ethanol and light. The results are shown in FIG. 48.

Figure 48:
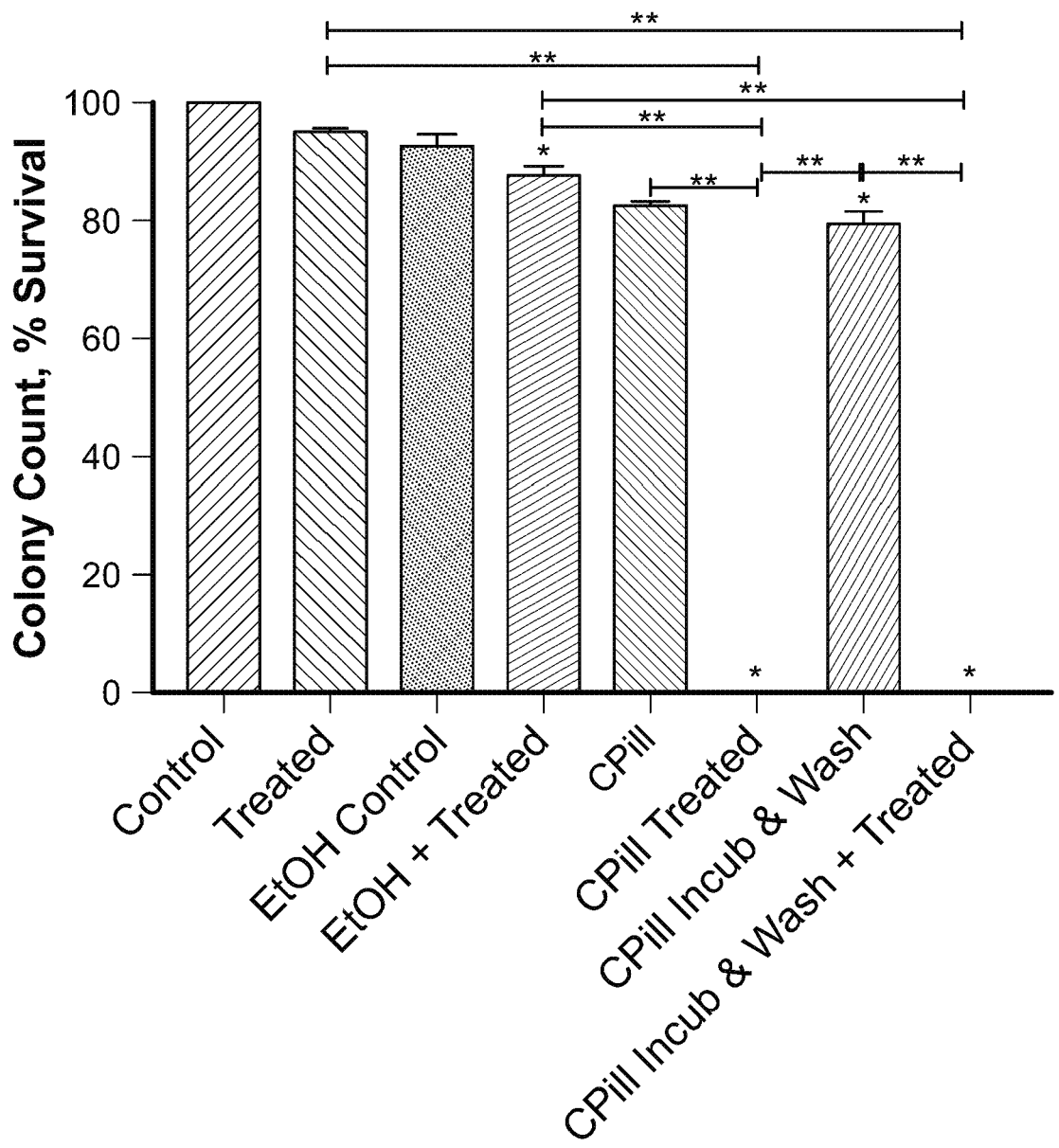
FIGS. 48 and 49 are graphs depicting GBS survival for different combinations of 0.2 mg/mL CP III supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

As can be seen in FIG. 48, irradiation of GBS without the addition of any CP III showed a small decrease in percent GBS survival when compared to the control, i.e., approximately 96%, which again demonstrates that GBS does not synthesize a sufficient amount of porphyrin. Also, GBS supplemented with 0.2 mg/mL CP III (incubated), but without any irradiation, showed a small decrease in percent GBS survival when compared to the control, i.e., approximately 82%. In addition, irradiation of GBS supplemented with 0.2 mg/mL CP III (incubated) showed complete bacterial kill, i.e., 0% GBS survival. GBS supplemented with 0.2 mg/mL CP III (incubated and washed) showed minimal decrease in percent GBS survival when compared to the control, i.e., approximately 80%. Further, irradiation of GBS supplemented with 0.2 mg/mL CP III (incubated washed) showed complete bacterial kill, i.e., 0% GBS survival, which suggests that the CP III was internalized into the GBS during the incubation period. It should also be noted that ethanol did not have any significant contribution to the observed suppressive effect.

Example 17

In a seventeenth experiment, the GBS were assigned to six experimental groups: (1) GBS only (control); (2) GBS and light; (3) GBS supplemented with 0.2 mg/mL CP III (incubated): (4) GBS supplemented with 0.2 mg/mL CP III (incubated) and light; (5) GBS supplemented with 0.2 mg/mL CP III (incubated and washed); and (6) GBS supplemented with 0.2 mg/mL CP III (incubated and washed) and light. Because the CP III was solubilized in ethanol, two additional experimental groups were included to test whether the quantity of ethanol used as a solvent had any significant effect on bacterial growth suppression: (7) ethanol only and (8) ethanol and light. The results are shown in FIG. 49.

Figure 49:
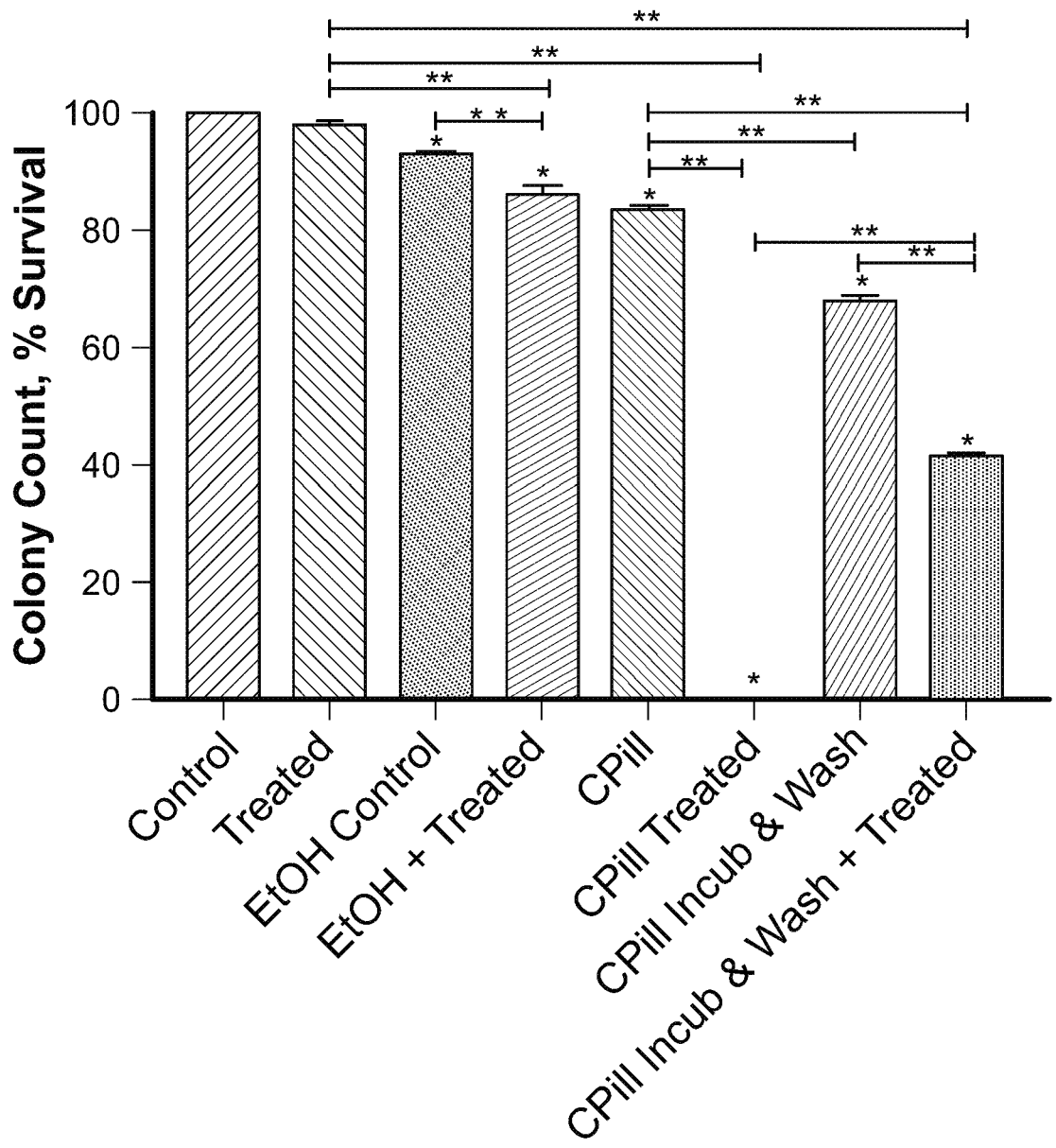

As can be seen in FIG. 49, irradiation of GBS without the addition of any CP III showed a small decrease in percent GBS survival when compared to the control, i.e., approximately 98%, which again demonstrates that GBS does not synthesize a sufficient amount of porphyrin. Also, GBS supplemented with 0.2 mg/mL CP III (incubated), but without any irradiation, showed a small decrease in percent GBS survival when compared to the control, i.e., approximately 82%. In addition, irradiation of GBS supplemented with 0.2 mg/mL CP III (incubated) showed complete bacterial kill, i.e., 0% GBS survival. GBS supplemented with 0.2 mg/mL CP III (incubated and washed) showed a small decrease in percent GBS survival when compared to the control, i.e., approximately 72%. Further, irradiation of GBS supplemented with 0.2 mg/mL CP III (incubated and washed) showed some decrease in percent GBS survival when compared to the control, i.e., approximately 42%. It should also be noted that ethanol did not have any significant contribution to the observed suppressive effect.

Example 18

Figure 50:
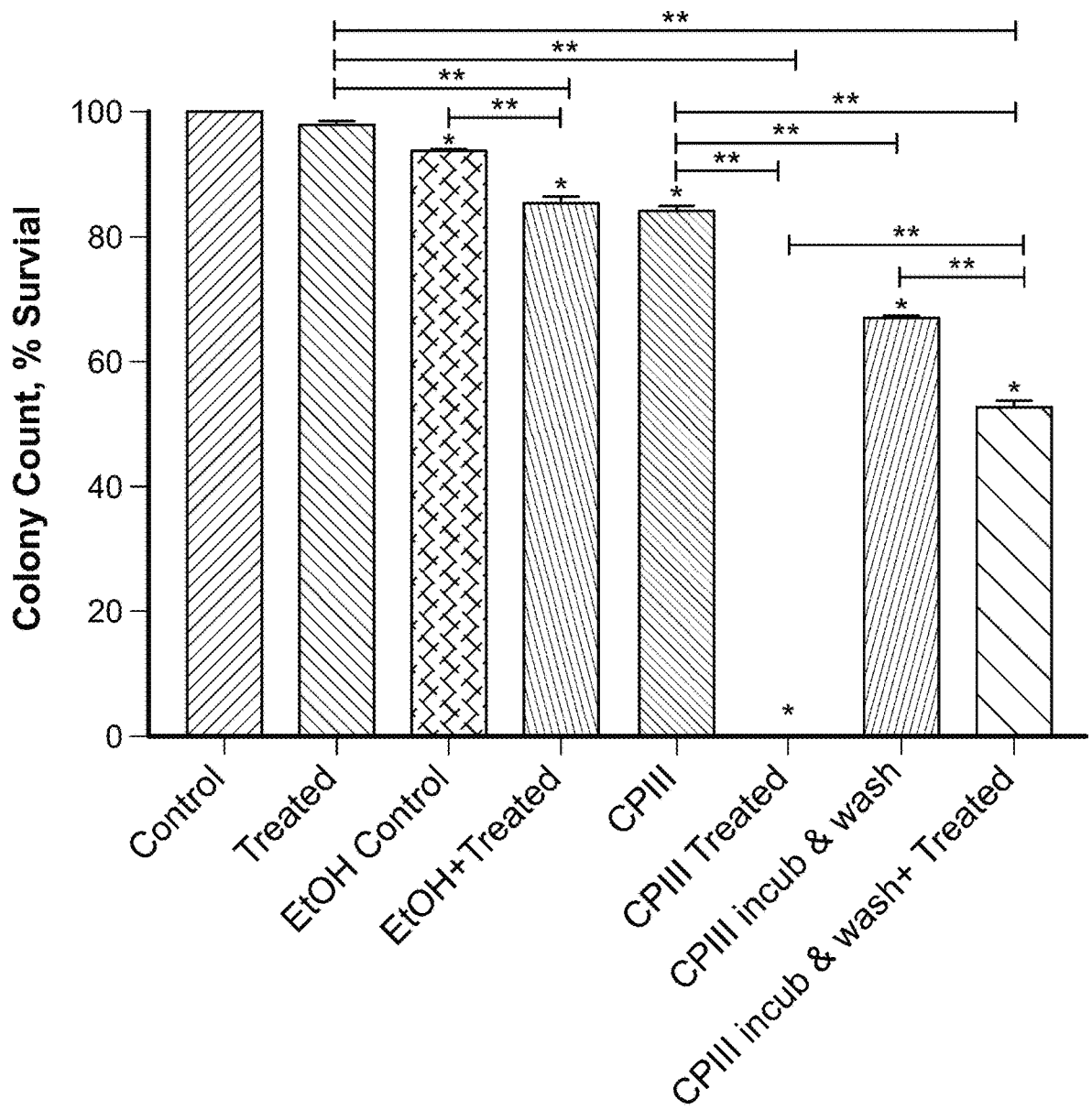
FIG. 50 is a graph depicting GBS survival for different combinations of 0.08 mg/mL CP III supplementation (with optional incubation and wash after supplementation) and/or irradiation with 450 nm light at a radiant exposure of 7.56 J/cm$^2$; average irradiance of 3 mW/cm$^2$; pulsed mode of irradiation (33% duty factor); and multiple irradiation at 0, 72 and 144 hours.

In an eighteenth experiment, the GBS were assigned to six experimental groups: (1) GBS only (control); (2) GBS and light; (3) GBS supplemented with 0.2 mg/mL CP III (incubated); (4) GBS supplemented with 0.2 mg/mL CP III (incubated) and light; (5) GBS supplemented with 0.2 mg/mL CP III (incubated and washed); and (6) GBS supplemented with 0.2 mg/mL CP III (incubated and washed) and light. Because the CP III was solubilized in ethanol, two additional experimental groups were included to test whether the quantity of ethanol used as a solvent had any significant effect on bacterial growth suppression: (7) ethanol only and (8) ethanol and light. The results are shown in FIG. 50. It should be noted that the results for Example 18 are similar to those of Example 17, which is indicative of the reproducibility of the data.

V. Detection of Emission Spectra of Light Absorbing Pigment "Porphyrins" in *P. acnes*

*P. acnes* gives off a florescence in the red spectrum of 600-700 nm (typically 620 nm to 640 nm) when illuminated with pulsed purple or blue light. Without being bound by any one theory, it is believed that porphyrins are excited (i.e., optically pumped) with each light pulse and, upon return to their ground state, create an oxidation reaction that produces free radicals which subsequently destroy mitochondrial membranes, DNA or other cellular structures, as described above. Thus, if a photo sensor is used to detect red or other wavelengths given off by the cells undergoing irradiation, then the feedback can be used to control the dose of light, e.g., irradiation would take place until the porphyrin level had reached a minimum point and would not begin until porphyrin recovery took place. This may take place as part of the replication cycle of the microorganism.

Testing was performed to detect the emission spectra of light absorbing pigment porphyrins in *P. acnes*.

A 72 hour culture of *P. acnes* was centrifuged at 13,300 rpm for five minutes, supernatant discarded and re-suspended in 1 mL saline. It was then washed again by centrifuging at 13,300 rpm for 5 minutes with 1 mL saline (washing ensures that no other factors—aside from the innate porphyrins found in the *P. acnes* cells—would contribute to the detection). The optical density was adjusted using McFarland standard to 0.8 to 1.0 at 625 nm for a concentration of 108 CFU/mL. A volume of 10 µl of this solution was placed on concanavalin A coated dishes and excited as described below.

Figure 23:
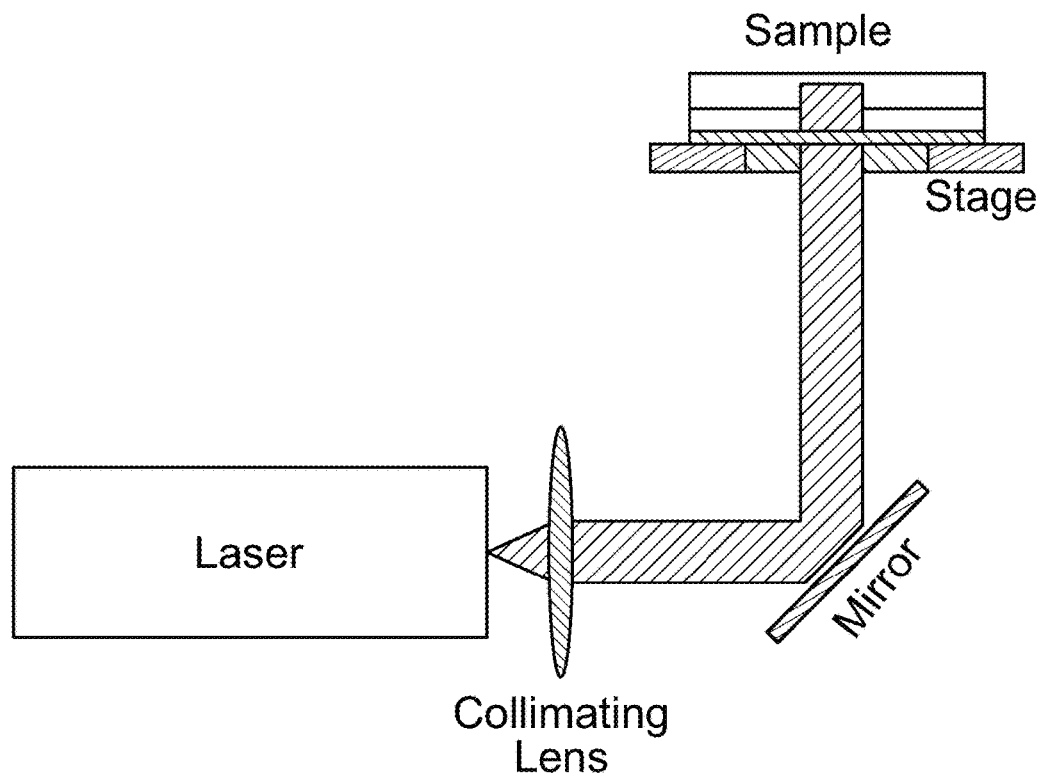
FIG. 23 is a schematic illustration depicting an experimental set-up used in bacteria irradiation with a 458 nm laser light.

As illustrated in FIG. 23, the set-up used for irradiating the bacteria employed a 458 nm Ar-Ion laser assembly (Edmund optics, USA) delivering continuous wave (CW) light with spectral bandwidth of less than 1 nm and a total power of 150 mW. The original, divergent laser beam was collimated using a lens (focal length 35 mm) placed about 22 mm from the laser aperture. The final beam diameter was 15 mm with a cross-sectional area of 3 $cm^2$, which approximately matched the area of the dish coated with concanavalin A. The sample was placed on a translation stage positioned about 25 cm from the collimating lens.

The sample was placed onto an inverted microscope (Axio Observer—Z1, Carl Zeiss, Oberkochen, Germany) and illuminated through the back port of the microscope using a continuous wave Ar-Ion laser (Edmund Optics) with a 458 nm wavelength. The excitation light (0.5 mW) was focused by a 63× water immersion objective with numerical aperture (NA) of 1.2. The microscope scanning head consisted of a computer-controlled OptiMiS TruLine (Aurora Spectral Technologies, Milwaukee, Wis., USA). The detection was done using a modified OptiMiS detection module (a commercial prototype of OptiMiS d-Lux), which included a galvanometric scanner used to descan the fluorescence beam which then falls on an electron multiplying charged coupled device (iXon3, Andor, Belfast, UK). This descanning concept allowed the use of OptiMiS as a confocal (rather than a two-photon) microscope. This in turn reduced the laser-induced photo-bleaching of the cellular fluorescence, which was critical in these experiments given the low intensity of the signal detected. In order to capture full spectrum images, the sample was scanned line by line. The line images were further reconstructed resulting in an image for each wavelength channel (total of 300 channels).

The extraction of the porphyrin spectrum was performed by first measuring the spectrum of the emission from the bacteria and the spectrum of the media outside of the bacteria. Next, the spectrum of the media was subtracted from the bacterial emission spectrum while considering the emission ratios between the bacteria and the outside media. Finally, the resulting spectrum was fitted with two Gaussians as the emission has two humps.

Figure 24A:
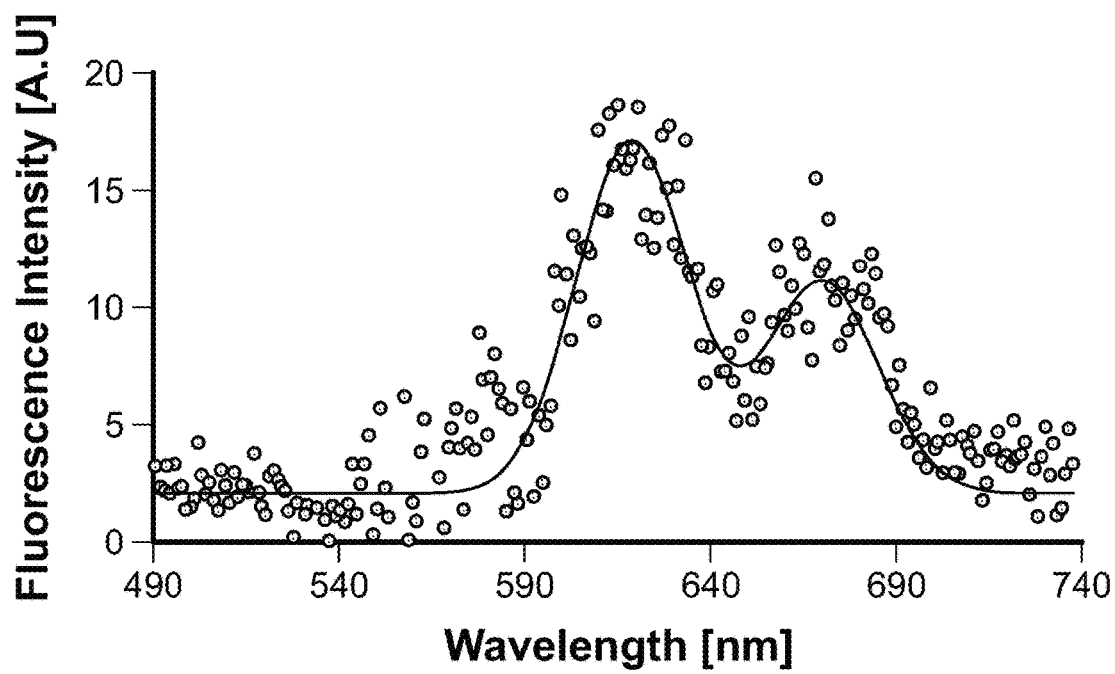
FIG. 24A is a graph depicting porphyrin emission extracted from *P. acnes* excited with 458 nm light.

FIG. 24A depicts the porphyrin emission spectrum extracted from *P. acnes* excited with 458 nm light and detected using OptiMiS TruLine (Aurora Spectral Technologies, Milwaukee, Wis.). The peak wavelengths of the resulting emission were 619 nm and 670 nm for the two apparent humps. This emission is characteristic of cytochrome C which most likely is present in the acne bacteria. However, it may still contain some emission from different porphyrins such as coproporphyrins which may participate in the bacterial eradication mechanism. It is proposed that the free radical production by peroxides generated from porphyrins exposed to purple or blue light may alter DNA structure and lead to destruction of the bacteria during its replicative phase. Thus, the timing of light exposures during the replicative phase may have significant impact on the kill rates.

Figure 24B:
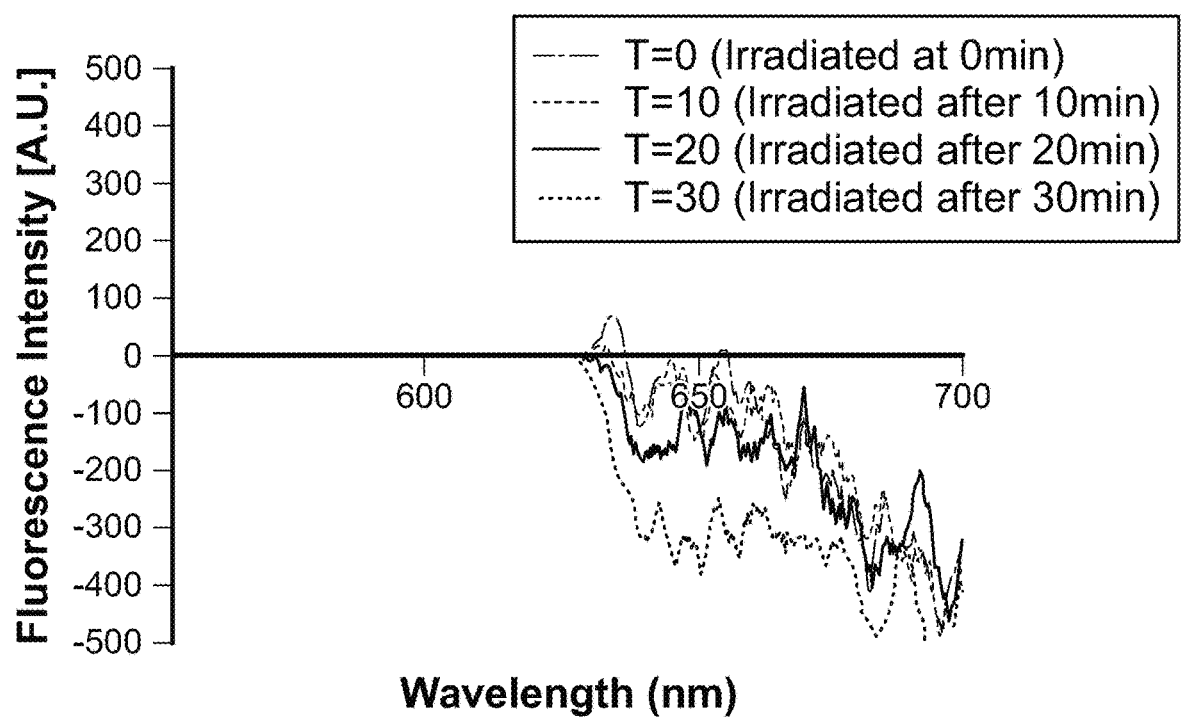
FIG. 24B is a graph depicting porphyrin fluorescence emission extracted from *P. acnes* excited with 450 nm light from the printed LED flexible lamp shown in FIG. 22 at an average irradiance of 3 mW/cm$^2$; pulsed mode of irradiation (33% duty factor); and multiple irradiation at 0, 10, 20 and 30 minutes.

FIG. 24B demonstrates the fluorescence spectra of *P. acnes* at various times during irradiation from zero to 30 minutes (measured at T=1, 10, 20 and 30 minutes). It can be readily seen that the fluorescence gradually depletes over time and thus can act as an indicator of porphyrin depletion at the cellular level. The porphyrin depletion follows the dose parameters (approximately 30 minutes of irradiation at 3 $mW/cm^2$) which were found to be optimal for photoeradication of bacteria. These experiments were performed in vitro, in a petri dish in agar, illuminated with 450 nm printed LEDs on a flexible substrate. The output was pulsed at a duty factor of 33% (10 microseconds on and 20 microseconds off) at an irradiance of 3 $mW/cm^2$. A calibrated ocean optics OCEAN-FX-VIS-NIR-ES spectrometer was used to record the fluorescence. The dish was held in a light tight housing. The blue 450 nm excitation light was filtered to eliminate all wavelengths beyond 420 and 480 nm. A filter was used below the dish to eliminate any wavelengths below 510 nm. The extraction of the porphyrin spectrum was performed by first measuring the spectrum of the emission from the bacteria and the spectrum of the media outside of the bacteria. Next, the spectrum of the media was subtracted from the bacterial emission spectrum while considering the emission ratios between the bacteria and the outside media. The spectra were then plotted.

Figure 24C:
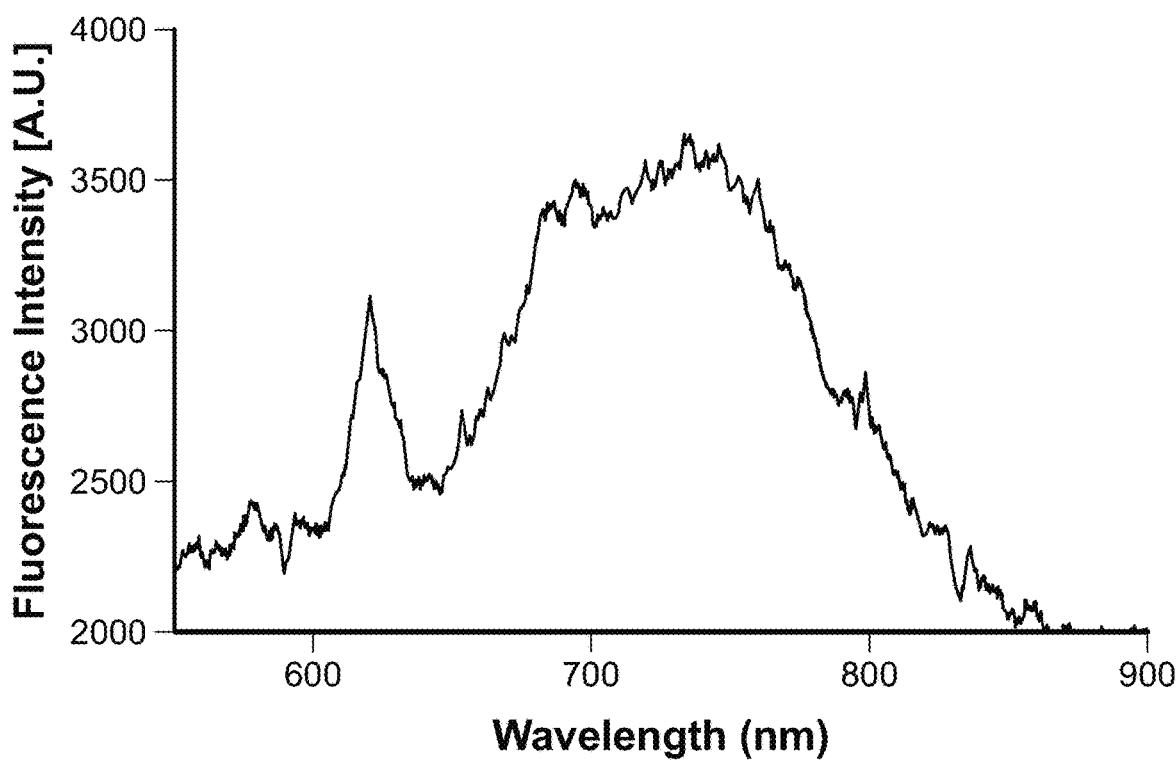
FIG. 24C is a graph depicting porphyrin emission extracted from a sample of Protoporphyrin IX excited with 450 nm light from the printed LED flexible lamp shown in FIG. 22.

FIG. 24C depicts the porphyrin emission spectrum extracted from a sample of Protoporphyrin IX excited with 450 nm printed LEDs on PET substrate and detected using an ocean optics OCEAN—FX-VIS-NIR-ES spectrometer in the same test set-up as FIG. 24B. The peak wavelengths of the resulting emission were 620 nm and 670 nm and 750 nm for the three apparent humps. This emission is similar to the initial porphyrin emission spectrum extracted from *P. acnes* excited with 458 nm light (FIG. 24A), however, it has a broader emission in the near infrared range.

Dosage can thus be optimized by detecting the emission spectrum of porphyrins or other emissions from the targeted bacteria, measuring fluorescence depletion or recovery, determining the optimal excitation periods and recovery between treatment sessions, and calculating ideal irradiation parameters, including dosage, irradiance, fluence and treatment schedule. It is also possible that killing of different strains of bacteria can be optimized using this method. Ideal wavelengths to measure porphyrin depletion are shown to be in the 620-640 nm range and the 670 nm range from the data presented, which correlates well with our data shown in FIGS. 24A, 24B and 24C. Ideal wavelengths to measure other types of emissions can be determined by one skilled in the art.

VI. Exemplary Light Sources

Various types of light sources may be used to provide light energy in accordance with the present invention. For example, the light source may comprise various types of lasers, LEDs, PLEDs/LEPs), QDLEDs, or fluorescent tubes emitting light in the purple or blue spectral region. The light source may directly illuminate the skin, tissue or other surface to be irradiated, such as a contaminated environment or food to be exposed to pulsed light. The light source may also be coupled by fiber optics or directly mounted to the edge of a lens-diffuser that redirects the light to the surface to be irradiated. These diffusers may contain numerous optical elements designed to diffuse and distribute the light evenly across the surface to be irradiated. These may include Fresnel lenses, various light pipes, irregularities and additional lens-like structures designed to pipe the light source and distribute it evenly over the surface of the lens-diffuser assembly. In order to improve the extraction or out-coupling of light, the device may include an internal scattering layer of high index particles such as TiOx in a transparent photoresist or a micro-lens array (MLA) layer. The light sources may also be placed directly behind the diffuser or Fresnel lens at a sufficient distance to allow the production of a substantially uniform beam to be applied to the surface to be irradiated. The light source may be a combination of white light and purple or blue light, whereupon the purple or blue light is pulsed and the white light is continuous wave (CW). These different wavelengths can be applied simultaneously or sequentially to irradiate an infected environment or food.

Figure 25:
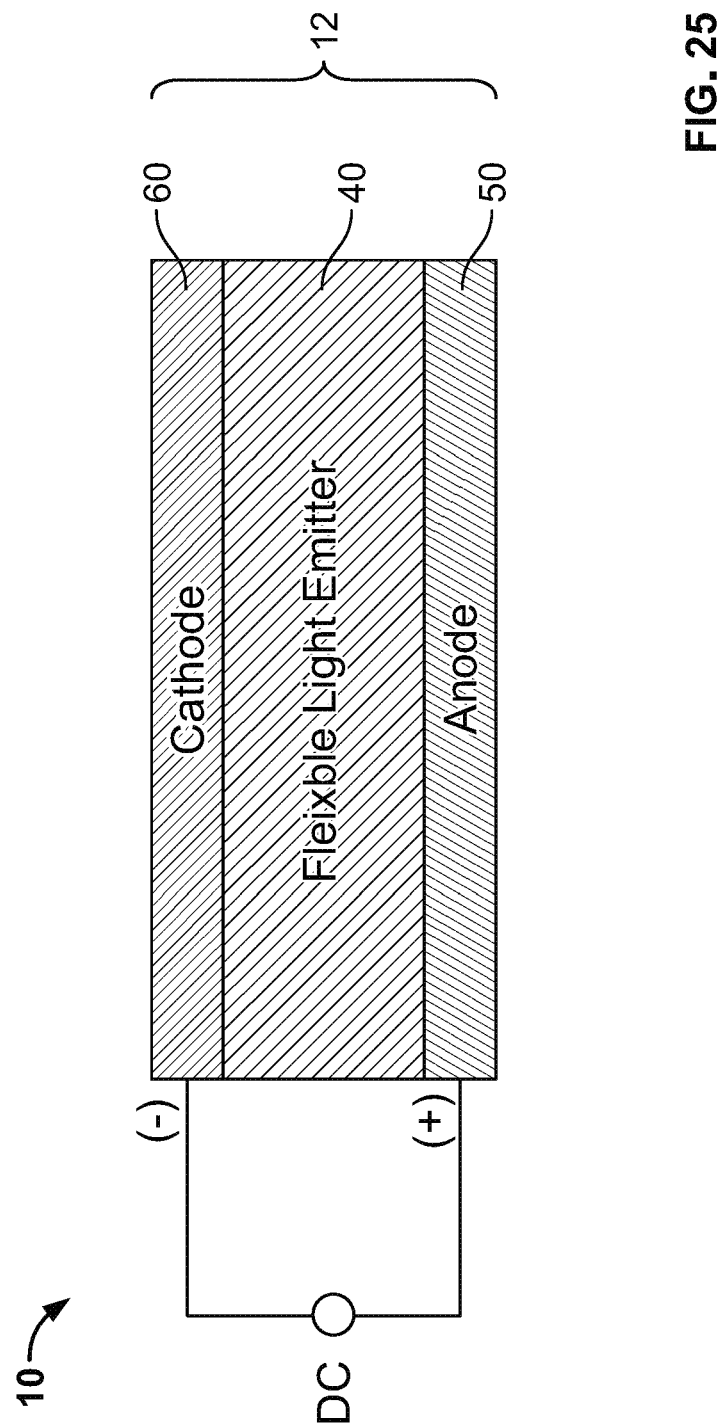
FIG. 25 illustrates the general structure of a light source in the form of a very thin layered structure that is suitable for delivering pulsed light in accordance with the present invention.

A preferred light source is provided in the form of a very thin layered structure. An example of this type of light source is shown generally as reference numeral 10 in FIG. 25. Light source 10 is comprised of a plurality of layers 12 including a flexible light emitter 40 located between an anode 50 and a cathode 60. A suitable power source is connected to light source 10. Preferably, direct current (DC) or pulsed DC is used to power light source 10. Light source 10 is substantially planar in its form, although it is preferably flexible and is more preferably conformable such that it may conform to the contours of the body, surfaces within a contaminated environment, or surfaces inside of a refrigeration or food display system. The overall thickness of light source 10 is typically about 10 mm or less (e.g., about 10, 9, 8, 7, 6, 5, 4, 3, 2, 1, 0.5, 0.4, 0.3, 0.2, 0.1, 0.05 mm or less).

Light source 10 produces light with an intensity that is substantially constant across the surface of the device so as to provide substantially uniform light emission. As described in more detail below, the light source may comprise, for example, organic light emitting diodes (OLEDs) or printed light emitting diodes (printed LEDs) (organic or inorganic) commonly referred to as LED ink. It can be appreciated that the light source is capable of decreasing hot spots on the surface of a subject's skin or tissue to provide a safer delivery of light to a subject. Also, a substantially uniform dose of light across the surface of the device ensures that all of the skin, tissue, surface or food is effectively treated with the same dose of light.

FIG. 22 shows an example of a light source that includes a plurality of light emitting diodes 42 printed on a flexible PET (polyethylene terephthalate)—ITO coated film 44 (referred to herein as a printed LED flexible lamp or a lighted substrate). In this example, the light emitting diodes 42 are printed in hexagon-shaped LED clusters at a density of 2.5 LEDS/mm$^2$. Of course, in other examples, the LED clusters could have other shapes, the LEDS could be printed across the entire surface of the film, and/or the LEDs could be printed in other densities in accordance with the present invention.

Figure 26A:
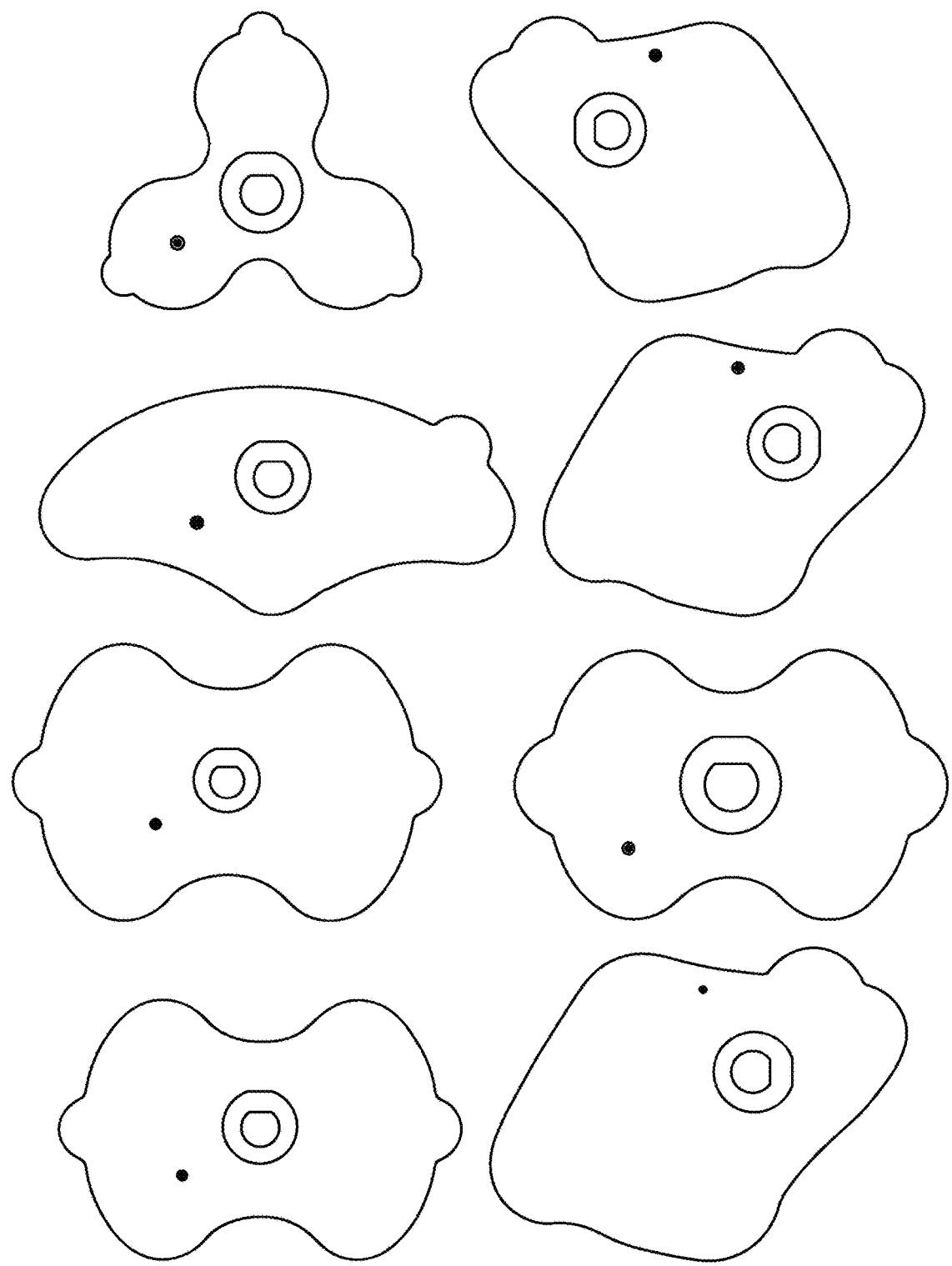
FIGS. 26A and 26B illustrate various exemplary shapes of light sources that are suitable for use in the light source of FIG. 25.
Figure 26B:
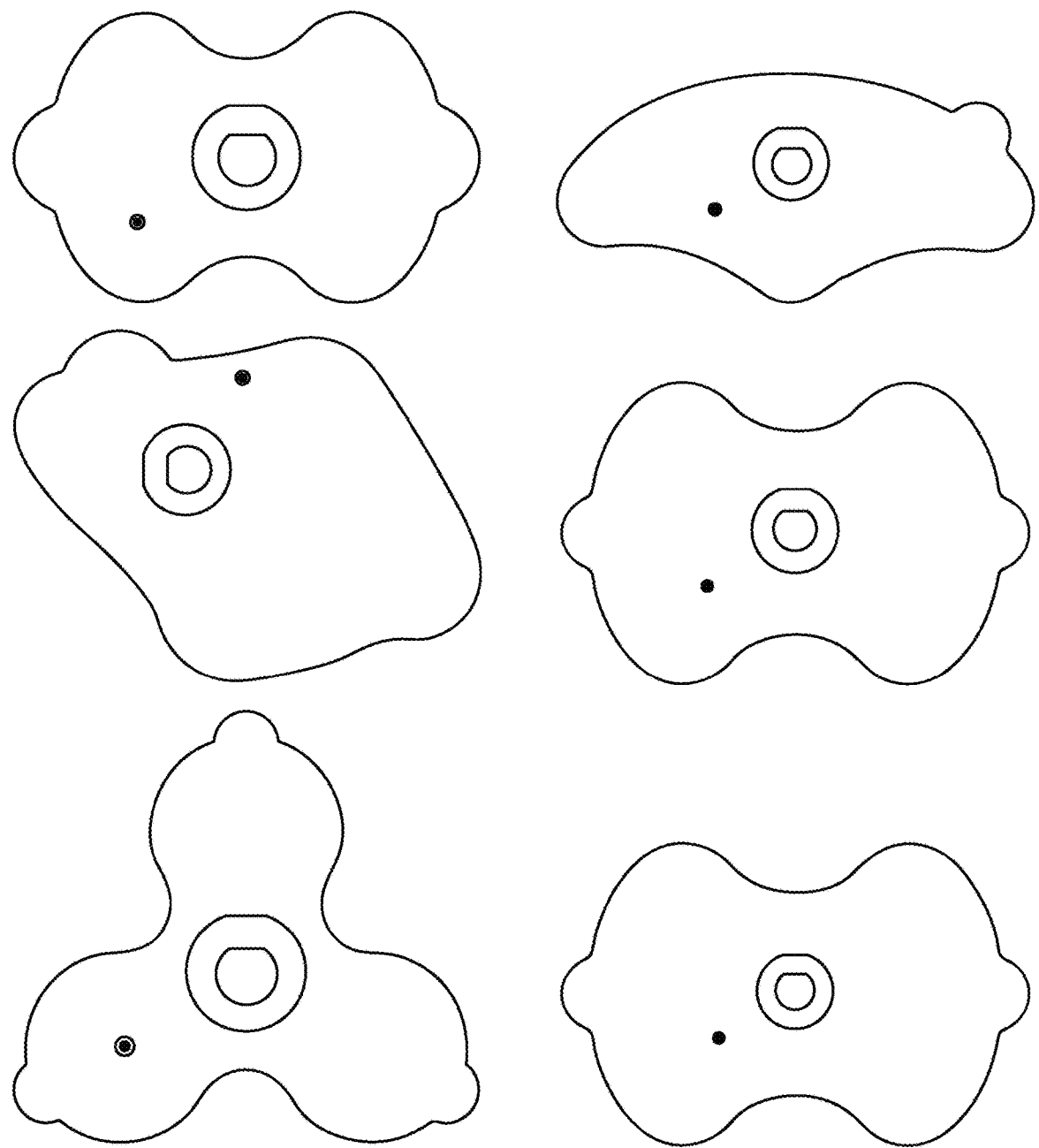

The light source may be in the form of an array, patch, pad, mask, wrap, fiber, bandage or cylinder, for example. The light source may have a variety of shapes and sizes. For example, the light source may be square, rectangular, circular, butterfly-shaped, elliptical, clover-shaped, oblong, crescent/moon-shaped, or any other shape that is suitable for a particular application. Examples of suitable light sources are generally illustrated in FIGS. 26A and 26B. The overall surface area of one side of the light source may range from, for example, 1 cm$^2$ to 1 m$^2$, or in panels placed together to cover larger areas, although typically the surface area is about 1 to 2000 cm$^2$ (e.g., about 1, 4, 9, 16, 25, 36, 49, 64, 81, 100, 121, 144, 169, 196, 225, 289, 324, 361, 400, 441, 484, 529, 576, 625, 676, 729, 784, 841, 900, 961, 1024, 1089, 1156, 122, 1296, 1369, 1444, 1521, 1600, 1681, 1764, 1849, 1936 or 2000 cm$^2$ or some range therebetween). The light source is thus well adapted to be applied to various areas of the subject's body, for example, the face, forehead, back, and the like. The light source may also be applied other types of surfaces, such as surfaces within a contaminated environment or surfaces inside of a refrigeration or food display system.

The various elements/layers of the light source will now be described in greater detail.

Substrate

In some embodiments, the light source includes a substrate. The substrate may be any substance capable of supporting the various layers of the light source. The substrate is preferably flexible and/or conformable to a surface in which the light source will be used, such as the contours of a subject's body, surfaces within a contaminated environment, or surfaces inside of a refrigeration, food display or processing system. The substrate can comprise, for example, an inorganic material, an organic material, or a combination of inorganic and organic materials. The substrate may be, for example, made from metals, plastics or glass. The substrate may be any shape to support the other components of the light source, for example, the substrate may be substantially flat or planar, curved, or have portions that are substantially flat portions and curved portions. Most preferably, the substrate is transparent, flexible, and conformable in nature. Ideally, the material is a latex-free, non-toxic, non-allergenic material, which is resistant to UV, sunlight and most infection control products.

As used herein, the term "transparent" generally means transparency for light and includes both clear transparency as well as translucency. Generally, a material is considered transparent if at least about 50%, preferably about 60%, more preferably about 70%, more preferably about 80% and still more preferably about 90% of the light illuminating the material can pass through the material. In contrast, the term "opaque" generally refers to a material in which the light is substantially absorbed or reflected, e.g., at least 90% of the light is absorbed or reflected, and typically at least 95% of the light is absorbed or reflected.

In some embodiments, the substrate may be comprised of a silicon-based material, rubber, thermoplastic elastomers (TTP), or other polymeric material, such as polyester, polyethylene terephthalate (PET), polyethylene naphthalate (PEN), polycarbonate, polystyrene, polyacryl, polyether sulfone (PES), etc. Transparent substrates may include, for example, polyethylene, ethylene-vinyl acetate copolymers, polyimide (PI), polyetherimide (PEI), ethylene-vinyl alcohol copolymers, polypropylene, polystyrene, polymethyl methacrylate, PVC, polyvinyl alcohol, polyvinylbutyral, polyether ether ketone, polysulfone, polyether sulfone, as well as fluoropolymers, such as, fluorinated ethylene-propylene (FEP), tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyester, polycarbonate, polyurethanes, polyimide or polyether imide.

In another embodiment, the transparent substrate is a polyester film, such as Mylar. In another aspect, the substrate comprises a polyetheretherketone film commercially available from Victrex under the name APTIV. In still another aspect, the substrate is a thin film sold under the name Flexent by Konica Minolta or flexible glass such as Willow Glass by Dow Corning. Ideally, substrates in direct or indirect contact with organic layers will have exceptional barrier capabilities that withstand heat, offer flexibility, have sustained reliability and can be mass produced Conductive Layers (Electrodes)

The light source comprises a plurality of conductive layers (i.e., electrodes), namely, a cathode and an anode. The anode may comprise, for example, a transparent conductive oxide (TCO), such as, but not limited to, indium tin oxide (ITO), zinc oxide (ZnO), and the like. The cathode may also comprise, for example, a thin metal film or fibers such as aluminum, copper, gold, molybdenum, iridium, magnesium, silver, lithium fluoride and alloys thereof, or a non-metal conductive layer.

Because the light source must emit light through one or both electrodes, at least one of the electrodes must be transparent. The transparent electrode is positioned on the side of the light source designed to be facing the surface to be irradiated. For a light source intended to emit light only through the bottom electrode (i.e., the surface-facing electrode), the top electrode (i.e., the electrode facing away from the surface) does not need to be transparent. The top electrode may thus comprise an opaque or light-reflective metal layer having a high electrical conductivity. Where a top electrode does not need to be transparent, using a thicker layer may provide better conductivity, and using a reflective electrode may increase the amount of light emitted through the transparent electrode by reflecting light back towards the transparent electrode. Fully transparent light sources may also be fabricated, where both electrodes are transparent.

The thickness of each electrode is typically about 200 nm or less (e.g., about 200, 180, 160, 140, 120, 100, 90, 80, 70, 60, 50, 40, 30 nm or less). Preferably, the thickness of each electrode is less than 10 nm (e.g., about 10, 9, 8, 7, 6, 5, 4, 3, 2, 1, 0.8, 0.6, 0.4, 0.2 nm or less or some range therebetween).

The electrodes are preferably flexible in nature. In some embodiments, the conductive materials of one or both of the electrodes may include, but are not limited to, transparent conductive polymer materials, such as indium tin oxide (ITO), fluorine-doped tin oxide (FTO), ZnO—Ga2O3, ZnO—Al2O3. SnO2-Sb2O3, and polythiophene In addition, the electrodes may be comprised of silver or copper grids or bushbars plated on a transparent substrate or silver nanowires or nanoparticles deposited on a substrate with a poly(3, 4-ethylenedioxythiophene) poly(styrenesulfonate) (PEDOT: PSS) coating. Additional conductive polymer layers may be added to improve conductivity.

In one aspect, the transparent conductive electrode may be carbon-based, for example, carbon nanotubes, carbon nanowires, or graphene, and the like. One preferred electrode (typically for infrared) comprises graphene. While one or two layers of graphene are preferred, the electrode may comprise about 1 to 20 layers of graphene (e.g., 1, 2, 3, 4, 5, 6, 7, 8, 9, 10, 11, 12, 13, 14, 15, 16, 17, 18, 19, 20 layers or some range therebetween). The graphene electrode(s) also have the effect of protecting the photoactive layer sandwiched between them from oxidation. Therefore, environmental stability of the light source can be improved. The graphene electrode may optionally have a plurality of plasmonic nanostructures, which may have various morphologies (spherical, rods, discs, prisms, etc.). Exemplary nanostructures include those made of gold, silver, copper, nickel, and other transition metals, for example gold nanoparticles, silver nanoparticles, copper nanoparticles, nickel nanoparticles, and other transition metal nanoparticles. In general, any electrically conductive materials, such as oxides and nitrides, of surface plasmonic resonance frequencies in the visible spectrum can be made into plasmonic nanostructures for the same purpose. In some embodiments, the plasmonic particles have the size of about 1 nm to about 300 nm (e.g., about 10, 50, 100, 150, 200, 250, 300 nm, or some range therebetween).

Light Emitter Layer

The light source includes a thin light emitter that may comprise, for example, OLEDs or printed LEDs (organic or inorganic). The thickness of the light emitter is preferably about 2 mm or less (e.g., about 2, 1.8, 1.6, 1.4, 1.2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01 mm or less). Most preferably, the flexible light emitter is about 10 to 200 nm in thickness (e.g., about 200, 180, 160, 140, 120, 100, 90, 80, 70, 60, 50, 40, 30, 20, 10 nm, or some range therebetween). The light emitter is preferably flexible and emits light in response to an electric current applied to the anode and cathode.

OLEDs

In some embodiments, the light source may comprise OLEDs in which the flexible light emitter is a thin organic film. As used herein, the term "organic" with respect to OLEDs encompasses polymeric materials as well as small molecule organic materials that may be used to fabricate organic opto-electronic devices. Such materials are well known in the art. "Small molecule" refers to any organic material that is not a polymer, and it will be appreciated that "small molecules" may actually be quite large. "Small molecules" may include repeat units in some circumstances. For example, using a long chain alkyl group as a substituent does not remove a molecule from the "small molecule" class. "Small molecules" may also be incorporated into polymers, for example as a pendent group on a polymer backbone or as a part of the backbone. "Small molecules" may also serve as the core moiety of a dendrimer, which consists of a series of chemical shells built on the core moiety. The core moiety of a dendrimer may be a fluorescent or phosphorescent small molecule emitter A dendrimer may be a "small molecule," and it is believed that all dendrimers currently used in the field of OLEDs are small molecules. In general, a "small molecule" has a well-defined chemical formula with a single molecular weight, whereas a polymer has a chemical formula and a molecular weight that may vary from molecule to molecule.

Generally speaking, in the flexible light emitter, electrons and holes recombine to radiate photons. The radiative photon energy emitted from the flexible light emitter corresponds to the energy difference between the lowest unoccupied molecular orbital (LUMO) level and the highest occupied molecular orbital (HOMO) level of the organic material. Photons of lower energy/longer wavelength may be generated by higher-energy photons through fluorescent or phosphorescent processes.

As described below, the flexible light emitter may optionally include one or more of a hole injection material (HIM), a hole transport material (HTM), a hole blocking material (HBM), an electron injection material (EIM), an electron transport material (ETM), an electron blocking material (EBM), and/or an exciton blocking material (ExBM).

In one aspect, the emissive electroluminescent layer may include a hole injection material (HIM). A HIM refers to a material or unit capable of facilitating holes (i.e., positive charges) injected from an anode into an organic layer. Typically, a HIM has a HOMO level comparable to or higher than the work function of the anode, i.e., −5.3 eV or higher.

In another aspect, the emissive electroluminescent layer may include a hole transport material (HTM). A HTM is characterized in that it is a material or unit capable of transporting holes (i.e., positive charges) injected from a hole injecting material or an anode. A HTM has usually high HOMO, typically higher than −5.4 eV. In many cases, HIM can also function as HTM, depending on the adjacent layer.

In another aspect, the emissive electroluminescent layer may include a hole blocking material (HBM). A HBM generally refers to a material which, if deposited adjacent to an emitting layer or a hole transporting layer in a multilayer structure, prevents the holes from flowing through. Usually it has a lower HOMO as compared to the HOMO level of the HTM in the adjacent layer. Hole-blocking layers are frequently inserted between the light-emitting layer and the electron-transport layer.

In another aspect, the emissive electroluminescent layer may include an electron injection material (EIM). An EIM generally refers to a material capable of facilitating electrons (i.e., negative charges) injected from a cathode into an organic layer. The EIM usually has a LUMO level comparable to or lower than the working function of the cathode. Typically, the EIM has a LUMO lower than −2.6 eV.

In another aspect, the emissive electroluminescent layer may include an electron transport material (ETM). An ETM generally refers to a material capable of transporting electrons (i.e., negative charges) injected from an EIM or a cathode. The ETM has usually a low LUMO, typically lower than −2.7 eV. In many cases, an EIM can serve as an ETM as well, depending on the adjacent layer.

In another aspect, the emissive electroluminescent layer may include an electron blocking material (EBM). An EBM generally refers to a material which, if deposited adjacent to an emissive or electron transporting layer in a multilayer structure, prevents the electron from flowing through. Usually it has a higher LUMO as compared to the LUMO of the ETM in the adjacent layer.

In another aspect, the emissive electroluminescent layer may include an exciton blocking material (ExBM). An ExBM generally refers to a material which, if deposited adjacent to an emitting layer in a multilayer structure, prevents the excitons from diffusing through. ExBM should have either a higher triplet level or singlet level as compared to the emitting layer or other adjacent layer.

Exemplary OLED materials are described in Hammond et al., U.S. Published Patent Application No. 2010/0179469; Pan et al., U.S. Published Patent Application No. 2013/0006119; Buchholz et al., PCT Published Patent Application No. WO 2012/010238; and Adamovich et al., U.S. Published Patent Application No. 2007/0247061.

Figure 27:
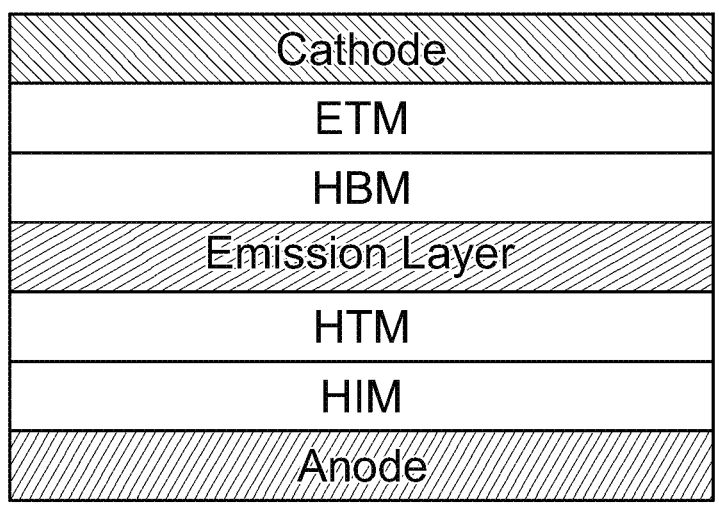
FIG. 27 illustrates an exemplary OLED structure for use in the light source of FIG. 25.

Referring to FIG. 27, a typical sequence of materials found in the flexible light emitter between the anode and the cathode of the OLED is HIM, HTM, emission layer, HBM, and ETM. Another typical sequence of materials is HTM, emission layer, and ETM. Of course, other sequences of materials are also possible. Further, the OLED may comprise one or more interlayers.

In one aspect, the flexible light emitter comprises a single layer. The flexible light emitter may comprise, for example, a conjugated polymer which is luminescent, a hole-transporting polymer doped with electron transport molecules and a luminescent material, or an inert polymer doped with hole transporting molecules and a luminescent material. The flexible light emitter may also comprise an amorphous film of luminescent small organic molecules which can be doped with other luminescent molecules.

In another aspect, the flexible light emitter may comprise one or more different emissive materials in either the same emission layer or in different emission layers. For example, the flexible light emitter may comprise 5, 4, 3, 2, or 1 radiation emitting materials. The various different emissive materials may be selected from the emissive materials described in the references set forth above, but any other suitable emissive material can be employed. If two emissive materials are used in one emission layer, the absorption spectrum of one of the two emissive materials preferably overlaps with the emission spectrum of the other emissive material. The emissive materials may be arranged in stacked layers or side-by-side configurations. The emissive layer may comprise a continuous region forming a single emitter or a plurality of light emitters. The plurality of light emitters may emit light with substantially different wavelengths. The plurality of light emitters may be vertically stacked within the emissive layer or they may form a mixture. In some embodiments, a dopant is dispersed within an organic host matrix. In one embodiment, a layer of quantum dots is sandwiched between two organic thin films.

In another aspect, the flexible light emitter may comprise a plurality of layers sharing a common anode and/or cathode. In this case, individual layers are stacked one on top of another. The stacked configuration may generally include intermediate electrodes disposed between adjacent layers such that successive layers share an intermediate electrode, i.e., a top electrode of one layer is the bottom electrode of another in the stack. The stacked layers may be formed of different materials, and therefore, different emissions spectra.

The flexible light emitter may be substantially transparent. When mostly transparent layers are used, a plurality of emissive layers may be vertically stacked without substantially blocking light emission from individual layers. The flexible light emitter may comprise a single or multiple layers, for example, a combination of p- and n-type materials. The p- and n-type materials may be bonded to each other in the layer. The bonding may be ionic or covalent bonding, for example. The multiple layers of the flexible light emitter may form heterostructures therebetween.

Printed LEDs

In some embodiments, the light source may comprise printed LEDs (organic or inorganic), i.e., LED ink. With LED ink, each light source is very small which enables the LEDs to be positioned in very close proximity to each other. During fabrication, the LEDs may be printed in a uniform manner whereby each LED operates as a point source in which the beams from the individual LEDs are substantially parallel to each other to provide substantially uniform light across the surface of the device. Unlike conventional LEDs, printed LEDs do not need to be positioned a sufficient distance from the surface to be irradiated in order to deliver a substantially uniform dose of light. There are several known methods for printing such LEDs, as described below.

In one method, a plurality of individual LEDs are suspended and dispersed in a liquid or gel comprising one or more solvents and a viscosity modifier so as to form a diode ink that is capable of being printed on a flexible substrate (e.g., through screen printing, flexographic printing and the like). In one aspect, the average surface area concentration of LEDs is from about 25 to 50,000 LEDs per square centimeter. In general, each LED includes a light emitting region, a first metal terminal located on a first side of the light emitting region, and a second metal terminal located on a second side of the light emitting region. The first and second metal terminals of each LED may be electrically coupled to conductive layers (i.e., electrodes) to enable the light emitting region to emit light when energized.

Figure 28:
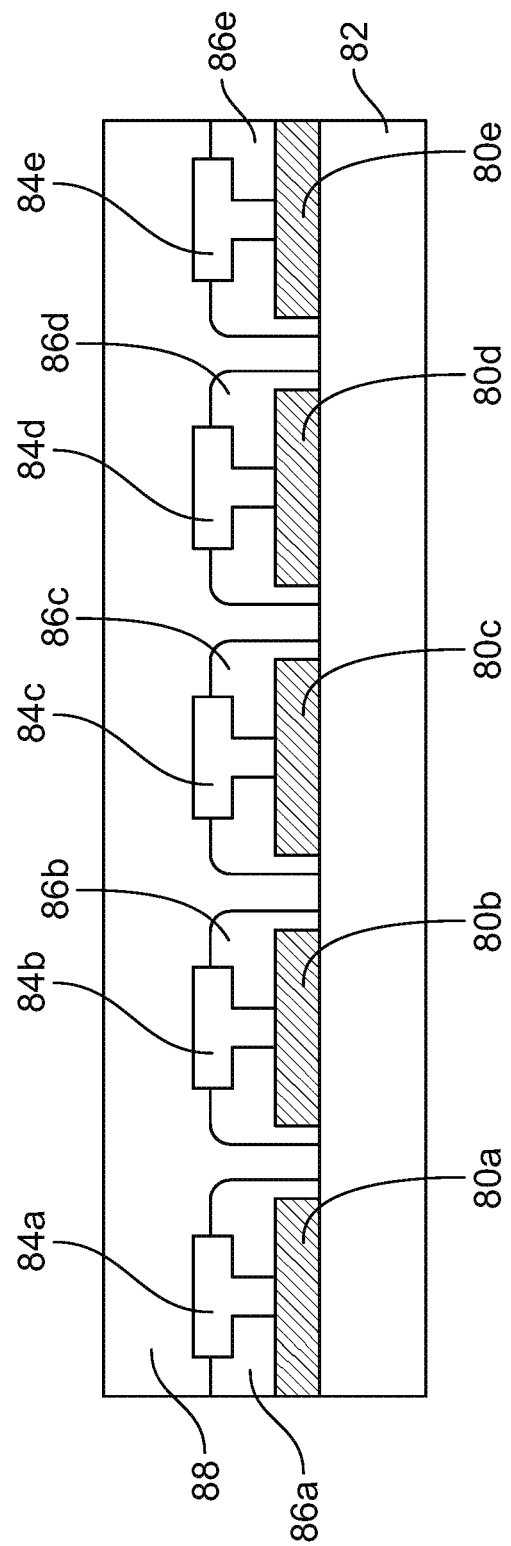
FIG. 28 illustrates an exemplary printable LED structure for use in the light source of FIG. 25.

An exemplary light source is shown generally in FIG. 28, wherein only five LEDs are provided in order to simplify the description. As can be seen, this device includes a plurality of conductors 80a-80e deposited on a flexible substrate 82. A plurality of LEDs 84a-84e are deposited on the conductors 80a-80e such that the first metal terminals of the LEDs 84a-84e are electrically coupled to the conductors 80a-80e. One skilled in the art will appreciate that the LEDs 84a-84e may be formed of various shapes. Preferably, the LEDs 84a-84e settle into a position over conductors 80a-80e such that they maintain their polarity based on the shape of the LEDs. Next, a plurality of dielectric layers 86a-86e are deposited over the LEDs 84a-84e and the conductors 80a-80e, as shown. Another conductor 88 is then deposited over the LEDs 84a-84e and dielectric layers 86a-86e such that the second metal terminals of the LEDs 84a-84e are coupled to the conductor 88. One skilled in the art will appreciate that the substrate 82 and conductors 80a-80e may be transparent so that light is emitted from the bottom of the device and/or conductor 82 may be transparent so that light is emitted from the top of the device. Various configurations of printed LEDs that may be manufactured in accordance with the above method are described in Lowenthal et al., U.S. Pat. No. 8,415,879.

In another method, the light source comprises LEDs that are created through a printing process. In this method, a substrate is provided that includes a plurality of spaced-apart channels. A plurality of first conductors are formed on the substrate such that each first conductor is positioned in one of the channels. Next, a plurality of substantially spherical substrate particles are coupled to the first conductors and, then the substantially spherical substrate particles are converted into a plurality of substantially spherical diodes. The substantially spherical diodes may comprise, for example, semiconductor LEDs, organic LEDs encapsulated organic LEDs, or polymer LEDs. A plurality of second conductors are then formed on the substantially spherical diodes. Finally, a plurality of substantially spherical lenses suspended in a polymer (wherein the lenses and suspending polymer have different indices of refraction) are deposited over the substantially spherical diodes and the second conductors. Thus, in this method, the LED's are built up on the substrate as opposed to being mounted on the substrate. Various configurations of printable LEDs that may be manufactured in accordance with the above method are described in Ray et al., U.S. Pat. No. 8,384,630.

In an exemplary embodiment, the light source is comprised of printed LEDs having a thickness of 12 µm, silver electrodes each of which has a thickness of 5-10 µm with a transparent silver fiber having a thickness of 0.05-5 µm, and a PET substrate having a thickness of 125 µm.

Micro-Lens Array

The light source may optionally include a light dispersion layer, such as a micro-lens array. It has been found that one of the key factors that limits the efficiency of OLED devices is the inefficiency in extracting the photons generated by the electron-hole recombination out of the OLED devices. Due to the high optical indices of the organic materials used, most of the photons generated by the recombination process are actually trapped in the devices due to total internal reflection. These trapped photons never leave the OLED devices and make no contribution to the light output from these devices. In order to improve the extraction or outcoupling of light from OLEDs, the device may include an internal scattering layer of high index particles such as TiOx in a transparent photoresist or a micro-lens array (MLA) layer. Exemplary MLAs and methods for forming the same are described in Gardner et al., U.S. Published Patent Application No. 2004/01217702; Chari et al. U.S. Pat. No. 7,777,416; Xu et al., U.S. Pat. No. 8,373,341; Yamae et al., *High-Efficiency White OLEDs with Built-up Outcoupling Substrate*, SID Symposium Digest of Technical Papers, 43 694 (2012); and Komoda et al., *High Efficiency Light OLEDS for Lighting*, J. Photopolymer Science and Technology, Vol. 25, No. 3 321-326 (2012).

Barrier Layer

The light source may optionally include one or more encapsulation or barrier layers that isolate the light emitter (or other layers) from an ambient environment. The encapsulation or barrier layer is preferably substantially impermeable to moisture and oxygen. In general, the moisture and oxygen sensitive components should be enclosed by materials having gas permeation properties. The barrier preferably achieves low water vapor permeation rates of $10^4$ g/m$^2$/day or less, $10^{-5}$ g/m$^2$/day or less, and even more preferably about $10^6$ g/m$^2$/day or less.

The encapsulation or barrier layer may be glass or a plastic, for example. Exemplary materials include a polyetheretherketone film commercially available from Victrex under the name APTIV. In still another aspect, the substrate is a thin film sold under the name Flexent by Konica Minolta or flexible glass such as Willow Glass by Dow Corning. Ideally, substrates in direct contact with organic layers will have exceptional barrier capabilities that withstand heat, offer flexibility, have sustained reliability and can be mass produced.

The light source may be further covered with a transparent or semi-transparent covering. The covering may provide comfort for a subject using the light source. The covering may provide protection to the light source, keeping dirt and fluid off of the device and providing a cushion to protect the device from impact.

Quantum Dot Layer

In some embodiments, a layer of quantum dots is used between the light emitting surface and the surface to be irradiated in order to convert all or a portion of the light emission into a different wavelength. The wavelength is typically down converted to a longer wavelength (Stokes conversion). For example, purple or blue light may be converted into red light at 630 nm. Quantum dots may contain cadmium or may be organic and cadmium free. Wavelength conversion may occur with many wavelengths thus providing an additional or multiple wavelengths from a fixed wavelength source. Quantum dots may also be embedded into the hydrogel used to connect the light source to the surface to be irradiated, such as a skin or tissue surface. This may consist of a film or encapsulated quantum dots layered on the surface of the hydrogel or the light emitting surface of the lamp. Various densities of quantum dots can be used to control the percentage of light converted from one wavelength to another. For example, testing was performed using 50% and 75% blue light and 50% and 25% red light in bacterial kill experiments. This combination had an effect on the killing of *P. acnes* and may be added to enhance the anti-inflammatory effects of the light due to the addition of red light. The quantum dot converts light as it receives the incident light so the continuous or pulse characteristic of the light is maintained.

Bottom and Top Light Emitting Configurations

In some embodiments, the light source has a "bottom" light emitting configuration or a "top" light emitting configuration.

Figure 29:
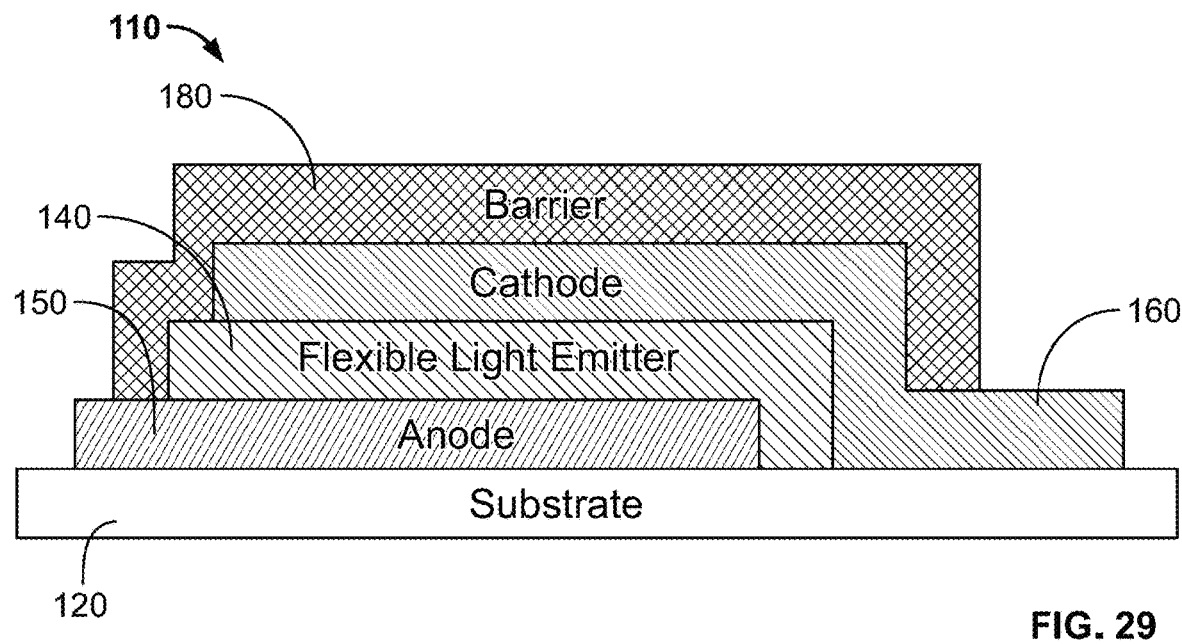
FIG. 29 illustrates a light source with a bottom light emitting configuration that is suitable for delivering pulsed light in accordance with the present invention.

FIG. 29 illustrates an exemplary embodiment of a light source 110 with a "bottom" light emitting configuration. Light source 110 comprises a flexible light emitter 140 located between an anode 150 and a cathode 160, all of which are formed on a transparent substrate 120. A power source (not shown) is provided so that DC or pulsed DC is used to power the light source. Further, a transparent barrier layer 180 protects the flexible light emitter 140 from moisture and oxygen.

In this embodiment, the flexible light emitter 140 comprises an OLED or printed LEDs. Both the substrate 120 and the anode 150 are transparent. The substrate is comprised of a transparent silicon rubber. The anode 150 is comprised of ITO. Light generated from the flexible light emitter 140 is emitted through the transparent anode 150 and substrate 120 such that the device has a "bottom" light emitting configuration. The cathode 160 is comprised of a conductive metal such as silver. The barrier layer is comprised of Flexent film (Konica Minolta).

Figure 30:
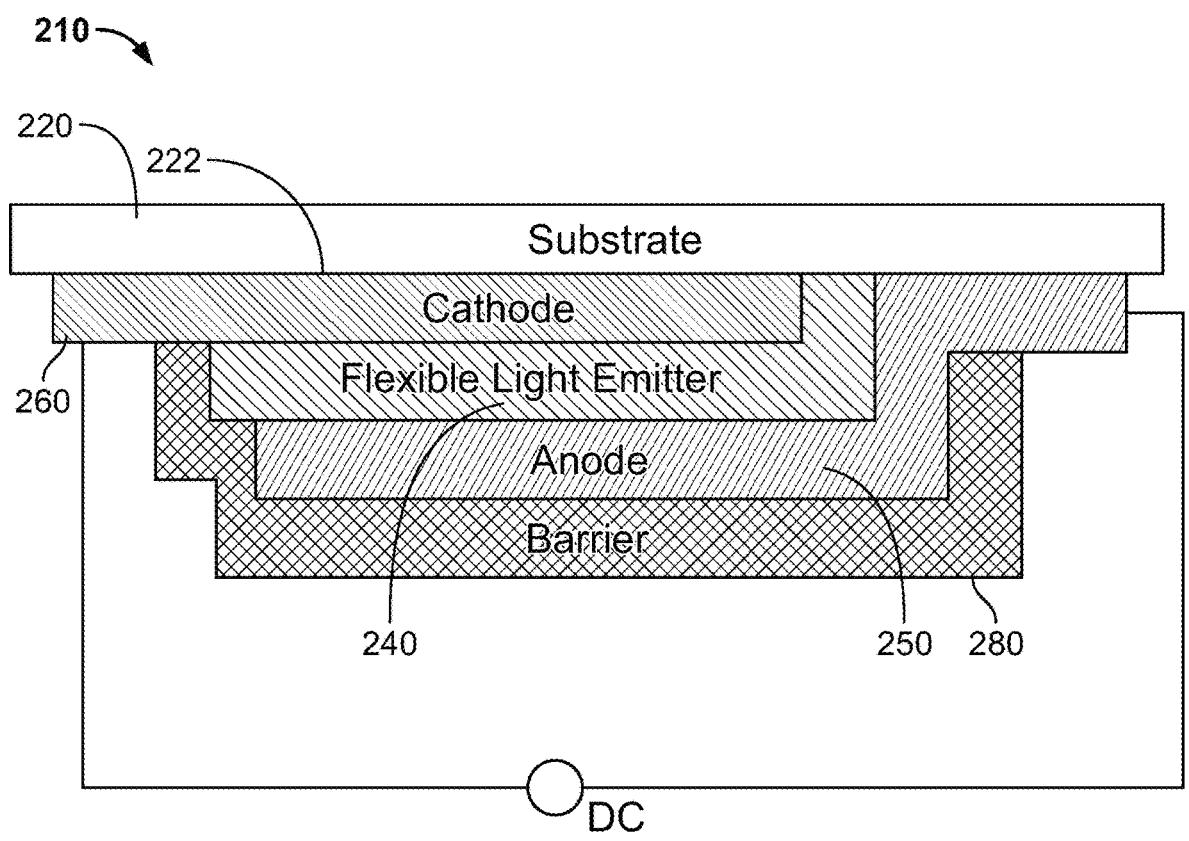
FIG. 30 illustrates a light source with a top light emitting configuration that is suitable for delivering pulsed light in accordance with the present invention.

FIG. 30 illustrates an exemplary embodiment of a light source 210 with a "top" light emitting configuration. Light source 210 comprises a flexible light emitter 240 located between an anode 250 and a cathode 260, all of which are formed on a bottom surface 222 of a substrate 220 (i.e., the surface facing towards a surface to be irradiated). A power source (not shown) is provided so that DC or pulsed DC is used to power the light source. Further, a transparent barrier layer 280 protects the flexible light emitter 240 from moisture and oxygen.

In this embodiment, the flexible light emitter 240 comprises an OLED or printed LEDs. The substrate 220 comprises a Mylar film and a silver nanolayer is coated on its bottom side to form the cathode 260 of the light source. The silver nanolayer is highly reflective to the light generated by the flexible light emitter 240 such that the light is directed towards the surface to be irradiated. Both the barrier layer 280 and the anode 250 are transparent. The barrier layer 280 is comprised of Willow transparent flexible glass (Dow Corning). The anode 250 is comprised of ITO. Light generated from the flexible light emitter 240 is emitted through the transparent anode 250 and barrier layer 280 such that the device has a "top" light emitting configuration.

Hydrogel or Adhesive Layer

In some embodiments, a transparent hydrogel, silicone membrane or adhesive layer such as Dow silicone PSA or double-sided adhesive tape layer is applied between the light emitting surface of the lamp to attach it to the surface to be irradiated, such as a skin or tissue surface. This layer may be a single use disposable in cases where certain microorganisms are able to penetrate the hydrogel, silicone or adhesive layer. As such, the hydrogel, silicone or adhesive layer is not suitable for re-use due to the infection control requirements and non-transmittal of infection back to the user or subsequent users of the device. Alternatively, this layer may be used multiple times in cases where there is no microorganism penetration. For example, studies have shown that certain bacteria do not grow on the surface of a hydrogel or silicone layer. The hydrogel, silicone or adhesive layers may also contain additional anti-bacterials and substances suitable to enhance tissue regeneration for use in wound healing. The double-sided transparent adhesive tape may be, for example, 3M 9964 Clear Polyester Diagnostic Microfluidic Medical Tape (3M.com). Various hydrogels and silicones are available based on the adhesion requirements for various skin types and wound dressings.

VII. Control of Light Source

The light source is driven and controlled by an electronic circuit that includes, for example, a power supply, drive circuit and control module. For flexible light sources, the electronic circuit may be provided in a separate housing electrically connected to the light source or may be built into the flexible material that mounts the light source.

The power supply may be any power supply capable of supplying sufficient power to activate the light source. The power supply may comprise a disposable or rechargeable battery, solar cell, fuel cell, an adapter, or may be powered by the power grid. The battery may be a printed battery, flexible lithium-ion primary or secondary cells, carbon nanotube, electrochemical inks, or other flexible organic or inorganic primary or secondary cells using non-toxic or limited toxicity materials. In some embodiments, the battery is roll-to-roll printed on the lamp substrate. The light source is preferably driven by DC or pulsed DC. One skilled in the art will understand that the output voltages and current levels of the DC or pulsed DC control the peak output of each layer of the device, which in combination with the treatment time control the dose.

Figure 31:
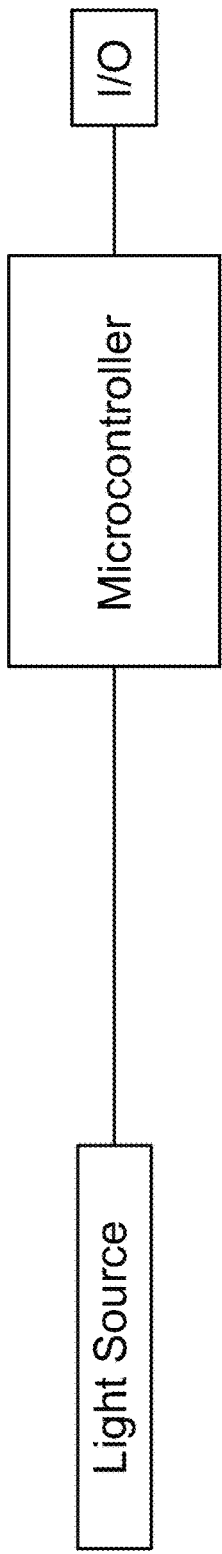
FIG. 31 is a block diagram of an electronic circuit for controlling a light source in accordance with the present invention, wherein the electronic circuit includes a drive circuit and microcontroller that is preprogrammed to provide a fixed dose of light.

FIG. 31 is a block diagram of an exemplary system in which the light source and light source drive circuit are controlled by a microcontroller (discussed below) in accordance with a preprogrammed treatment cycle that provides a sequence of light at a fixed dose or wavelength based on the patch configuration. For example, the microcontroller may be preprogrammed for treatment of a specific disorder, such as acne. The microcontroller may control the light source by adjusting the activation and deactivation of the light source, voltage, current, light wavelength, pulse width, duty factor, and light treatment time. One skilled in the art will appreciate that other operating parameters may also be controlled by the microcontroller in accordance with the present invention.

The microcontroller is also connected to one or more I/O devices, such as an LED that provides an indication of whether the light source is on/off or an audio buzzer that alerts the user upon completion of a particular treatment. An on/off switch may also be provided to power the light source.

The system may be used in a number of treatment (irradiation) sessions that together result in an overall treatment time. For such cases, the microcontroller may include at least one timer configured to measure session time and overall treatment time or both. The timer may be used simply to monitor the session time or overall treatment time or may be used to deactivate the light source after completion of a session or overall treatment. The timer may also be used to provide sequential treatments for automatic dosing in a wound care dressing, for example. A real time clock associated with the system can monitor the treatments and track/manage treatment sequences and dosing.

Figure 32:
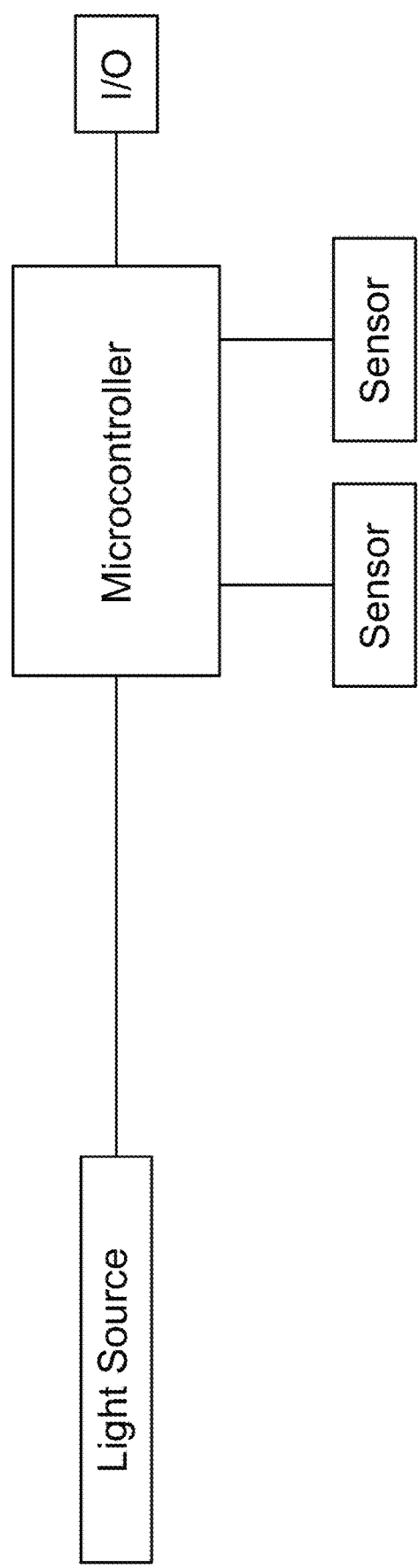
FIG. 32 is a block diagram of an electronic circuit for controlling a light source in accordance with the present invention, wherein the electronic circuit includes sensors that operate in a closed loop to provide feedback to a microcontroller so as to dynamically control the light source.

FIG. 32 is a block diagram of an exemplary system in which the light source is controlled by an electronic circuit with one or more sensors that operate in a closed loop to provide feedback to a microcontroller so as to dynamically control the light source during a treatment (irradiation) session. As can be seen, the electronic circuit is similar to that shown and described in connection with FIG. 31, with the addition of one or more sensors that operate in a closed loop to provide feedback to the microcontroller. For example, in applications involving the photoeradication of *P. acnes* and other microorganisms, a photo sensor could be used to detect porphyrins or other spectra related to the inactivation of the bacteria that emit light within the red or other wavelength portion of the fluorescent spectrum, as discussed above. An exemplary sensor is a photo sensor used to detect porphyrins that emit light within the red or other portion of the fluorescent spectrum in applications involving the photoeradication of *P. acnes* with pulsed purple or blue light or other spectra related to the inactivation of the bacteria. The photo sensor may comprise, for example, a photo detector with a sharp purple or blue notch filter and a bandpass filter that is used to detect the red or other wavelength portion of the fluorescent spectrum. This would be monitored during treatment and as it decayed to a preset threshold the pulsed purple or blue light stimulation would be turned off. From time to time, the system would turn on to see if the porphyrin levels would return to a high enough level to induce microorganism kill upon exposure to pulsed purple or blue light. Of course, other types of sensors may also be used in accordance with the invention. Certain sensors may be built into the layers of the device, while other sensors may be applied to the skin or other surface to be irradiated or may be built into the illuminator.

Unless defined otherwise, all technical and scientific terms used herein have the same meaning as commonly understood by one of ordinary skill in the art to which the disclosure pertains. Also, as will be understood by one skilled in the art, for any and all purposes, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As will also be understood by one skilled in the art, a range includes each individual member.

While the present invention has been described and illustrated hereinabove with reference to several exemplary embodiments, it should be understood that various modifications could be made to these embodiments without departing from the scope of the invention. Therefore, the present invention is not to be limited to the specific methodologies or device configurations of the exemplary embodiments, except insofar as such limitations are included in the following claims.

What is claimed and desired to be secured by Letters Patent is as follows:

1. A method for photoeradication of microorganisms from a target, the method comprising:
    irradiating the microorganisms of the target with a sequence of light pulses having a plurality of pulse parameters and a wavelength that ranges from 380 nm to 500 nm, wherein the pulse parameters comprise (a) a peak irradiance and a pulse duration for each of the light pulses sufficient to optically excite a photoactive molecule capable of photoeradication of the microorganisms and (b) an off time between each two adjacent light pulses sufficient to allow the photoactive molecule to return to a ground state creating an oxidation reaction that produces free radicals which destroy a cellular structure of the microorganisms, wherein the pulse parameters are selected from test data that associates each of a plurality of sets of pulse parameters with a survival rate for the microorganisms after irradiation with the sequence of light pulses, wherein the survival rate associated with the selected pulse parameters is between 0% and 50%.

2. The method of claim 1, wherein the photoactive molecule comprises an endogenous molecule present in the microorganisms.

3. The method of claim 2, wherein the microorganisms comprise *Propionibacterium acnes* and the photoactive molecule comprises porphyrin.

4. The method of claim 1, wherein the photoactive molecule comprises an exogenous molecule applied to the target.

5. The method of claim 4, wherein the microorganisms comprise Group B *Streptococcus* and the photoactive molecule comprises a photosensitizer.

6. The method of claim 5, wherein the photosensitizer comprises one of protoporphyrin IX (PPIX), coproporphyrin III (CP III), flavin mononucleotide (FMN), or nicotinamide adenine dinucleotide (NAD).

7. The method of claim 1, wherein the peak irradiance of the light pulses ranges from 0.3 mW/cm$^2$ to 60 mW/cm$^2$, the pulse duration of the light pulses ranges from 5 microseconds to 1,000 microseconds, and the off time between the light pulses ranges from 10 microseconds to 1 second.

8. The method of claim 7, wherein the light pulses are provided at a duty factor that ranges from 20% to 33% and a pulse repetition rate that ranges from 33 kHz to 40 kHz.

9. The method of claim 1, wherein the sequence of light pulses is applied to the microorganisms of the target in accordance with an irradiation schedule that includes a plurality of irradiation sessions.

10. The method of claim 9, wherein each of the irradiation sessions occurs during a depletion stage of the photoactive molecule following application of the photoactive molecule to the target.

11. The method of claim 1, wherein the target comprises one of a region of skin, a tissue or a wound infected by the microorganisms so as to cause a bacterial infection.

12. The method of claim 1, wherein the target comprises an environment contaminated with the microorganisms.

13. The method of claim 1, wherein the target comprises food contaminated with the microorganisms.

14. A method for photoeradication of microorganisms from a target, the method comprising:
obtaining test data for each of a plurality of experiments, wherein each experiment comprises irradiating test microorganisms supplemented with an exogenous photoactive molecule with a sequence of light pulses having a plurality of pulse parameters and a wavelength that ranges from 380 nm to 500 nm, wherein the pulse parameters comprise a peak irradiance for each of the light pulses, a pulse duration for each of the light pulses, and an off time between each two adjacent light pulses, and wherein the test data comprises a survival rate for the test microorganisms after irradiation with the light pulses;
analyzing the test data to identify the pulse parameters that result in a survival rate for the test microorganisms of between 0% and 50%;
applying the exogenous photoactive molecule to the target; and
irradiating the microorganisms of the target with the light pulses having the identified pulse parameters in accordance with an irradiation schedule.

15. The method of claim 14, wherein the microorganisms comprise Group B *Streptococcus* and the exogenous photoactive molecule comprises a photosensitizer.

16. The method of claim 15, wherein the photosensitizer comprises one of protoporphyrin IX (PPIX), coproporphyrin III (CP III), flavin mononucleotide (FMN), or nicotinamide adenine dinucleotide (NAD).

17. The method of claim 14, wherein the peak irradiance of the light pulses ranges from 0.3 mW/cm$^2$ to 60 mW/cm$^2$, the pulse duration of the light pulses ranges from 5 microseconds to 1,000 microseconds, and the off time between the light pulses ranges from 10 microseconds to 1 second.

18. The method of claim 17, wherein the light pulses are provided at a duty factor that ranges from 20% to 33% and a pulse repetition rate that ranges from 33 kHz to 40 kHz.

19. The method of claim 14, wherein the irradiation schedule that includes a plurality of irradiation sessions.

20. The method of claim 19, wherein each of the irradiation sessions occurs during a depletion stage of the photoactive molecule following application of the photoactive molecule to the target.

21. The method of claim 14, wherein the target comprises one of a region of skin, a tissue or a wound infected by the microorganisms so as to cause a bacterial infection.

22. A method for photoeradication of microorganisms from a target, the method comprising:
determining a plurality of pulse parameters for a sequence of light pulses having a wavelength that ranges from 380 nm to 500 nm, wherein the pulse parameters comprise (a) a peak irradiance and a pulse duration for each of the light pulses that are selected to enable excitation of an exogenous photoactive molecule associated with the microorganisms and (b) an off time between each two adjacent light pulses that is selected to enable return of the exogenous photoactive molecule to a ground state to thereby create an oxidation reaction that produces free radicals which destroy a cellular structure of the microorganisms;
determining an irradiation schedule for application of the light pulses having the pulse parameters during each of a plurality of irradiation sessions, wherein each of the irradiation sessions occurs during a depletion stage of the photoactive molecule following application of the exogenous photoactive molecule to the target;
applying the exogenous photoactive molecule to the target; and
irradiating the microorganisms of the target with the light pulses having the pulse parameters in accordance with the irradiation schedule.

23. The method of claim 22, wherein the microorganisms comprise Group B *Streptococcus* and the exogenous photoactive molecule comprises a photosensitizer.

24. The method of claim 23, wherein the photosensitizer comprises one of protoporphyrin IX (PPIX), coproporphyrin III (CP III), flavin mononucleotide (FMN), or nicotinamide adenine dinucleotide (NAD).

25. The method of claim 22, wherein the irradiation sessions are also timed to target the microorganisms at a specified time during a replication cycle of the microorganisms.

26. The method of claim 22, wherein the irradiation schedule results in a survival rate for the microorganisms of less than 50%.

27. The method of claim 22, wherein the irradiation schedule results in a survival rate for the microorganisms of less than 10%.

28. The method of claim 22, wherein the irradiation schedule results in a survival rate for the microorganisms of 0%.

29. The method of claim 22, wherein the sequence of light pulses has an average irradiance that ranges from 0.1 mW/cm$^2$ to 20 mW/cm$^2$ and is provided at a radiant exposure that ranges from 0.5 J/cm$^2$ to 60 J/cm$^2$ during each of the irradiation sessions.

30. The method of claim 22, wherein the sequence of light pulses is provided at a fixed dose during each of the irradiation sessions.

31. The method of claim 22, wherein the sequence of light pulses is provided at a dose controlled by feedback from a photo sensor during each of the irradiation sessions, wherein the photo sensor detects light emitted during irradiation of the microorganisms and wherein each of the irradiation sessions is terminated when the detected light reaches a predetermined minimum level.

32. The method of claim 22, wherein the target comprises one of a region of skin, a tissue or a wound infected by the microorganisms so as to cause a bacterial infection.

33. The method of claim 22, wherein the target comprises an environment contaminated with the microorganisms.

34. The method of claim 22, wherein the target comprises food contaminated with the microorganisms.

35. The method of claim 11, wherein the bacterial infection comprises one of acne, psoriasis, cellulitis, erysipelas, erythrasma, folliculitis and skin abscesses, hidradenitis suppurativa, impetigo and ecthyma, lymphadenitis, lymphangitis, necrotizing skin infections, staphylococcal scalded skin syndrome, wound infection, tissue infection, and osteomyelitis.

36. The method of claim 12, wherein the microorganisms comprise community associated methicillin-resistant *Staphylococcus aureus* (MRSA).

37. The method of claim 36, wherein the contaminated environment comprises one of a locker room, a public or private restroom, an airplane, a school, a beach, a playground, and a playing field.

38. The method of claim 12, wherein the microorganisms comprise hospital associated methicillin-resistant *Staphylococcus aureus* (MRSA).

39. The method of claim 38, wherein the contaminated environment comprises one of a hospital and a clinical environment.

40. The method of claim 13, wherein the microorganisms comprise one of *Salmonella* spp., *E. coli*, and *Listeria* spp.

41. The method of claim 40, wherein the food is contained within one of a refrigeration system, a food display system, a food storage area, and a food processing system.

42. The method of claim 9, wherein the sequence of light pulses has an average irradiance that ranges from 0.1 mW/cm$^2$ to 20 mW/cm$^2$ and is provided at a radiant exposure that ranges from 0.5 J/cm$^2$ to 60 J/cm$^2$ during each of the irradiation sessions.

43. The method of claim 9, wherein the irradiation sessions are timed to target the microorganisms at a specified time during a replication cycle of the microorganisms.

44. The method of claim 9, wherein the sequence of light pulses is provided at a radiant exposure that ranges from 3.6 J/cm$^2$ to 20 J/cm$^2$ during each of the irradiation sessions.

45. The method of claim 19, wherein the sequence of light pulses has an average irradiance that ranges from 0.1 mW/cm$^2$ to 20 mW/cm$^2$ and is provided at a radiant exposure that ranges from 0.5 J/cm$^2$ to 60 J/cm$^2$ during each of the irradiation sessions.

46. The method of claim 19, wherein the irradiation sessions are timed to target the microorganisms at a specified time during a replication cycle of the microorganisms.

47. The method of claim 19, wherein the sequence of light pulses is provided at a radiant exposure that ranges from 3.6 J/cm$^2$ to 20 J/cm$^2$ during each of the irradiation sessions.

* * * * *

UNITED STATES PATENT AND TRADEMARK OFFICE
CERTIFICATE OF CORRECTION

PATENT NO. : 10,981,017 B2
APPLICATION NO. : 16/205182
DATED : April 20, 2021
INVENTOR(S) : Chukuka S. Enwemeka and John C. Castel It is certified that error appears in the above-identified patent and that said Letters Patent is hereby corrected as shown below:

In the Specification

Column 5
Line 14, delete "CP II" and replace it with "CP III" - therefor.

In the Claims

Column 41
Line 46, delete "that" between "schedule" and "includes".

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*